(12) United States Patent
Abrahamian et al.

(10) Patent No.: US 9,896,460 B2
(45) Date of Patent: Feb. 20, 2018

(54) MOLECULAR SWITCHES BASED ON CIS/TRANS ISOMERIZATION OF BF2-COORDINATED AZO COMPOUNDS

(71) Applicant: The Trustees of Dartmouth College, Hanover, NH (US)

(72) Inventors: Ivan Abrahamian, Hanover, NH (US); Russell P. Hughes, Lebanon, NH (US); Yin Yang, Hanover, NH (US)

(73) Assignee: THE TRUSTEES OF DARTMOUTH COLLEGE, Hanover, NH (US)

( * ) Notice: Subject to any disclaimer, the term of this patent is extended or adjusted under 35 U.S.C. 154(b) by 0 days.

(21) Appl. No.: 15/056,580

(22) Filed: Feb. 29, 2016

(65) Prior Publication Data
US 2016/0251379 A1    Sep. 1, 2016

Related U.S. Application Data

(63) Continuation of application No. PCT/US2014/052983, filed on Aug. 27, 2014.

(60) Provisional application No. 61/870,572, filed on Aug. 27, 2013.

(51) Int. Cl.
*C07F 5/02* (2006.01)
*A61N 5/06* (2006.01)

(52) U.S. Cl.
CPC .............. *C07F 5/022* (2013.01); *A61N 5/062* (2013.01); *C07F 5/02* (2013.01); *A61N 2005/066* (2013.01); *A61N 2005/0662* (2013.01)

(58) Field of Classification Search
CPC ............. C07F 5/02; C07F 5/022; A61N 5/062
See application file for complete search history.

(56) References Cited

U.S. PATENT DOCUMENTS

| 2005/0107335 A1 | 5/2005 | O'Shea et al. |
| 2011/0207213 A1 | 8/2011 | Trauner et al. |
| 2017/0037063 A1 | 2/2017 | Abrahamian et al. |

OTHER PUBLICATIONS

Yang et al. "Visible Light Switching of a BF2-Coordinated Azo Compound" Journal of the American Chemical Society, vol. 134, pp. 15221-15224.*
Bandara et al. (Jun. 2010), "Proof for the concerted inversion mechanism in the trans—>cis isomerization of azobenzene using hydrogen bonding to induce isomer locking," J. Org. Chem. 2010, 75, 4817-4827.
Bandara et al. (Mar. 2012), "Photoisomerization in different classes of azobenzene," Chem. Soc. Rev. 2012, 41, 1809-1825.
Beharry et al. (Sep. 2011), "Azobenzene Photoswitching without Ultraviolet Light," J. Am. Chem. Soc. 2011, 133, 19684-19687.
Beharry et al. (Aug. 2011), "Azobenzene photoswitches for biomolecules," Chem. Soc. Rev. 2011, 40, 4422-4437.
Bleger et al. (Dec. 2012), "o-Fluoroazobenzenes as Readily Synthesized Photoswitches Offering Nearly Quantitative Two-Way Isomerization with Visible Light," J. Am. Chem. Soc. 2012, 134, 20597-20600.
Bleger et al. (Jun. 2015), "Visible-Light-Activated Molecular Switches," Angew. Chem. Int. Ed. 2015, 54, 11338-11349.
Blevins et al. (Mar. 2004), "Effect of Positional Substitution on the Optical Response of Symmetrically Disubstituted Azobenzene Derivatives," J. Phys. Chem. B 2004, 108, 4962-4968.
Brieke et al. (Jul. 2012), "Light-Controlled Tools," Angew. Chem. Int. Ed. 2012, 51, 8446-8476.
Chen et al. (Feb. 2009), "Self-assembled π-stacks of functional dyes in solution: structural and thermodynamic features," Chem. Soc. Rev. 2009, 38, 564-584.
Dong et al. (Sep. 2015), "Red-Shifting Azobenzene Photoswitches for in Vivo U," Accounts. Chem. Res. 2015, 48, 2662-2670.
Finkelstein et al. (Jan. 1951), "Studies in Phenanthridine Chemistry," J. Am. Chem. Soc. 1951, 73, 302-304.
Garcia-Amoros et al. (Jul. 2012), "Recent advances towards azobenzene-based lightdriven real-time information-transmitting materials," J. Org. Chem. 2012, 8, 1003-1017.
Helmy et al. (May 2014), "Photoswitching Using Visible Light: A New Class of Organic Photochromic Molecules," J. Am. Chem. Soc. 2014, 136, 8169-8172.
International Preliminary Report on Patentability dated Mar. 10, 2016 corresponding to International Application No. PCT/US2014/052983 (7 pages).
International Search Report and Written Opinion dated Oct. 23, 2014 corresponding to International Application No. PCT/US2014/052983 (9 pages).
Irie (May 2000), "Photochromism: Memories and Switches—Introduction," Chem. Rev. 2000, 100, 1683-1684.
Kawata et al. (Apr. 2000), "Three-Dimensional Optical Data Storage Using Photochromic Materials," Chem. Rev. 2000, 100, 1777-1788.
Kay et al. (Nov. 2007), "Synthetic Molecular Motors and Mechanical Machines," Angew. Chem. Int. Ed. 2007, 46, 72-191.
Kurihara et al. (Jun. 2002), "Redox-Conjugated Reversible Isomerization of Ferrocenylazobenzene with a Single Green Light," J. Am. Chem. Soc. 2002, 124, 8800-8801.
Loudet et al. (Apr. 2008), "Functionalized $BF_2$ chelated azadipyrromethene dyes," Tetrahedron, 64(17):3642-3654, 2008.
Mustroph (1991), "Studies on UV/Vis absorption spectra of azo dyes.: Part 26.1electronic absorption spectra of 4,4'-diaminoazobenzenes," Dyes Pigm. vol. 16, Issue 3, 1991, pp. 223-230.
Mustroph, H. (1991) "Studies on the UV-vis absorption spectra of azo dyes: Part 25. 1 analysis of the fine structure of the $\pi 1 \rightarrow \pi 1^*$ band of 4'-donor-sub," Dyes Pigm. vol. 15, Issue 2, pp. 129-137.
Qian, H. et al. (Jan. 2017) Contolling the isomerization rate of an Azo-BF2 switch using aggregation, J. Am. Chem. Soc. 139:1037-1040.

(Continued)

Primary Examiner — Joseph R Kosack
(74) Attorney, Agent, or Firm — Lathrop Gage LLP

(57) ABSTRACT

Provided herein are photochromic organic compounds of Formula I or Formula II, which are useful as molecular switches capable of being triggered via a cis/trans isomerization process. Methods of using the molecular switch compounds to form photopharmaceutical compounds that may be used to provide selective spatiotemporal activation of pharmaceutical agents are also disclosed.

39 Claims, 51 Drawing Sheets

(56) References Cited

OTHER PUBLICATIONS

Qian, H. et al. (May 2017) "Visable-Light Fluorescence Photomodulation in Azo-BF2 Switches," Tetrahedron 73(33)4901-4904.

Ray et al. (Jul. 2012), "A switching cascade of hydrazone-based rotary switches through coordination-coupled proton relays," *Nature Chem.* 2012, 4, 757-762.

Remington's Pharmaceutical Sciences, 17th ed., Mack Publishing Company, Easton, Pa., 1985, p. 1418.

Sadovski et al. (Jan. 2009), "Spectral tuning of azobenzene photoswitches for biological applications," *Angew. Chem. Int. Ed.* 2009, 48, 1484-1486.

Samanta et al (Nov. 2013), "Robust visible light photoswitching with ortho-thiol substituted azobenzenes," *Chem. Comm.* 2013, 49, 10314-10316.

Samanta et al. (Jun. 2013), "Photoswitching azo compounds in vivo with red light," *J. Am. Chem. Soc.* 2013, 135, 9777-9784.

Siewertsen et al. (Oct. 2009), "Highly Efficient Reversible Z-E Photoisomerization of a Bridged Azobenzene with Visible Light through Resolved $S_1(n\pi^*)$ Absorption Bands," *J. Am. Chem. Soc.* 2009, 131, 15594-15595.

Stoddart (Jun. 2009), "The chemistry of the mechanical bond," Chem. Soc. Rev. 2009, 38, 1802-1820.

Su et al. (Aug. 2013), "Manipulating Liquid-Crystal Properties Using a pH Activated Hydrazone Switch", Angew. Chem. Int. Ed. 2013, 52, 10734-10739.

Su et al. (Jan. 2014), "Hydrazone-based switches, metallo-assemblies and sensors," Chem. Soc. Rev. 2014, 43, 1963-1981.

Szymański et al. (Apr. 2013), "Reversible Photocontrol of Biological Systems by the Incorporation of Molecular Photoswitches," Chem. Rev. 2013, 113, 6114-6178.

Tatum et al. (Apr. 2014), "Simple Hydrazone Building Blocks for Complicated Functional Materials," *Acc. Chem. Res.* 2014, 47, 2141-2149.

Wang et al. (Mar. 2016), "Theoretical study on thermal cis-to-trans isomerization of BF2-coordinated azo compounds of the para-substitution with electron donating groups," Dyes Pigments 2016, 129, 100-108.

Wegner (Mar. 2012), "Azobenzenes in a new light-switching in vivo," *Angew. Chem. Int. Ed.* 2012, 51, 4787-4788.

Yang et al. (Sep. 2012), "Visible Light Switching of BF2-Coordinated Azo Compound," J. Am. Chem. Soc., 134 (37):15221-15224, 2012.

Yang et al. (Sep. 2014), "Near-Infrared Light Activated Azo-$BF_2$ Switches," J. Am. Chem. Soc., 136(38): 13190-13193, 2014.

Yang et al. (Feb. 2012), "Aggregation-induced emission in BF2-hydrazone (BODIHY) complexes," Chem. Sci. 2012, 3, 610-613.

Zhang et al. (2013, epublished Aug. 2012), "Photochromic Materials: More Than Meets the Eye," Adv. Mater. 2013, 25, 378-399.

\* cited by examiner

Figure 1a
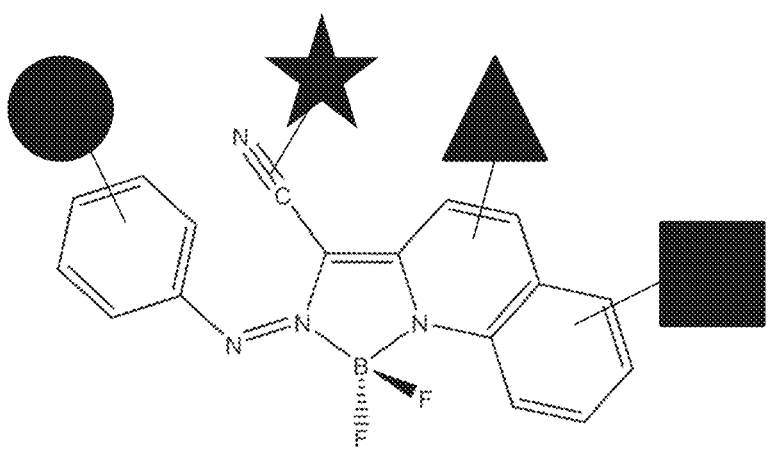
hv
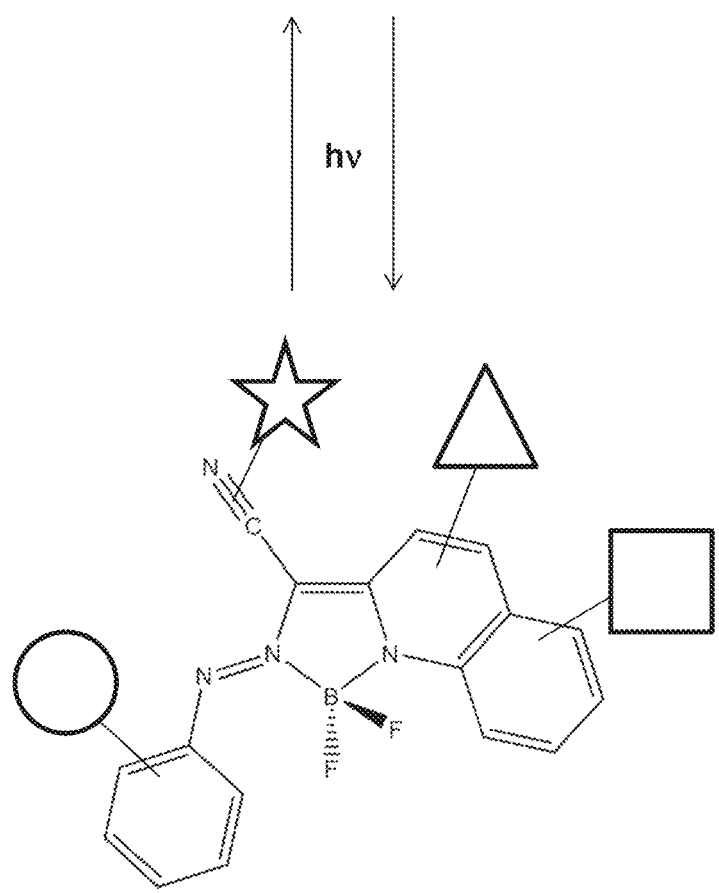

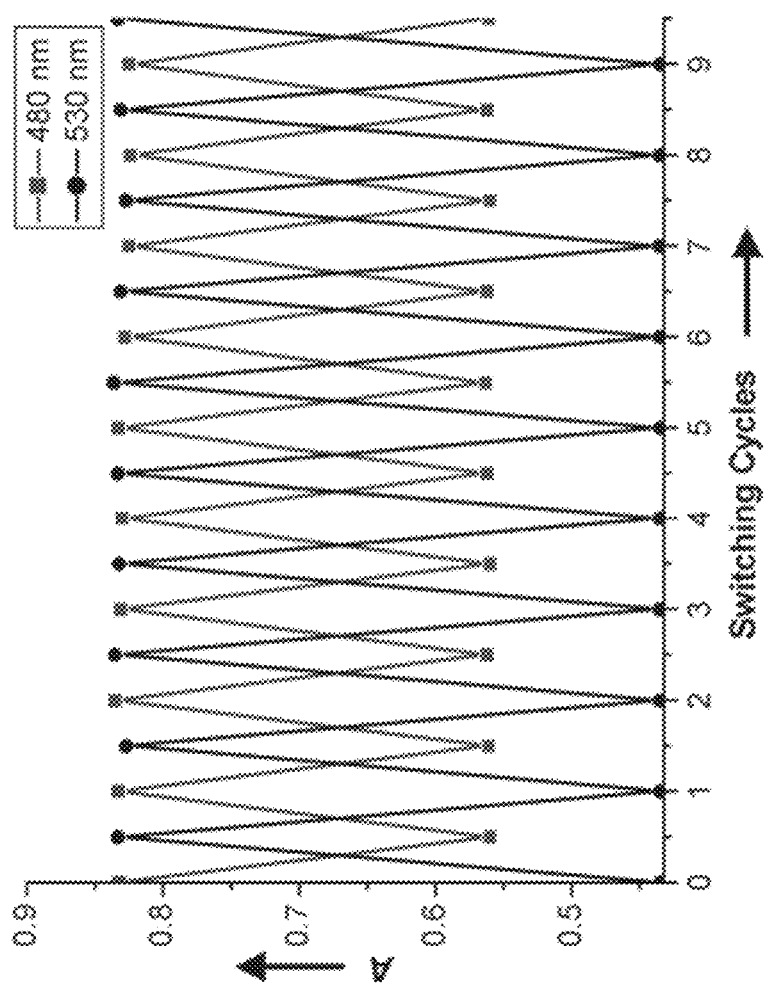

Figure 19
a)
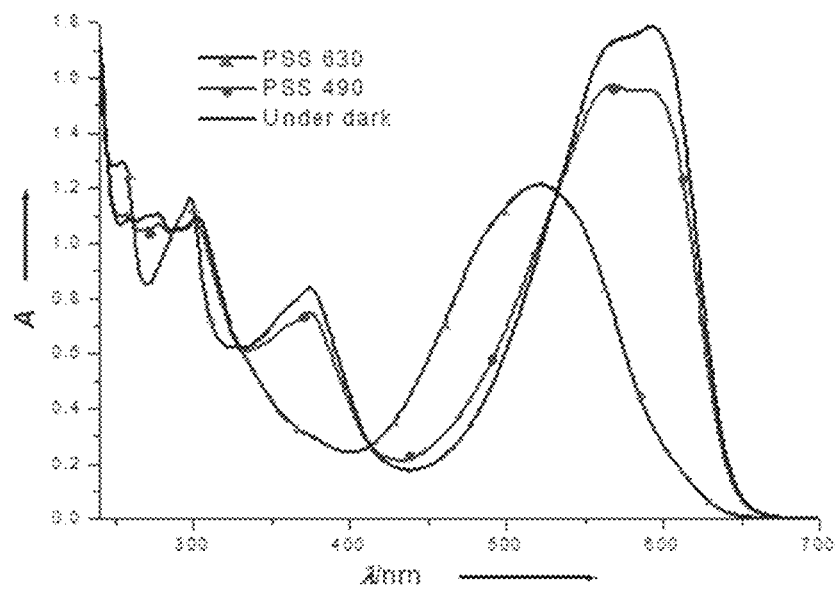
b)
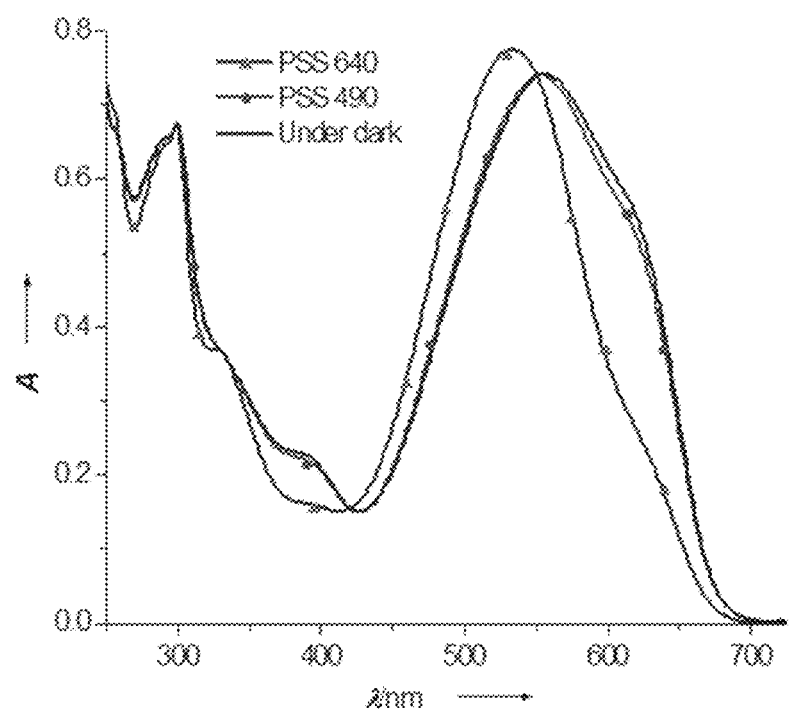

Figure 20
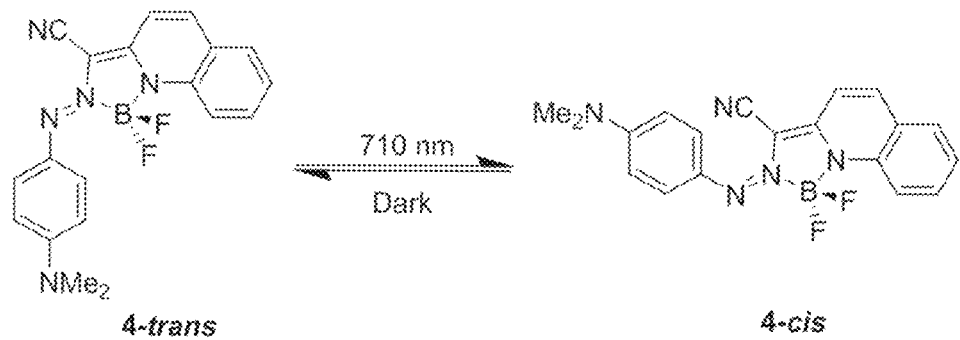
(a)
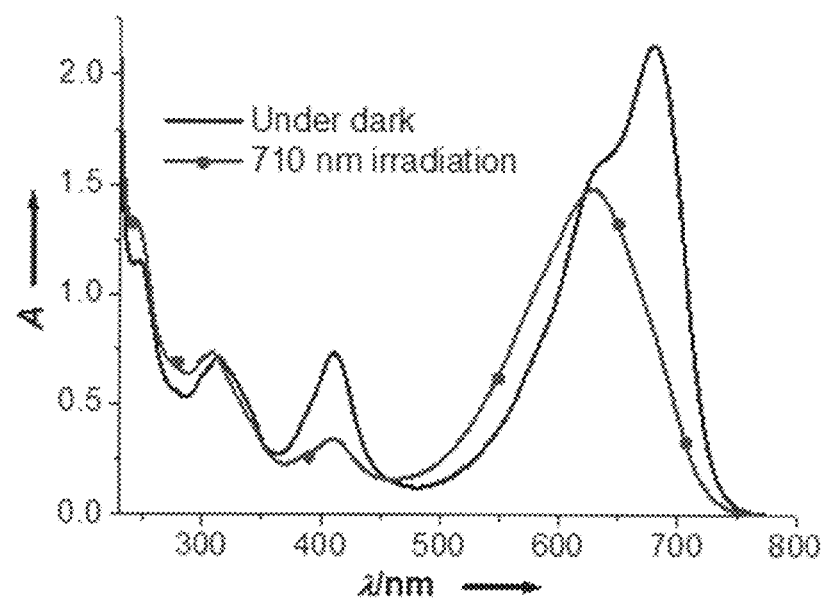
(b)

Figure 21
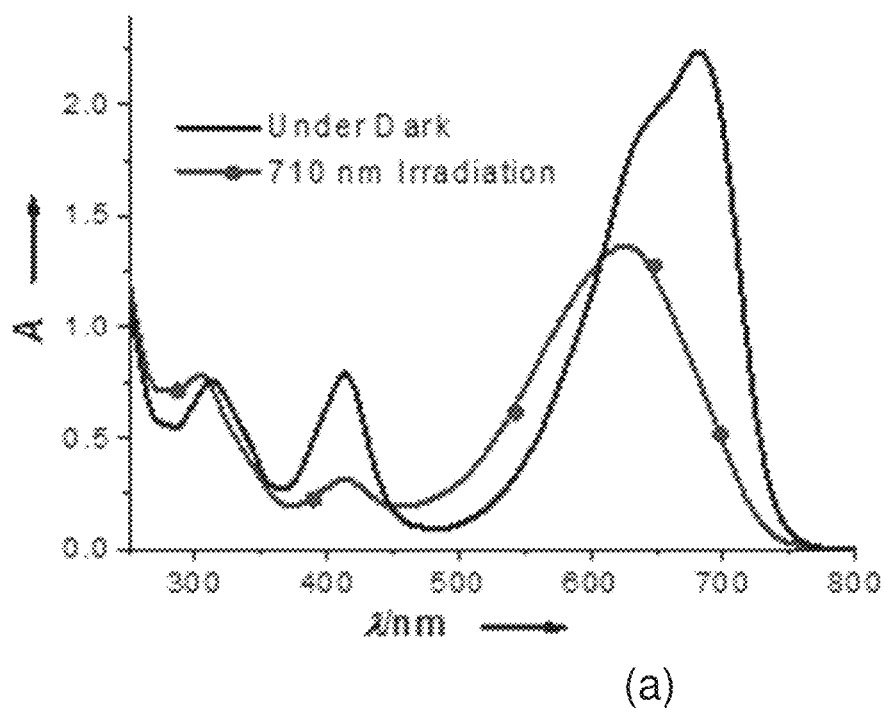
(a)
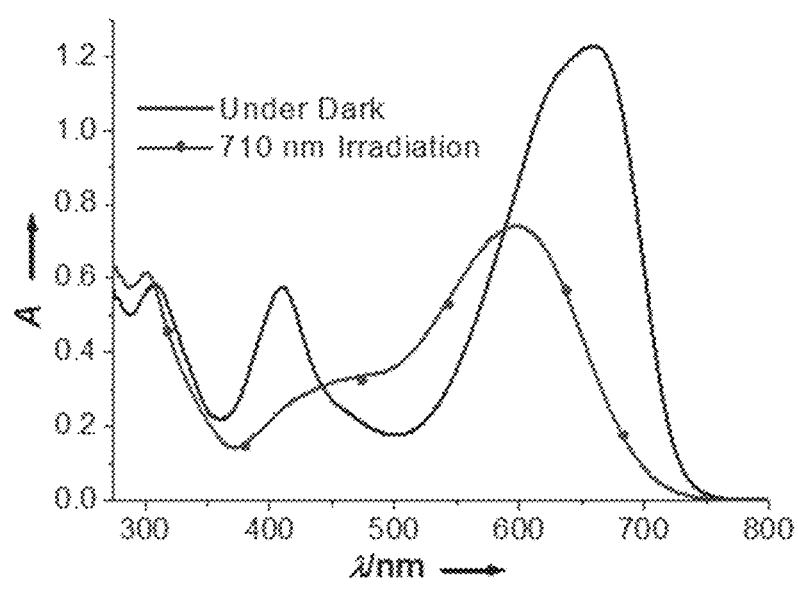
(b)

Figure 21 (cont.)
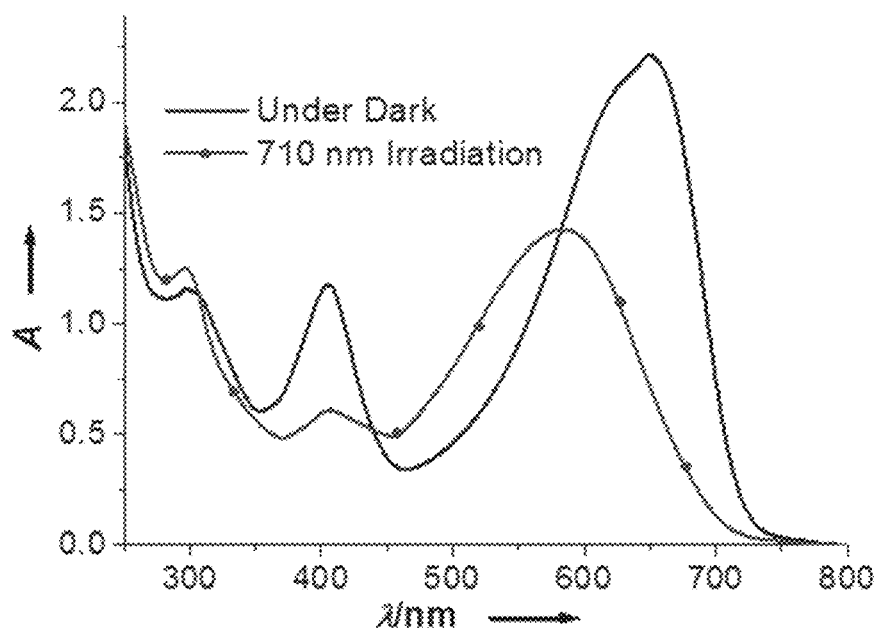
(c)
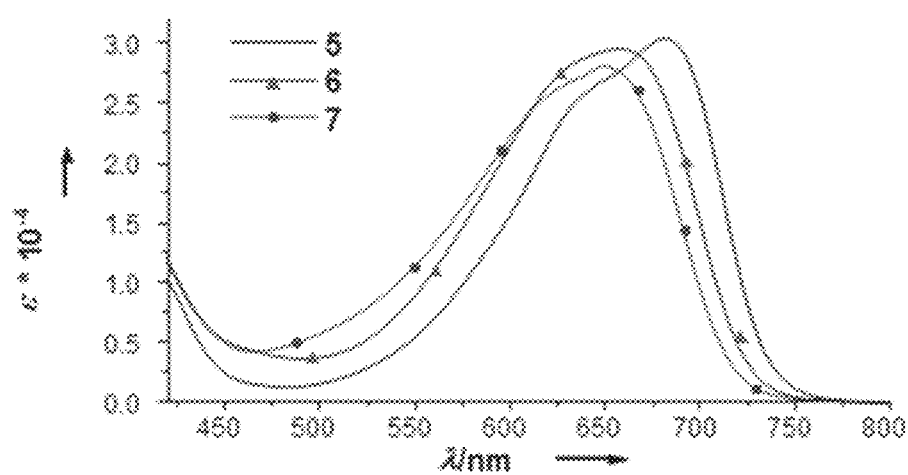
(d)

Figure 22
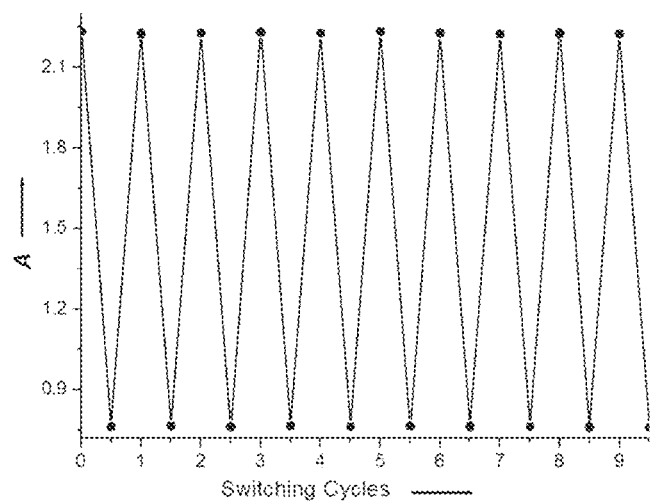
(a)
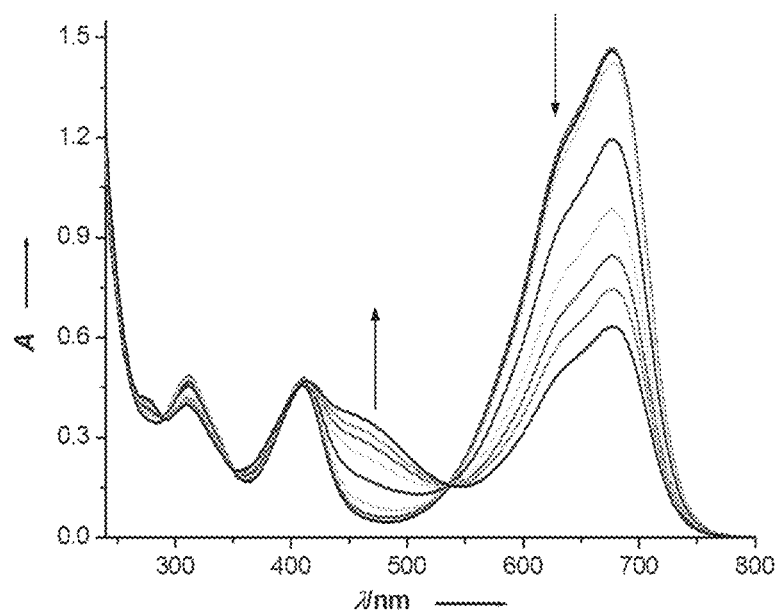
(b)

Figure 23
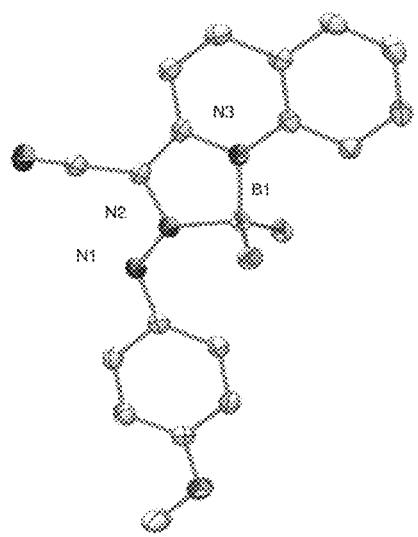
(a)
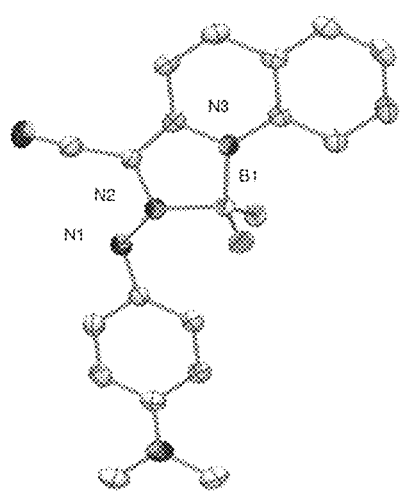
(b)

Figure 24
(a)
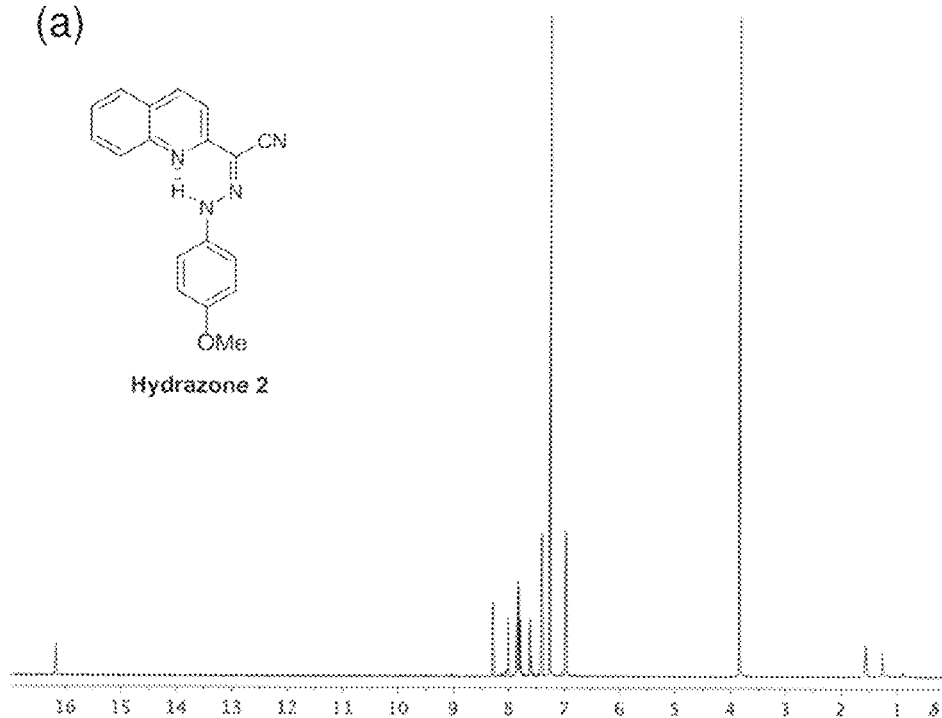
(b)
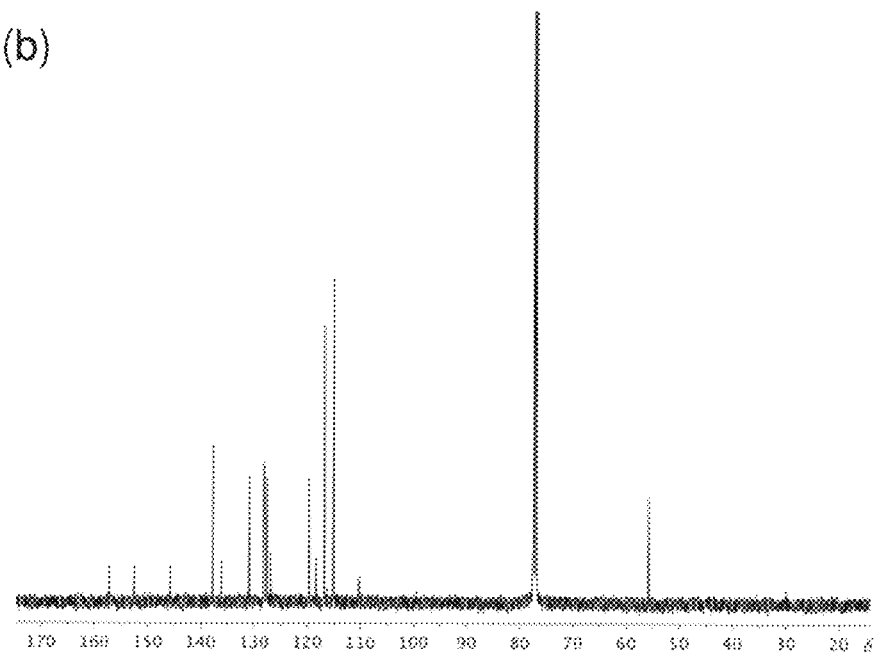

Figure 25
(a)
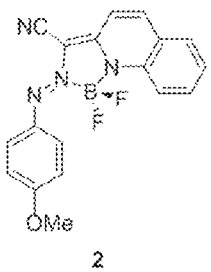
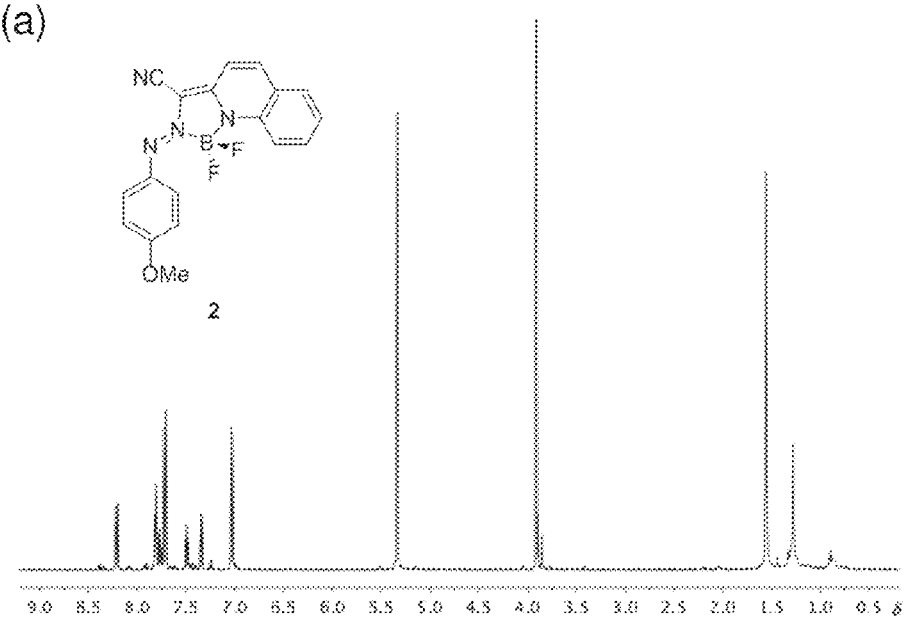
(b)
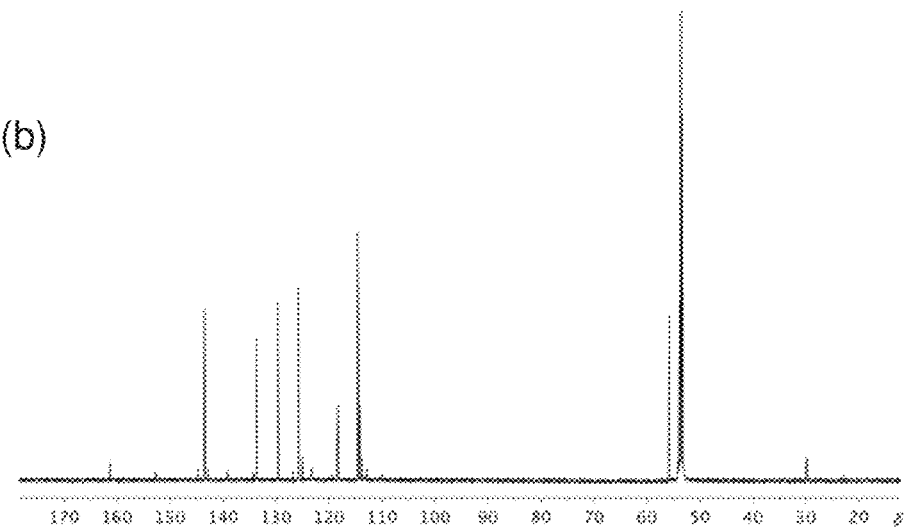
(c)
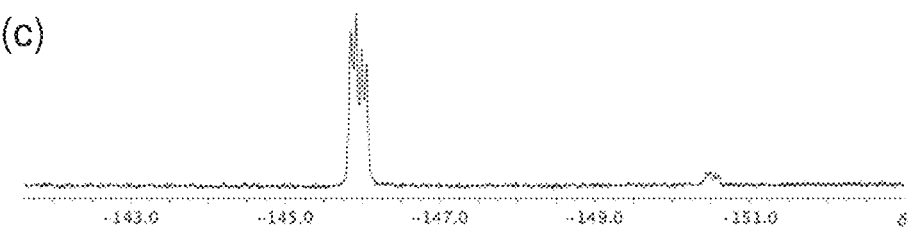

Figure 28
(a) 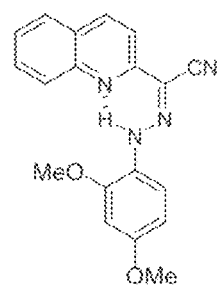
Hydrazone 3
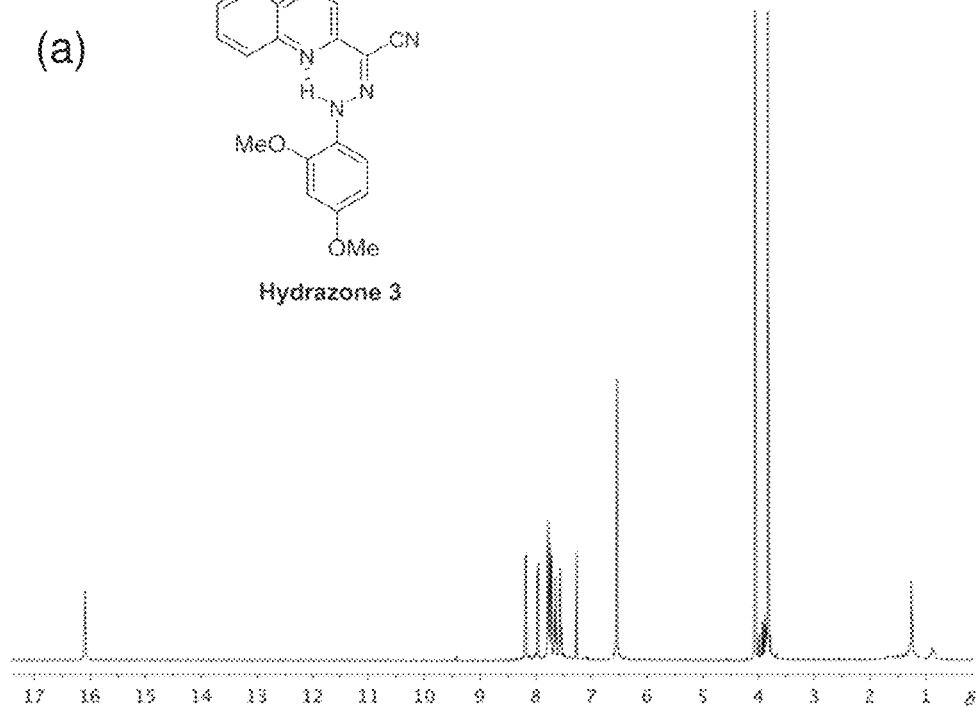
(b)
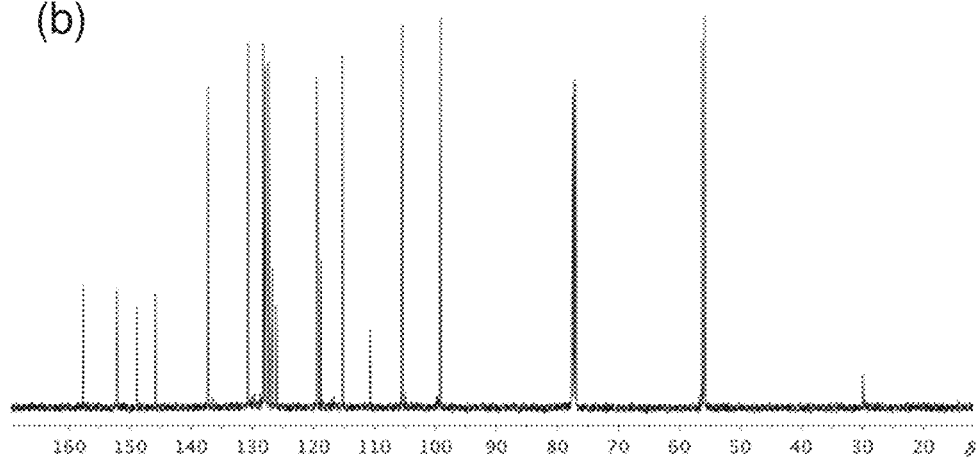

Figure 30
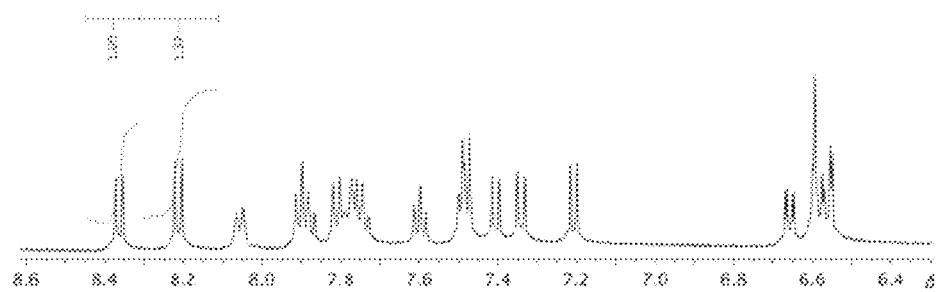
Figure 31
(a)
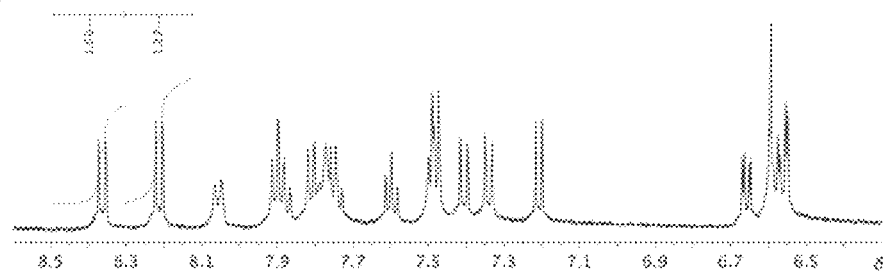
(b)
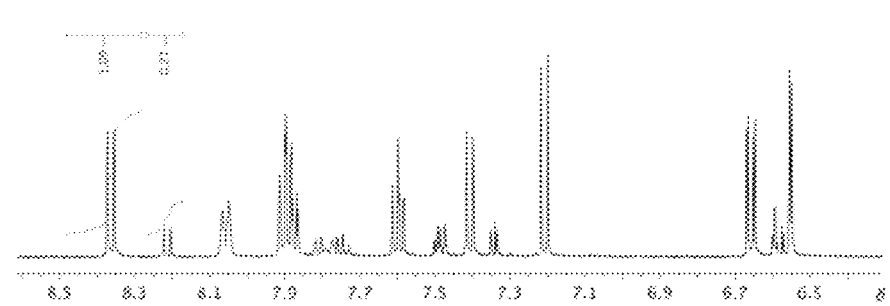

Figure 33
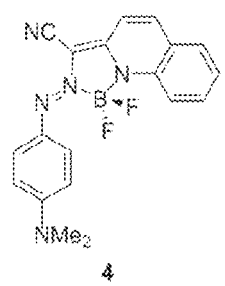
(a)
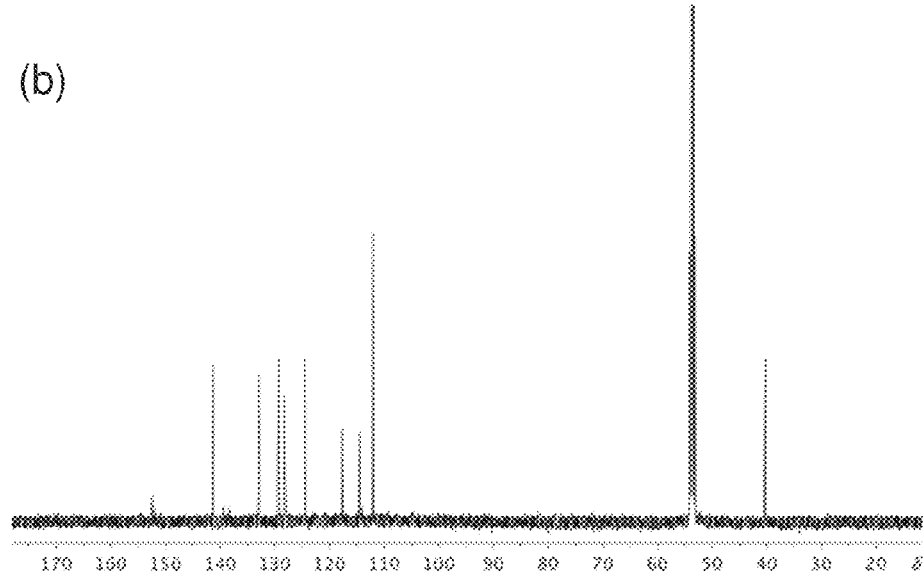
(b)
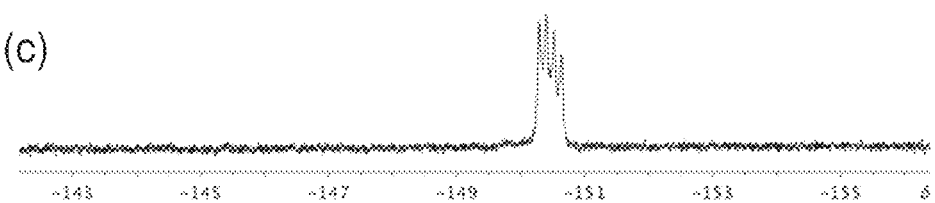
(c)

Figure 36
(a)
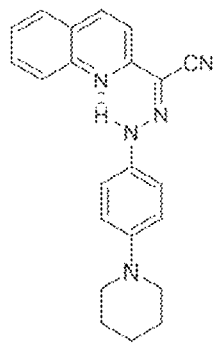
Hydrazone 5
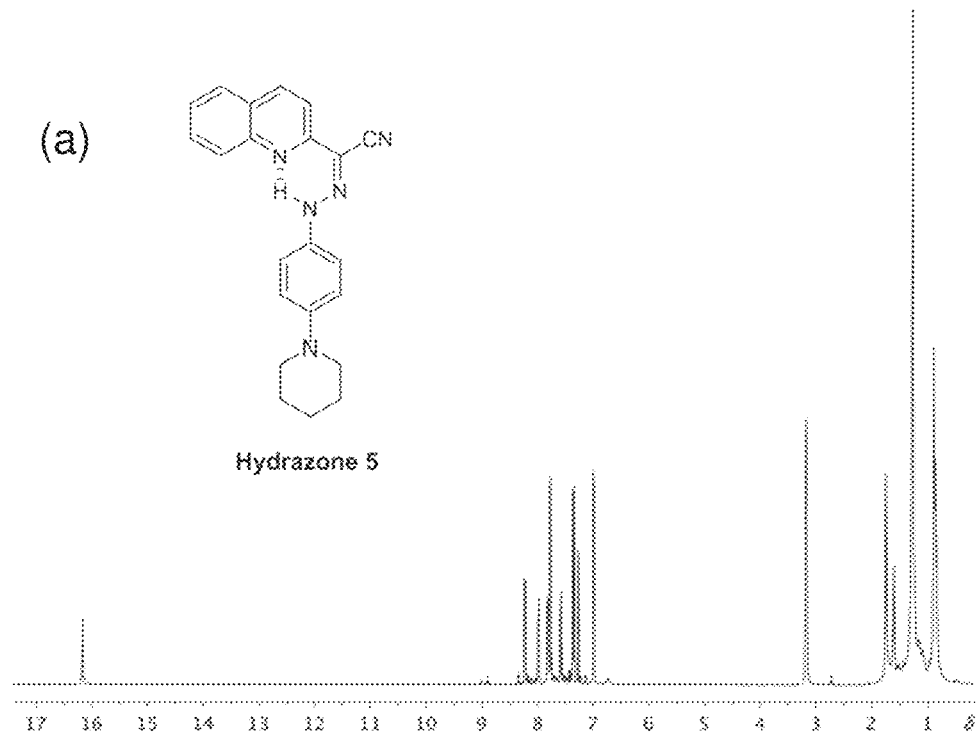
(b)
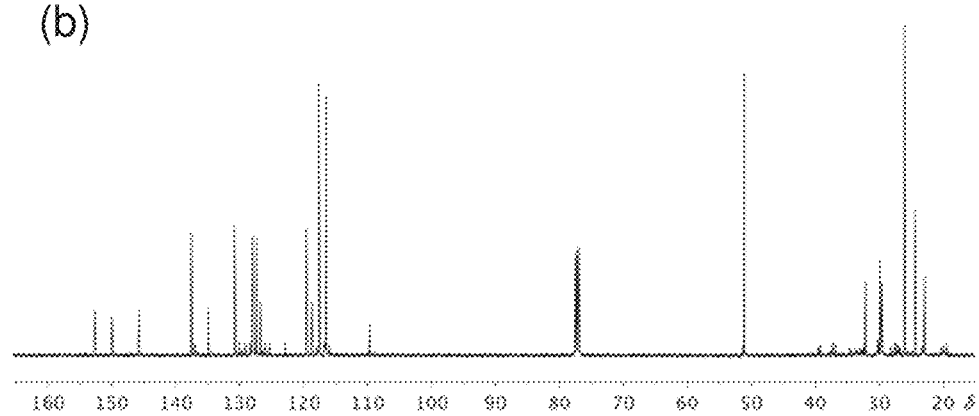

Figure 40
(a) 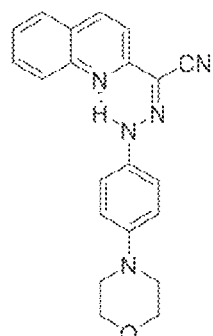
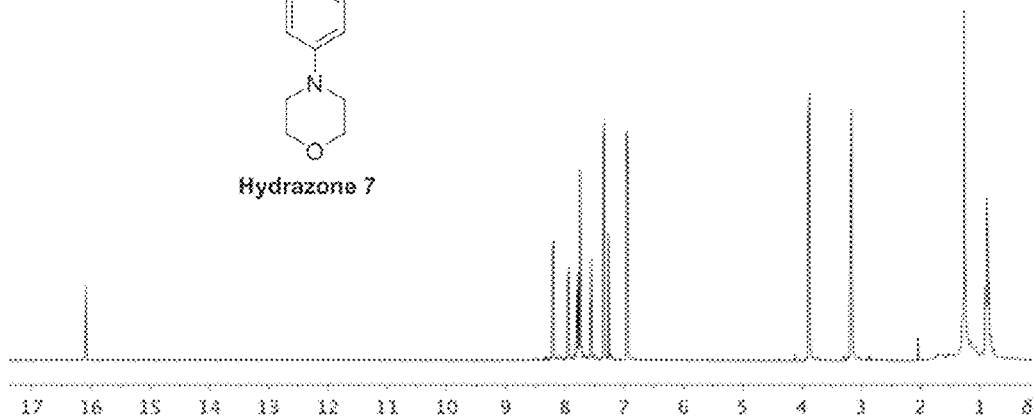
(b)
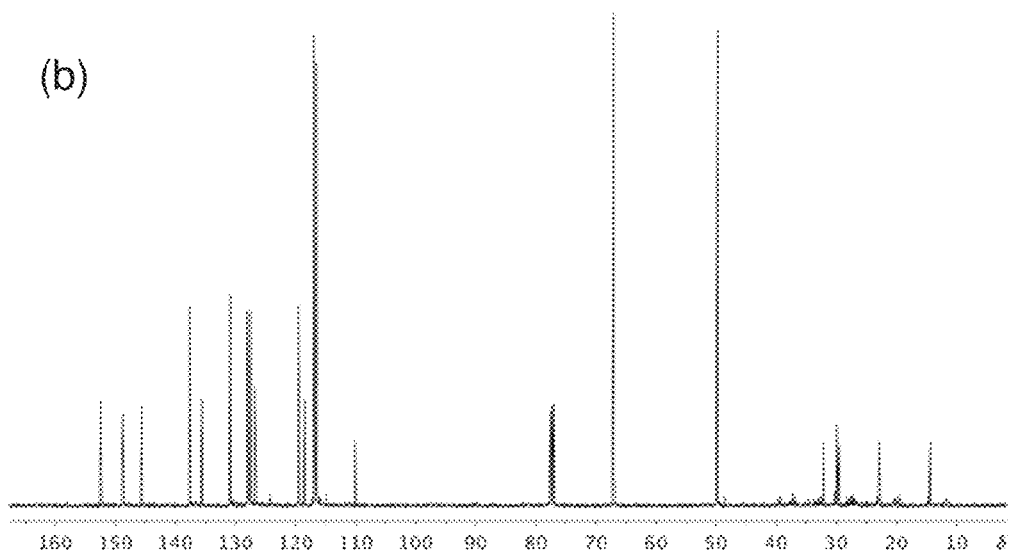

Figure 48
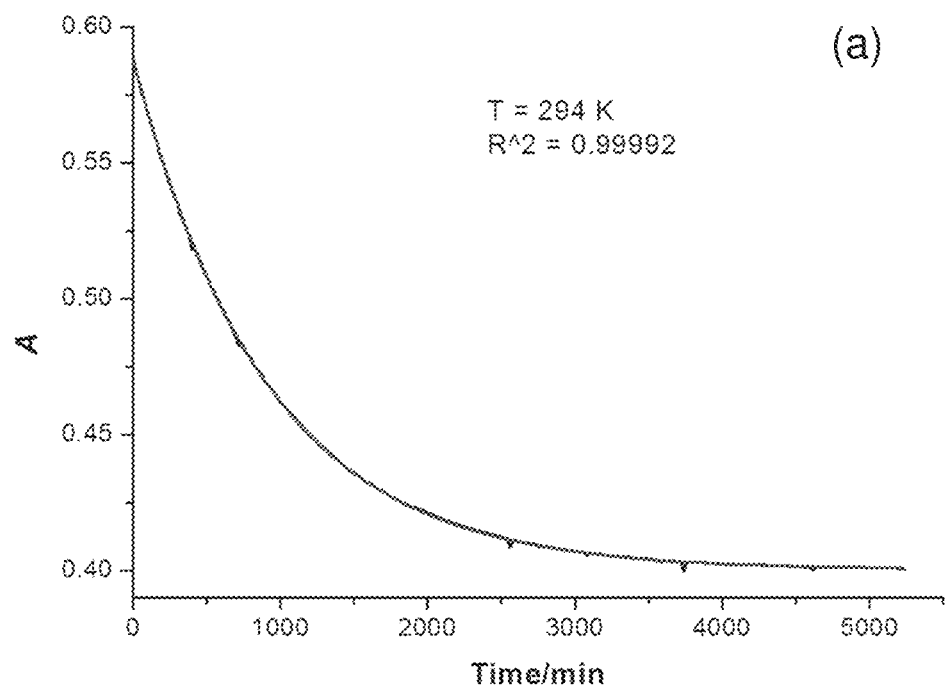
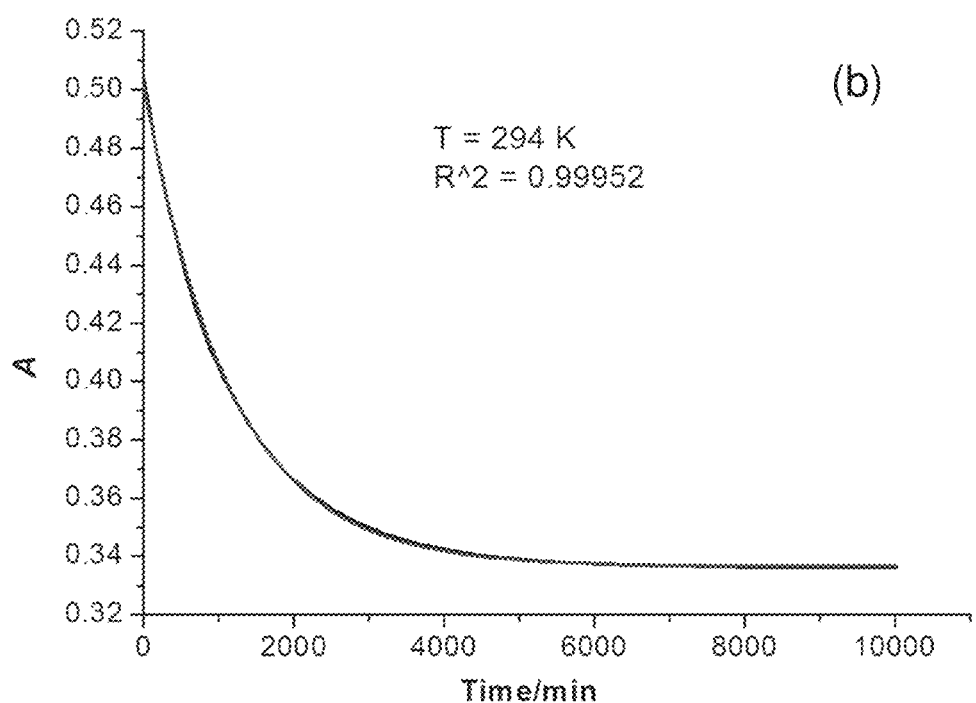

Figure 50
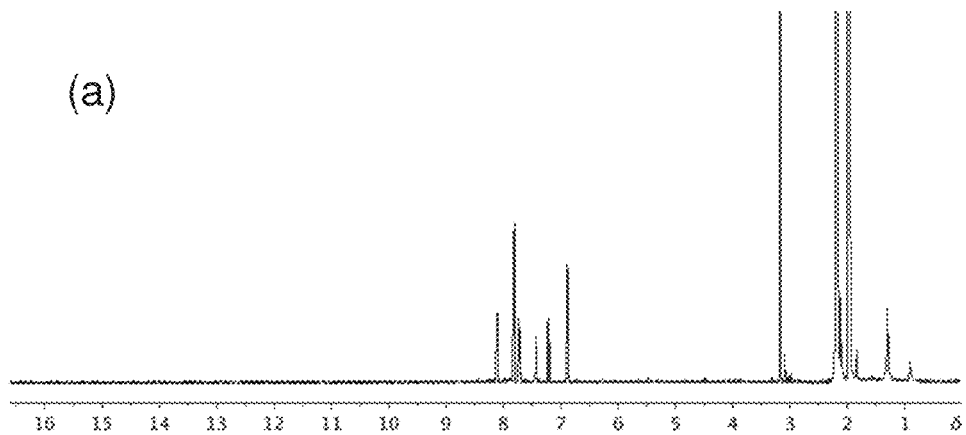
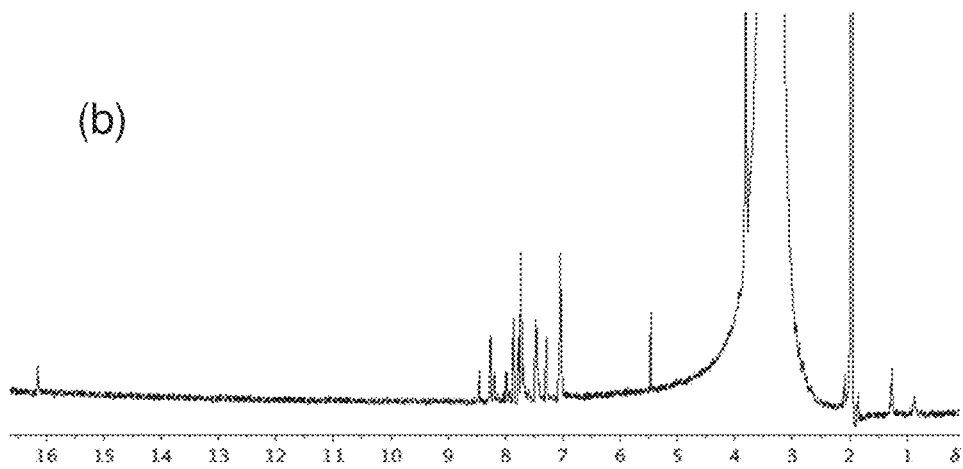
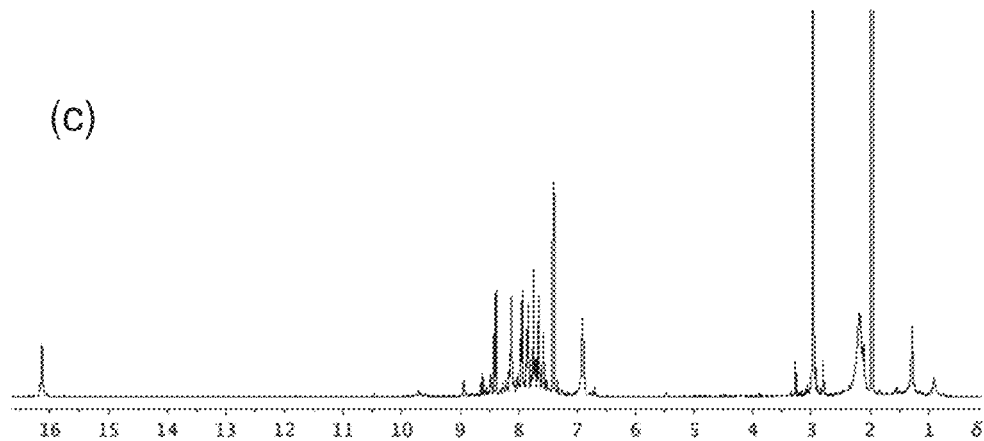

MOLECULAR SWITCHES BASED ON CIS/TRANS ISOMERIZATION OF BF2-COORDINATED AZO COMPOUNDS

CROSS-REFERENCE TO RELATED APPLICATIONS

This application is a U.S. National Stage application under 35 U.S.C. §371 of PCT/US14/52983, filed Aug. 27, 2014, which claims the benefit of priority from U.S. Provisional Patent Application No. 61/870,572, filed Aug. 27, 2013. Each of these applications is hereby incorporated by reference in its entirety.

BACKGROUND

Photoreversible, organic compounds are especially attractive materials for use as molecular switches. Photoreversible compounds are stimulated by light, i.e., they provide reversible switching processes based on photochemically induced interconversions. Photochromism, a reversible change induced by light irradiation between two states of a molecule having different electromagnetic absorption spectra, is commonly associated with such photoreversible systems. Photochromic switching processes are typically based on photocyclization of isomers, the conversion of olefinic (cis/trans) isomers, photoinduced electron transfer, and keto-enol tautomerism.

Photochromic molecular switches based on the trans→cis isomerization of azobenzene are useful for many purposes, including industrial dyes, actuators, nonlinear optical devices, liquid crystals, molecular machines, ion channel modulators, and the like. Ultraviolet (UV) light often is used to induce the trans→cis isomerization. However, UV light can be harmful in certain applications, especially those involving in vivo systems. Hence, there is a significant need in the art for photochromic molecular switches that can be toggled between cis and trans states using lower energy electromagnetic irradiation with less scattering and that can penetrate tissues more easily (i.e., red and NIR light).

SUMMARY OF THE INVENTION

Provided herein are compounds, photochromic materials comprising such compounds, and methods of using such compounds as molecular switches. In an embodiment, the compounds may be used in photopharmaceutical compounds as molecular switches that allow for selective spatiotemporal activation of pharmaceutical agents.

Accordingly, in one aspect, provided herein is a compound of Formula II:

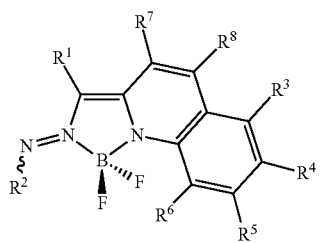

(II)

or a salt thereof, wherein
N═N—$R^2$ can be oriented cis or trans to the tricycle;
$R^1$ is H, CN, $CO_2H$, $CO_2(C_{1-6}$-alkyl), $C_{1-6}$-alkyl, $C_{6-19}$-aryl, OH, $O(C_{1-6}$-alkyl), $OC(O)(C_{1-6}$-alkyl), $NH_2$, $NH(C_{1-6}$-alkyl), $N(C_{1-6}$-alkyl)$_2$, or $NHC(O)(C_{1-6}$-alkyl);
$R^2$ is $C_{6-19}$-aryl or $C_{3-14}$-heteroaryl, wherein the $C_{6-19}$-aryl or $C_{3-14}$-heteroaryl is independently substituted one or more times at the para and/or ortho position with $C_{1-6}$-alkyl, $C_{6-19}$-aryl, $C_{3-14}$-heteroalkyl, OH, $O(C_{1-6}$-alkyl), $OC(O)(C_{1-6}$-alkyl), $NH_2$, $NH(C_{1-6}$-alkyl), $N(C_{1-6}$-alkyl)$_2$, or $NHC(O)(C_{1-6}$-alkyl); and
$R^3$, $R^4$, $R^5$, $R^6$, $R^7$ and $R^8$ are each, independently, H, $C_{1-6}$-alkyl, $C_{6-19}$-aryl, OH, $O(C_{1-6}$-alkyl), $OC(O)(C_{1-6}$-alkyl), $NH_2$, $NH(C_{1-6}$-alkyl), $N(C_{1-6}$-alkyl)$_2$, $NHC(O)(C_{1-6}$-alkyl) or a group corresponding to a small molecule pharmaceutical; or
$R^3$ and $R^4$, $R^4$ and $R^5$, $R^5$ and $R^6$ or $R^7$ and $R^8$ can, when taken together, form a fused aryl, fused heteroaryl, fused $C_{3-6}$-cycloalkyl, or fused heterocycle, wherein the fused aryl, fused heteroaryl, fused cycloalkyl, or fused heterocycle can be optionally substituted one or more times with $C_{1-6}$-alkyl, $C_{6-19}$-aryl, OH, $O(C_{1-6}$-alkyl), $OC(O)(C_{1-6}$-alkyl), $NH_2$, $NH(C_{1-6}$-alkyl), $N(C_{1-6}$-alkyl)$_2$, or $NHC(O)(C_{1-6}$-alkyl).

In another aspect, provided herein is a compound of the Formula I:

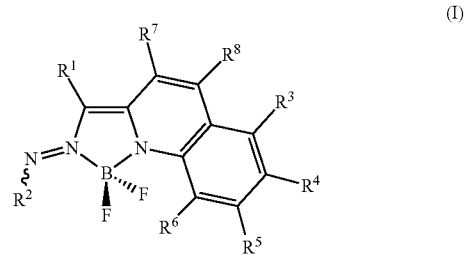

(I)

or a salt thereof, wherein
N═N—$R^2$ can be oriented cis or trans to the tricycle;
$R^1$ is H, CN, $CO_2H$, $CO_2(C_{1-6}$-alkyl), $C_{1-6}$-alkyl, $C_{6-19}$-aryl, OH, $O(C_{1-6}$-alkyl), $OC(O)(C_{1-6}$-alkyl), $NH_2$, $NH(C_{1-6}$-alkyl), $N(C_{1-6}$-alkyl)$_2$, or $NHC(O)(C_{1-6}$-alkyl);
$R^2$ is unsubstituted $C_{6-19}$-aryl or unsubstituted $C_{3-14}$-heteroaryl; and
$R^3$, $R^4$, $R^5$, $R^6$, $R^7$ and $R^8$ are each, independently, H, $C_{1-6}$-alkyl, $C_{6-19}$-aryl, OH, $O(C_{1-6}$-alkyl), $OC(O)(C_{1-6}$-alkyl), $NH_2$, $NH(C_{1-6}$-alkyl), $N(C_{1-6}$-alkyl)$_2$, $NHC(O)(C_{1-6}$-alkyl) or a group corresponding to a small molecule pharmaceutical; or
$R^3$ and $R^4$, $R^4$ and $R^5$, $R^5$ and $R^6$ or $R^7$ and $R^8$ can, when taken together, form a fused aryl, fused heteroaryl, fused $C_{3-6}$-cycloalkyl, or fused heterocycle, wherein the fused aryl, fused heteroaryl, fused cycloalkyl, or fused heterocycle can be optionally substituted one or more times with $C_{1-6}$-alkyl, $C_{6-19}$-aryl, OH, $O(C_{1-6}$-alkyl), $OC(O)(C_{1-6}$-alkyl), $NH_2$, $NH(C_{1-6}$-alkyl), $N(C_{1-6}$-alkyl)$_2$, or $NHC(O)(C_{1-6}$-alkyl).

In certain embodiments of Formula I and Formula II, $R^3$, $R^4$, $R^5$, $R^6$, $R^7$ and $R^8$ are each, independently, H.

In certain other embodiments of Formula I and Formula II, $R^1$ is CN.

In certain embodiments of Formula I, $R^2$ is unsubstituted phenyl.

In certain embodiments of Formula II, $R^2$ is phenyl, wherein the phenyl is substituted at the para position. In certain other embodiments of Formula II, $R^2$ is phenyl, wherein the phenyl is substituted at the para position with $N(CH_3)_2$, $OCH_3$, piperazinyl, (N-methyl)piperazinyl, piperidinyl, morpholinyl or a group corresponding to a cholesterol molecule.

In some embodiments of Formula I and Formula II, $N=N-R^2$ is oriented cis to the tricycle. In other embodiments of Formula I and Formula II, $N=N-R^2$ is oriented trans to the tricycle.

In certain embodiments of Formula I and Formula II, $R^3$, $R^4$, $R^5$, $R^6$, $R^7$ and $R^8$ are each, independently, a bond to a pharmaceutical agent.

In one aspect, provided herein is a photochromic molecular switch comprising at least one compound of Formula I or a salt thereof. In another aspect, provided herein is a photochromic molecular switch comprising at least one compound of Formula II or a salt thereof.

In yet another aspect, provided herein is a method of switching a molecular switch, wherein the molecular switch comprises a compound of Formula I or a salt thereof; wherein the method comprises applying electromagnetic radiation to the molecular switch at a first wavelength effective to cause the trans→cis isomerization of the compound of Formula I or salt thereof; or applying electromagnetic radiation to the molecular switch at a second wavelength effective to cause the cis→trans isomerization of the compound of Formula I or salt thereof; or a combination thereof.

In still another aspect, provided herein is a method of switching a molecular switch, wherein the molecular switch comprises a compound of Formula II or a salt thereof; wherein the method comprises applying electromagnetic radiation to the molecular switch at a first wavelength effective to cause the trans→cis isomerization of the compound of Formula II or salt thereof; or applying electromagnetic radiation to the molecular switch at a second wavelength effective to cause the cis→trans isomerization of the compound of Formula II or salt thereof; or a combination thereof.

In certain embodiments, the molecular switch comprising the salt of Formula I or the salt of Formula II is reacted with a pharmaceutically acceptable salt to form a photopharmaceutical compound. In certain embodiments, the pharmaceutically acceptable salt is a salt of a small molecule pharmaceutical.

In one embodiment, the molecular switch comprising the compound of Formula I or the compound of Formula II or a photopharmaceutical compound thereof is stable in water or biological fluid. In another embodiment, the molecular switch comprising the compound of Formula I or the compound of Formula II or a photopharmaceutical compound thereof does not substantially hydrolyze in water or biological fluid.

In certain embodiments, a method of treating a patient in need of therapy comprises administering a therapeutically effective amount of a photopharmaceutical compound to a patient in need thereof; and applying electromagnetic radiation to a tissue comprising the photopharmaceutical compound at a first wavelength effective to cause the trans→cis isomerization or applying electromagnetic radiation to the photopharmaceutical compound at a second wavelength effective to cause the cis→trans isomerization or a combination thereof.

In one embodiment of the methods of switching the molecular switch, the electromagnetic radiation is generated by an infrared light source and/or a visible light source.

In another embodiment of the methods of switching the molecular switch, the electromagnetic radiation is generated by a visible light source.

BRIEF DESCRIPTION OF THE FIGURES

FIG. 1a schematically illustrates a photopharmaceutical compound comprising a pharmaceutical agent (circle, star, triangle, square) bound to Compound 1, where activation of the pharmaceutical agent is triggered by isomerization of Compound 1.

FIG. 1c shows multiple isomerization cycles of Compound 1 (0.1 mM) in $CH_2Cl_2$ (not deoxygenated) after alternative irradiation at $\lambda_1$=570 nm (red trace) and $\lambda_2$=450 nm (black trace).

FIG. 19 (a) The UV/Vis spectral changes upon the photoisomerization of 2 in $CH_2Cl_2$ (0.2 mM). The black trace is of 2 equilibrated under dark (mainly trans), which upon irradiation at λ=630 nm gives the cis PSS (blue trace). Irradiating the latter at λ=490 nm gives the trans PSS (red trace). (b) The UV/Vis spectral changes upon the photoisomerization of 3 in $CH_2Cl_2$ (0.1 mM). The black trace is of 3 equilibrated under dark, which upon irradiation at λ=640 nm gives the cis PSS (blue trace). Irradiating the latter at λ=490 nm gives the trans PSS (red trace).

FIG. 20. (a) NIR light-induced trans/cis isomerization of 4. (b) The UV/Vis spectral changes upon the photoisomerization of 4 in $CH_2Cl_2$ (0.2 mM). The black trace is of 4 equilibrated under dark (mainly trans), which upon irradiation at λ=710 nm gives the cis populated state (red trace).

FIG. 21. UV/Vis spectral changes upon photoisomerization of (a) 5, (b) 6 and (c) 7. The black trace is equilibrated complex in the dark (mainly trans), which upon irradiation at λ=710 nm gives the cis populated state (red trace); (d) Overlay of the π-π* absorption bands of the trans isomers of 5-7, represented by black, blue and red lines, respectively.

FIG. 22. (a) Switching cycles of 4 in acetonitrile:PBS buffer (1:1) monitored by following the absorbance at λ=681 nm (black trace) upon irradiation at λ=710 nm then leaving in the dark. (b) UV/Vis spectra following an acetonitrile:PBS buffer (1:1) solution of the azo-$BF_2$ complex 4 at 25° C. The interval between each scan is 20 min.

FIG. 23. ORTEP drawing (50% probability ellipsoids) of the crystal structures of (a) 2 and (b) 4. The hydrogen atoms were removed for clarity.

FIG. 24. a) $^1H$ NMR and b) $^{13}C$ NMR spectra of Hydrazone 2 (contains a small percentage of the Z isomer) in $CDCl_3$ at 294 K.

FIG. 25. a) $^1H$ NMR b) $^{13}C$ NMR and c) $^{19}F$ NMR spectra of 2-trans (contains a small percentage of the cis isomer) in $CD_2Cl_2$ at 294 K.

FIG. 28. a) $^1H$ NMR and b) $^{13}C$ NMR spectra of Hydrazone 3 (contains a small percentage of the Z isomer) in $CDCl_3$ at 294 K.

FIG. 30. $^1H$ NMR spectrum of 3 after being stored in the dark. The equilibrated mixture of 3 was determined to have an isomer ratio of 58:42 (trans:cis).

FIG. 31. $^1H$ NMR spectra of the PSS of 3 at a) 490 nm and b) 640 nm in $CD_2Cl_2$ at 294 K. The PSS isomer ratios of 56±1% trans at $\lambda_{irr}$=490 nm, and 79±1% cis at $\lambda_{irr}$=640 nm are the averages of three experiments.

FIG. 33. a) $^1H$ NMR b) $^{13}C$ NMR and c) $^{19}F$ NMR spectra of 4-trans in $CD_2Cl_2$ at 294 K.

FIG. 36. a) $^1H$ NMR and b) $^{13}C$ NMR spectra of Hydrazone 5 (contains a small percentage of the Z isomer) in $CDCl_3$ at 294 K.

FIG. 40. a) $^1H$ NMR and b) $^{13}C$ NMR spectra of Hydrazone 7 (contains a small percentage of the Z isomer) in $CDCl_3$ at 294 K.

FIG. 48. Plots of Absorbance versus time showing the first-order decays of (a) 2 and (b) 3 in degassed $CH_2Cl_2$ at 294 K starting from PSS630 and PSS640, respectively. The black lines represent the experimental results while the red lines represent the theoretical first-order fits.

FIG. 50. $^1H$ NMR spectra of a) 4 in $CD_3CN$, b) 4 with water in $CD_3CN$ and c) Hydrazone 4 in $CD_3CN$ at 294 K.

DETAILED DESCRIPTION OF THE INVENTION

Photochromic Compounds of the Invention

Figure 1B:
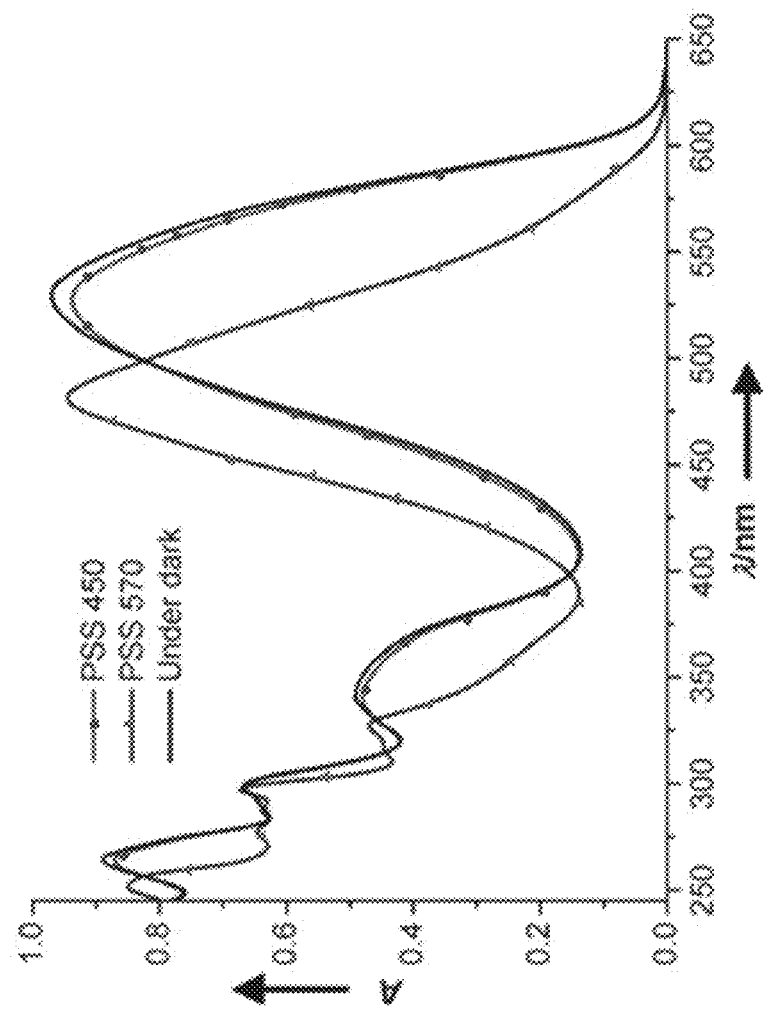
FIG. 1b shows the UV/vis spectral changes upon the photoisomerization of Compound 1 in deoxygenated $CH_2Cl_2$ (0.1 mM). The black trace is of Compound 1 equilibrated in the dark (mainly trans), which upon irradiation at $\lambda_1$=570 nm gives the cis photostationary state (PSS, blue trace), which when irradiated at $\lambda_2$=450 nm gives the trans PSS (red trace).

Provided herein are compounds for use as photochromic molecular switches. In an embodiment, the compounds may be used in photopharmaceutical compounds as molecular switches that allow for selective spatiotemporal activation of pharmaceutical agents. As illustrated in FIG. 1a, one or more pharmaceutical agents (generically depicted as circles, stars, triangles and squares) may be bound to Compound 1 and activated by isomerization of Compound 1. Activation is schematically illustrated in FIG. 1a as a change from a filled shape (e.g., circle, star, triangle, square) to an unfilled shape or vice versa. Activation may, for example, include formation or breaking of one or more chemical bonds, severing of the molecular switch and pharmaceutical agent moieties, a change in configuration of the molecule to increase or decrease steric and/or electronic interactions (e.g., between the pharmaceutical agent and a protein binding pocket), a transfer of charge to/from/within the pharmaceutical agent, photon absorption or emission by the pharmaceutical agent, and/or any other process that changes the pharmaceutical agent from a first state to a second state, wherein the pharmaceutical agent in the first state does not alter a biological material or process, and wherein the pharmaceutical agent in the second state alters a biological material or process.

Also provided herein are methods of switching a molecular switch wherein electromagnetic radiation is applied to the molecular switch at a first wavelength effective to cause the trans→cis isomerization of a compound of Formula I or Formula II, a salt of Formula I or Formula II, or a photopharmaceutical compound derived from Formula I or Formula II; or applying electromagnetic radiation to the molecular switch at a second wavelength effective to cause the cis→trans isomerization of a compound of Formula I or Formula II, a salt of Formula I or Formula II, or a photopharmaceutical compound derived from Formula I or Formula II; or a combination thereof.

In one aspect, provided herein are compounds of Formula II:

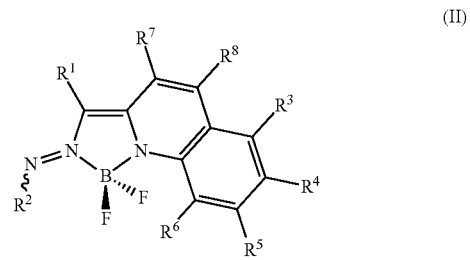

(II)

or a salt thereof, wherein $N=N-R^2$ can be oriented cis or trans to the tricycle;

$R^1$ is H, CN, $CO_2H$, $CO_2(C_{1-6}$-alkyl), $C_{1-6}$-alkyl, $C_{6-19}$-aryl, OH, $O(C_{1-6}$-alkyl), $OC(O)(C_{1-6}$-alkyl), $NH_2$, $NH(C_{1-6}$-alkyl), $N(C_{1-6}$-alkyl)$_2$, or $NHC(O)(C_{1-6}$-alkyl);

$R^2$ is $C_{6-19}$-aryl or $C_{3-14}$-heteroaryl, wherein the $C_{6-19}$-aryl or $C_{3-14}$-heteroaryl is independently substituted one or more times at the para and/or ortho position with $C_{1-6}$-alkyl, $C_{6-19}$-aryl, $C_{3-14}$-heteroalkyl, OH, $O(C_{1-6}$-alkyl), $OC(O)(C_{1-6}$-alkyl), $NH_2$, $NH(C_{1-6}$-alkyl), $N(C_{1-6}$-alkyl)$_2$, or $NHC(O)(C_{1-6}$-alkyl); and $R^3$, $R^4$, $R^5$, $R^6$, $R^7$ and $R^8$ are each, independently, H, $C_{1-6}$-alkyl, $C_{6-19}$-aryl, OH, $O(C_{1-6}$-alkyl), $OC(O)(C_{1-6}$-alkyl), $NH_2$, $NH(C_{1-6}$-alkyl), $N(C_{1-6}$-alkyl)$_2$, $NHC(O)(C_{1-6}$-alkyl) or a group corresponding to a small molecule pharmaceutical; or $R^3$ and $R^4$, $R^4$ and $R^5$, $R^5$ and $R^6$ or $R^7$ and $R^8$ can, when taken together, form a fused aryl, fused heteroaryl, fused $C_{3-6}$-cycloalkyl, or fused heterocycle, wherein the fused aryl, fused heteroaryl, fused cycloalkyl, or fused heterocycle can be optionally substituted one or more times with $C_{1-6}$-alkyl, $C_{6-19}$-aryl, OH, $O(C_{1-6}$-alkyl), $OC(O)(C_{1-6}$-alkyl), $NH_2$, $NH(C_{1-6}$-alkyl), $N(C_{1-6}$-alkyl)$_2$, or $NHC(O)(C_{1-6}$-alkyl).

In another aspect, provided herein is a compound of the Formula I:

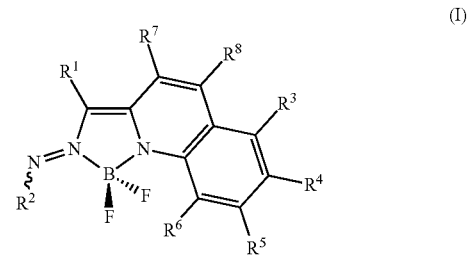

(I)

or a salt thereof, wherein $N=N-R^2$ can be oriented cis or trans to the tricycle;

$R^1$ is H, CN, $CO_2H$, $CO_2(C_{1-6}$-alkyl), $C_{1-6}$-alkyl, $C_{6-19}$-aryl, OH, $O(C_{1-6}$-alkyl), $OC(O)(C_{1-6}$-alkyl), $NH_2$, $NH(C_{1-6}$-alkyl), $N(C_{1-6}$-alkyl)$_2$, or $NHC(O)(C_{1-6}$-alkyl);

R² is unsubstituted $C_{6-19}$-aryl or unsubstituted $C_{3-14}$-heteroaryl; and

R³, R⁴, R⁵, R⁶, R⁷ and R⁸ are each, independently, H, $C_{1-6}$-alkyl, $C_{6-19}$-aryl, OH, $O(C_{1-6}$-alkyl), $OC(O)(C_{1-6}$-alkyl), $NH_2$, $NH(C_{1-6}$-alkyl), $N(C_{1-6}$-alkyl)$_2$, $NHC(O)(C_{1-6}$-alkyl) or a group corresponding to a small molecule pharmaceutical; or R³ and R⁴, R⁴ and R⁵, R⁵ and R⁶ or R⁷ and R⁸ can, when taken together, form a fused aryl, fused heteroaryl, fused $C_{3-6}$-cycloalkyl, or fused heterocycle, wherein the fused aryl, fused heteroaryl, fused cycloalkyl, or fused heterocycle can be optionally substituted one or more times with $C_{1-6}$-alkyl, $C_{6-19}$-aryl, OH, $O(C_{1-6}$-alkyl), $OC(O)(C_{1-6}$-alkyl), $NH_2$, $NH(C_{1-6}$-alkyl), $N(C_{1-6}$-alkyl)$_2$, or $NHC(O)(C_{1-6}$-alkyl).

In certain embodiments of Formula I and Formula II, R³, R⁴, R⁵, R⁶, R⁷ and R⁸ are each, independently, H.

In certain other embodiments of Formula I and Formula II, R¹ is CN.

In certain embodiments of Formula I, R² is unsubstituted phenyl.

In certain embodiments of Formula II, R² is phenyl, wherein the phenyl is substituted at the para position. In certain other embodiments of Formula II, R² is phenyl, wherein the phenyl is substituted at the para position with $N(CH_3)_2$, $OCH_3$, piperazinyl, (N-methyl)piperazinyl, piperidinyl, morpholinyl or a group corresponding to a cholesterol molecule.

In some embodiments of Formula I and Formula II, N=N—R² is oriented cis to the tricycle. In other embodiments of Formula I and Formula II, N=N—R² is oriented trans to the tricycle.

In some embodiments of Formula II, the phenyl is substituted at the para position with OMe.

In other embodiments of Formula II, the phenyl is substituted at the para position with $N(CH_3)_2$.

In other embodiments of Formula II, the phenyl is substituted at the para position with piperazinyl.

In other embodiments of Formula II, the phenyl is substituted at the para position with piperidinyl.

In other embodiments of Formula II, the phenyl is substituted at the para position with (N-methyl)piperazinyl.

In other embodiments of Formula II, the phenyl is substituted at the para position with morpholinyl.

In other embodiments of Formula II, the phenyl is substituted at the para position with a group corresponding to a cholesterol molecule.

In certain embodiments of Formula I and Formula II, R³, R⁴, R⁵, R⁶, R⁷ and R⁸ are each, independently, a bond to a pharmaceutical agent.

In one aspect, provided herein is a photochromic molecular switch comprising at least one compound of Formula I or a salt thereof. In another aspect, provided herein is a photochromic molecular switch comprising at least one compound of Formula II or a salt thereof.

In certain embodiments, the molecular switch comprising the salt of Formula I or the salt of Formula II is reacted with a pharmaceutically acceptable salt to form a photopharmaceutical compound. In certain embodiments, the pharmaceutically acceptable salt is a salt of a small molecule pharmaceutical.

In one embodiment, the molecular switch comprising the compound of Formula I or the compound of Formula II or a photopharmaceutical compound thereof is stable in water or biological fluid. In another embodiment, the molecular switch comprising the compound of Formula I or the compound of Formula II or a photopharmaceutical compound thereof does not substantially hydrolyze in water or biological fluid.

Certain embodiments of Formula I and Formula II are shown in Table A and also are considered to be "compounds of the invention".

TABLE A

| Compound No. | Structure | NMR and/or MS |
| --- | --- | --- |
| 1 | 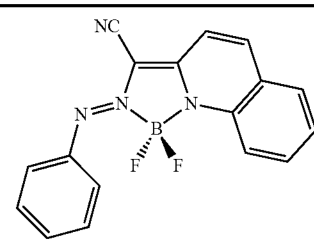 | ¹H NMR (500 MHz, $CD_2Cl_2$) δ 8.42 (d, J = 9.0 Hz, 1H), 8.09 (d, J = 7.5 Hz, 1H), 7.91 (m, 2H), 7.63 (t, J = 8.0 Hz, 1H), 7.51 (m, 2H), 7.40 (m, 2H), 7.20 (m, 2H) ppm; ¹³C NMR (126 MHz, $CD_2Cl_2$) δ 145.39, 144.61, 134.66, 134.29, 129.90, 129.84, 129.15, 128.95, 128.65, 127.21, 126.54, 126.03, 121.27, 119.63, 114.13 ppm; ¹⁹F NMR (282 MHz, $CDCl_3$) δ −150.66 (q, J = 28.3 Hz, 2F) ppm; GC-MS: calcd for $C_{17}H_{11}BF_2N_4$, 320.1; m/z (rel. inten.) 320 (15%, M⁺), 140 (29%), 113 (11%), 91 (25%), 77 (100%), 51 (35%). |
| 2 | 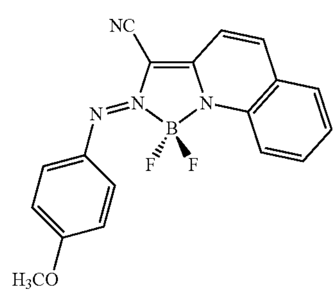 | ¹H NMR (500 MHz, $CD_2Cl_2$) δ 8.21 (d, J = 10.0 Hz, 1H), 7.81 (d, J = 10.0 Hz, 2H), 7.76 (t, J = 5.0 Hz, 1H), 7.72 (d, J = 10.0 Hz, 2H), 7.49 (t, J = 7.5 Hz, 1H), 7.34 (d, J = 10.0 Hz, 1H), 7.03 (d, J = 5.0 Hz, 2H), 3.91 (s, 3H) ppm; ¹³C NMR (126 MHz, $CD_2Cl_2$) δ 161.30, 152.71, 144.76, 143.49, 139.17, 133.72, 129.60, 125.71, 125.04, 123.28, 118.34, 114.59, 114.20, 113.78, 112.91, 55.88 ppm; ¹⁹F NMR (282 MHz, $CD_2Cl_2$) δ −145.95 (q, J = 19.7 Hz, 2F) ppm; GC-MS: calcd |

TABLE A-continued

| Compound No. | Structure | NMR and/or MS |
|---|---|---|
| | | for $C_{18}H_{13}BF_2N_4O$, 350.1; m/z (rel. inten.) 350 (23%, M+), 144 (10%), 140 (28%), 107 (100%), 91 (22%), 51 (32%). |
| 3 | 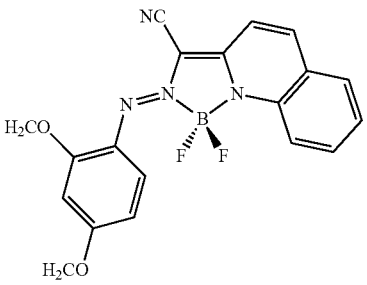 | $^1$H NMR (500 MHz, $CD_2Cl_2$) δ 8.36 (d, J = 10.0 Hz, 1H), 8.06 (d, J = 10.0 Hz, 1H), 7.88 (m, 2H), 7.60 (t, J = 7.5 Hz, 1H), 7.41 (d, J = 10.0 Hz, 1H), 7.21 (d, J = 10.0 Hz, 1H), 6.66 (d, J = 10.0 Hz, 1H), 6.56 (dd, J = 5.0 Hz, 1H), 3.95 (s, 3H), 3.90 (s, 3H) ppm; $^{13}$C NMR (126 MHz, $CD_2Cl_2$) δ 162.75, 161.85, 144.56, 143.48, 134.16, 133.67, 129.53, 125.73, 121.97, 119.26, 118.38, 114.17, 114.08, 105.14, 104.72, 99.24, 98.03, 56.46, 55.87 ppm; $^{19}$F NMR (282 MHz, $CD_2Cl_2$) (δ −150.71 (q, J = 25.4 Hz, 2F) ppm; GC-MS: calcd for $C_{19}H_{15}BF_2N_4O_2$, 380.1; m/z (rel. inten.) 380 (24%, M+), 207 (70%), 137 (26%), 128 (30%), 73 (100%). |
| 4 | 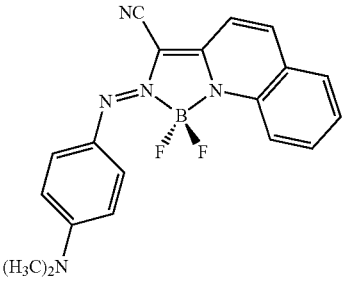 | $^1$H NMR (500 MHz, $CD_2Cl_2$) δ 7.94 (d, J = 10.0 Hz, 1H), 7.86 (d, J = 10.0 Hz, 2H), 7.72 (d, J = 10.0 Hz, 1H), 7.66 (m, 2H), 7.36 (t, J = 10.0 Hz, 1H), 7.15 (d, J = 10.0 Hz, 1H), 6.80 (d, J = 10.0 Hz, 2H), 3.17 (s, 6H) ppm; $^{13}$C NMR (126 MHz, $CD_2Cl_2$) δ 152.49, 141.25, 139.42, 132.86, 129.29, 128.25, 128.20, 128.15, 124.48. 124.36, 117.66, 117.64, 114.48, 114.01, 112.11, 40.30 ppm; $^{19}$F NMR (282 MHz, $CD_2Cl_2$) δ −150.45 (q, J = 32.0 Hz, 2F) ppm; GC-MS: calcd for $C_{19}H_{16}BF_2N_5$, 363.1; m/z (rel. inten.) 363 (20%, M+), 281 (4%), 207 (11%), 134 (100%), 120 (49%), 65 (17%). |
| 5 | 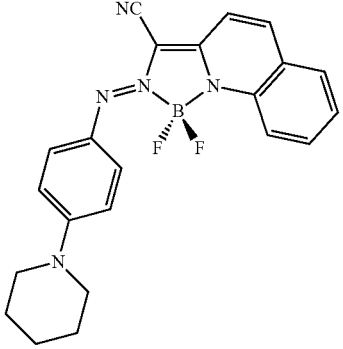 | $^1$H NMR (500 MHz, $CD_2Cl_2$) δ 7.96 (d, J = 10.0 Hz, 1H), 7.82 (d, J = 7.5 Hz, 2H), 7.73 (d, J = 10.0 Hz, 1H), 7.67 (m, 2H), 7.37 (t, J = 10.0 Hz, 1H), 7.17 (d, J = 10.0 Hz, 1H), 6.95 (d, J = 10.0 Hz, 2H), 3.51 (t, J = 5.0 Hz, 4H), 1.72 (s, 6H) ppm; $^{13}$C NMR (126 MHz, $CD_2Cl_2$) δ 152.69, 141.44, 138.81, 132.94, 129.32, 128.12, 128.04, 124.60, 124.43. 117.72, 117.31, 116.41, 114.47, 113.93, 113.74, 48.59, 25.78, 24.54 ppm; $^{19}$F NMR (282 MHz, $CD_2Cl_2$) δ −150.11 (q, J = 18.8 Hz, 2F) ppm; GC-MS: calcd for $C_{22}H_{20}BF_2N_5$, 403.2; m/z (rel. inten.) 403 (14%, M+), 355 (10%), 281 (35%), 253 (12%), 207 (87%), 135 (31%), 73 (100%). |

TABLE A-continued

| Compound No. | Structure | NMR and/or MS |
|---|---|---|
| 6 | 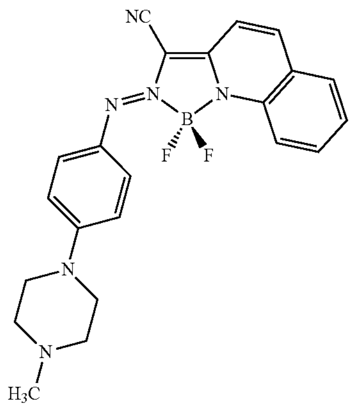 | $^1$H NMR (500 MHz, CD$_2$Cl$_2$) δ 8.02 (d, J = 10.0 Hz, 1H), 7.81 (d, J = 5.0 Hz, 2H), 7.70 (m, 3H), 7.40 (t, J = 10.0 Hz, 1H), 7.21 (d, J = 10.0 Hz, 1H), 6.97 (d, J = 7.5 Hz, 2H), 3.48 (t, J = 5.0 Hz, 4H), 2.55 (t, J = 5.0 Hz, 4H), 2.33 (s, 3H) ppm; $^{13}$C NMR (126 MHz, CD$_2$Cl$_2$) δ 152.46, 152.23, 141.96, 139.70, 139.35, 133.13, 129.39, 127.49, 127.39, 124.89, 124.58, 117.87, 114.40, 113.97, 113.70, 54.85, 47.22, 46.04 ppm; $^{19}$F NMR (282 MHz, CD$_2$Cl$_2$) δ −149.31 (q, J = 18.8 Hz, 2F) ppm; GC-MS: calcd for C$_{22}$H$_{21}$BF$_2$N$_6$, 418.2; m/z (rel. inten.) 418 (20%, M$^+$), 355 (12%), 281 (30%), 253 (13%), 207 (84%), 77 (100%). |
| 7 | 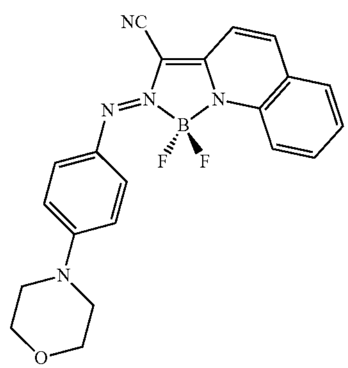 | $^1$H NMR (500 MHz, CD$_2$Cl$_2$) δ 8.06 (d, J = 5.0 Hz, 1H), 7.81 (d, J = 7.5 Hz, 2H), 7.73 (m, 3H), 7.42 (t, J = 7.5 Hz, 1H), 7.24 (d, J = 10.0 Hz, 1H), 6.97 (d, J = 10.0 Hz, 2H), 3.86 (t, J = 5.0 Hz, 4H), 3.41 (t, J = 5.0 Hz, 4H) ppm; $^{13}$C NMR (126 MHz, CD$_2$Cl$_2$) δ 152.44, 142.31, 140.35, 139.30, 133.32, 129.52, 129.39, 127.09, 126.92, 125.09, 124.69, 117.97, 114.36, 114.07, 113.52, 66.65, 47.51 ppm; $^{19}$F NMR (282 MHz, CD$_2$Cl$_2$) δ −148.73 (q, J = 18.8 Hz, 2F) ppm; GC-MS: calcd for C$_{21}$H$_{18}$BF$_2$N$_5$O, 405.2; m/z (rel. inten.) 405 (26%, M$^+$), 355 (10%), 281 (32%), 253 (11%), 207 (83%), 135 (37%), 73 (100%). |
| 8 | 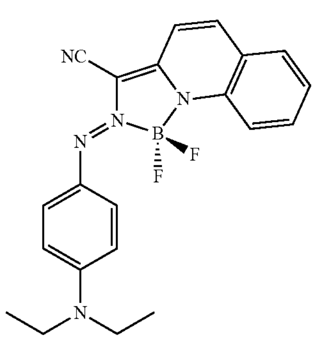 | $^1$H NMR (500 MHz CD$_2$Cl$_2$) δ: 7.81, 7.76, 7.62, 7.55, 7.47, 7.24, 7.03, 6.68, 4.33, 3.56, 1.75, 1.47 |

TABLE A-continued

| Compound No. | Structure | NMR and/or MS |
|---|---|---|
| 9 | 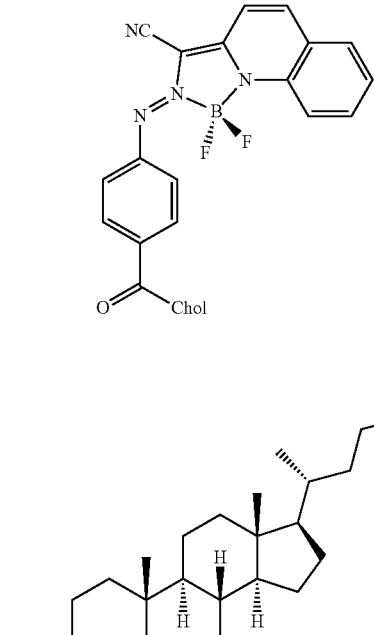 | $^{1}$H NMR (500 MHz, CD$_2$Cl$_2$) δ = 8.41 (d, J = 8.9 Hz, 1H), 8.13 (dd, J = 6.8, 1.9 Hz, 2H), 7.91 (d, J = 7.9 Hz, 1H), 7.84 (m, 2H), 7.59 (t, J = 8 Hz, 1H), 7.53 (d, J = 8.6 Hz, 2H), 7.49 (d, J = 8.9 Hz, 1H), 5.37 (s, 1H), 4.86 (m, 1H), 2.50 (m, 1h), and 2.11-0.062 (cholesterol skeleton). $^{13}$C NMR (126 MHz, CD$_2$Cl$_2$) δ = 165.22, 152.68, 144.96, 140.02, 139.11, 134.41, 131.12, 130.25, 130.22, 129.77, 128.95, 126.77, 125.73, 122.88, 122.40, 118.87, 114.22, 75.00, 71.89, 65.69, 56.97, 56.39, 54.08, 53.86, 53.65, 53.43, 53.21, 50.35, 42.52, 40.01, 39.71, 38.40, 37.26, 36.87, 36.40, 36.04, 32.17, 32.11, 30.78, 28.42, 28.24, 28.07, 27.96, 24.47, 24.02, 22.77, 22.52, 21.27, 19.40, 19.37, 19.10, 18.72, 13.71, 11.84 ppm; $^{19}$F NMR (282 MHz, CD$_2$Cl$_2$) δ = −150.66 (m, 2F); GC-MS: calcd. for C$_{45}$H$_{55}$BF$_2$N$_4$O$_2$ 732.33; m/z (rel. inten.) 732.2 (7.5%, M+). |

Photoisomerizable Group

A photoisomerizable group is one that changes from a first isomeric form to a second isomeric form upon exposure to electromagnetic radiation of different wavelengths, or upon a change in exposure from dark to light, or from light to dark. For example, in some embodiments, the photoisomerizable group is in a first isomeric form of a compound of Formula I or a first isomeric form of a compound of Formula II when exposed to electromagnetic radiation of a first wavelength, and is in a second isomeric form of a compound of Formula I or a second isomeric form of a compound of Formula II when exposed to electromagnetic radiation of a second wavelength.

The first wavelength and the second wavelength can differ from one another by from about 1 nm to about 600 nm or more, for example, from about 1 nm to about 10 nm, from about 10 nm to about 20 nm, from about 20 nm to about 50 nm, from about 50 nm to about 75 nm, from about 75 nm to about 100 nm, from about 100 nm to about 125 nm, from about 125 nm to about 150 nm, or from about 150 nm to about 200 nm, from about 200 nm to about 500 nm, from about 500 nm to about 600 nm, or more than 600 nm.

In other embodiments, the compound of Formula I or the compound of Formula II is in a first isomeric form when exposed to light of a wavelength $\lambda_1$, and is in a second isomeric form in the absence of light (e.g., in the absence of light, the compound undergoes spontaneous relaxation into the second isomeric form). In these embodiments, the first isomeric form of the compound of Formula I or the first isomeric form of a compound of Formula II is induced by exposure to light of wavelength $\lambda_1$, and the second isomeric form is induced by not exposing the compound to light (e.g., keeping the compound in darkness). In other embodiments, the compound of Formula I or the compound of Formula II is in a first isomeric form in the absence of light (e.g., when the compound is in the dark; and the compound is in a second isomeric form when exposed to light of a wavelength $\lambda_1$). In other embodiments, the compound of Formula I or the compound of Formula II is in a first isomeric form when exposed to light of a first wavelength $\lambda_1$, and then in a second isomeric form when exposed to light of a second wavelength $\lambda_2$.

For example, in some embodiments provided herein, the compound of Formula I or the compound of Formula II is in a trans configuration in the absence of light, or when exposed to light of a first wavelength; and the photoisomerizable group is in a cis configuration when exposed to light of a second wavelength that is different from the first wavelength.

In some embodiments, the wavelength of light that effects a change in the compound of Formula I or in the compound of Formula II from a first isomeric form to a second isomeric form ranges from 400 nanometers to 1000 nanometers.

In other embodiments, the wavelength of light that effects a change in the compound of Formula I or in the compound of Formula II from a first isomeric form to a second isomeric form ranges from 450 nanometers to 850 nanometers.

In other embodiments, the wavelength of light that effects a change in the compound of Formula I or in the compound of Formula II from a first isomeric form to a second isomeric form ranges from 710 nanometers to 760 nanometers.

The difference between the first wavelength and the second wavelength can range from about 1 nm to about 600 nm or more, as described above. Of course, where the synthetic light regulator is switched from light to darkness, the difference in wavelength is from the wavelength $\lambda_2$ to essentially zero.

Methods of Using Molecular Switches

The select application of electromagnetic radiation to the compounds of Formula I or the compounds of Formula II or photopharmaceutical compounds comprising a Formula I or Formula II moiety can be used to transform a compound from a trans azo isomeric form to a cis azo isomeric form or vice versa. In this way, the compounds can be used as a molecular switch, with the electromagnetic radiation serving as a switching means.

In some embodiments, the compounds of Formula I and Formula II or photopharmaceutical compounds thereof respond to electromagnetic radiation that is generated by an infrared light source and/or a visible light source. Therefore, in some of these embodiments, the compounds of Formula I or the compounds of Formula II respond to a first wavelength $\lambda_1$ ranging from 400 nanometers to 1 millimeter to convert the trans azo isomer to the cis azo isomer; and a second wavelength $\lambda_2$ ranging from 400 nanometers to 1 millimeter causes the cis azo isomer to convert back to the trans azo isomer.

For example, in certain embodiments, the compounds of Formula I or the compounds of Formula II or photopharmaceutical compounds thereof respond to a first wavelength $\lambda_1$ ranging from 700 nanometers to 1000 nanometers to convert the trans azo isomer to the cis azo isomer; and to a second wavelength $\lambda_2$ ranging from 700 nanometers to 1000 nanometers. Additionally, in certain other embodiments, the compounds of Formula I or the compounds of Formula II or photopharmaceutical compounds thereof respond to a first wavelength $\lambda_1$ ranging from 450 nanometers to 850 nanometers to convert the trans azo isomer to the cis azo isomer; and a second wavelength $\lambda_2$ ranging from 450 nanometers to 850 nanometers causes the cis azo isomer to convert back to the trans azo isomer.

In some other embodiments, the compounds of Formula I or the compounds of Formula II or photopharmaceutical compounds thereof respond to electromagnetic radiation that is generated by a visible light source. Therefore, in some of these embodiments, the compounds of Formula I or the compounds of Formula II or photopharmaceutical compounds thereof respond to a first wavelength $\lambda_1$ ranging from 570 to 750 nanometers to convert the trans azo isomer to the cis azo isomer; and a second wavelength $\lambda_2$ ranging from 450 to 495 nanometers causes the cis azo isomer to convert back to the trans azo isomer.

The skilled artisan will appreciate that the photochromic materials described herein need not be limited to those responsive to the exemplary wavelength ranges described herein.

Definitions

In this disclosure, "comprises," "comprising," "containing," and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

Unless otherwise specified, "a" or "an" means "one or more".

The term "electromagnetic radiation" as used herein, refers to a form of energy exhibiting wave like behavior and having both electric and magnetic field components, which oscillate in phase perpendicular to each other as well as perpendicular to the direction of energy propagation. Electromagnetic radiation is classified according to the frequency of its wave. In order of increasing frequency (f) and decreasing wavelength ($\lambda$), electromagnetic radiation includes: radio waves (3 Hz≤f≤300 MHz; 1 m≤$\lambda$≤100,000 Km), microwaves (300 MHz≤f≤300 GHz; 1 mm≤$\lambda$≤1 m), infrared radiation (300 GHz≤f≤400 THz; 750 nm≤$\lambda$≤1 m), visible light (400 THz≤f≤770 THz; 400 nm≤$\lambda$≤1 m), ultraviolet radiation (750 THz≤f≤30 PHz; 10 nm≤$\lambda$≤400 nm), X-rays (300 PHz≤f≤30 EHz; 0.01 nm≤$\lambda$≤10 nm), and gamma rays (f≥15 EHz; $\lambda$≤0.02 nm). Hence, the term "electromagnetic radiation", as used herein, denotes photons, particularly in the visible range and/or in the infrared region.

The term "photochromism", as used herein, indicates a photoinduced change in color. Herein, the interconversion usually occurs between two colored states. A photochromic transformation is always accompanied by profound absorbance changes in the visible region. In fact, visible absorption spectroscopy is the most convenient analytical method to study these processes.

The term "photostationary state", as used herein, indicates a state where no further changes in the UV/Vis spectra are observed. For example, application of additional electromagnetic energy to a sample or molecule in a photostationary state does not produce a change in absorption or emission spectra.

As used herein, the term "molecular switch" refers to a molecule that generates a change in state in response to a signal. In one aspect, a molecular switch is capable of switching from at least one state to at least one other state in response to the signal.

As used herein, the expression "a group corresponding to" an indicated species expressly includes a radical (including a monovalent, divalent and trivalent radical), for example an aromatic radical or heterocyclic aromatic radical, of the species or group of species provided in a covalently bonded configuration.

As used herein, the term "group" may refer to a functional group of a chemical compound. Groups of the present compounds refer to an atom or a collection of atoms that are a part of the compound. Groups of the present invention may be attached to other atoms of the compound via one or more covalent bonds. Groups may also be characterized with respect to their valence state. The present invention includes groups characterized as monovalent, divalent, trivalent, etc.

As used herein, the term "substituted" refers to a compound wherein a hydrogen is replaced by another functional group.

As used herein, the term "a small molecule pharmaceutical" refers to a compound, typically an organic compound, with a molecular weight of 900 Daltons or less, or 500 Daltons or less, where the compound has a therapeutic functionality or a diagnostic functionality. In some embodiments, a small molecule pharmaceutical is a compound that is, within the scope of sound medical judgment, suitable for use in contact with the tissues of humans and lower animals without undue toxicity, irritation, allergic response and the like, and that is commensurate with a reasonable benefit/risk ratio.

As used herein, the term "photopharmaceutical compound" refers to a molecule comprising a molecular switch moiety and a pharmaceutical compound moiety, where the moieties may be covalently, ionically or electrostatically bonded or attracted. In some embodiments, a photopharmaceutical compound is synthesized by reacting a salt of a molecular switch with a pharmaceutically acceptable salt. Salts of molecular switches are compounds wherein the parent compound is modified by converting an existing acid or base moiety to its salt form. Examples of salts include, but are not limited to, mineral or organic acid salts of basic residues such as amines; alkali or organic salts of acidic residues such as carboxylic acids; and the like. The salts can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two.

The term "pharmaceutically acceptable salt" refers to those salts of pharmaceutical compounds which are, within the scope of sound medical judgment, suitable for use in contact with the tissues of humans and lower animals without undue toxicity, irritation, allergic response and the like, and are commensurate with a reasonable benefit/risk ratio. Additionally, "pharmaceutically acceptable salts" refers to compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts of the parent compound formed, for example, from non-toxic inorganic or organic acids. The pharmaceutically acceptable salts can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17$^{th}$ ed., Mack Publishing Company, Easton, Pa., 1985, p. 1418 and Journal of Pharmaceutical Science, 66, 2 (1977), each of which is incorporated herein by reference in its entirety.

As used herein, the term "tissue target" or "target of a tissue" refers to biomolecules or fragments thereof including, but not limited to, hormones, amino acids, peptides, peptidomimetics, proteins, nucleosides, nucleotides, nucleic acids, enzymes, carbohydrates, glycomimetics, lipids, albumins, mono- and polyclonal antibodies, receptors, inclusion compounds such as cyclodextrins, and receptor binding molecules.

As used herein, the term "alkyl" refers to a fully saturated branched or unbranched hydrocarbon moiety. Preferably the alkyl comprises 1 to 20 carbon atoms, more preferably 1 to 16 carbon atoms, 1 to 10 carbon atoms, 1 to 7 carbon atoms, 1 to 6 carbons, 1 to 4 carbons, or 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. Furthermore, the expression "$C_x$-$C_y$-alkyl", wherein x is 1-5 and y is 2-10 indicates a particular alkyl group (straight- or branched-chain) of a particular range of carbons. For example, the expression $C_1$-$C_4$-alkyl includes, but is not limited to, methyl, ethyl, propyl, butyl, isopropyl, tert-butyl and isobutyl.

As used herein, the term "cycloalkyl" refers to saturated or unsaturated monocyclic, bicyclic or tricyclic hydrocarbon groups of 3-12 carbon atoms, preferably 3-9, or 3-7 carbon atoms. Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like.

The term "heteroalkyl," by itself or in combination with another term, means, unless otherwise stated, a stable straight or branched chain, or combinations thereof, consisting of the stated number of carbon atoms and from one to five heteroatoms, more preferably from one to three heteroatoms, selected from the group consisting of O, N, Si and S, and wherein the nitrogen and sulfur atoms may optionally be oxidized and the nitrogen heteroatom may optionally be quaternized. The heteroalkyl group is attached to the remainder of the molecule through a carbon atom or a heteroatom.

The term "aryl" includes aromatic monocyclic or multicyclic (e.g., tricyclic, bicyclic), hydrocarbon ring systems consisting only of hydrogen and carbon and containing from six to nineteen carbon atoms, or six to ten carbon atoms, where the ring systems may be partially saturated. Aryl groups include, but are not limited to, groups such as phenyl, tolyl, xylyl, anthryl, naphthyl and phenanthryl. Aryl groups can also be fused or bridged with alicyclic or heterocyclic rings which are not aromatic so as to form a polycycle (e.g., tetralin).

The term "heteroaryl," as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

The term "heterocycle" or "heterocycyl" refers to five-member to ten-member, fully saturated or partially unsaturated nonaromatic heterocyclic groups containing at least one heteroatom such as O, S or N. The most frequent examples are piperidinyl, morpholinyl, piperazinyl, pyrrolidinyl or pirazinyl. Attachment of a heterocycyl substituent can occur via a carbon atom or via a heteroatom.

Moreover, the alkyl, alkenyl, cycloalkyl, cycloalkenyl, alkoxy, aryl, heteroaryl, and heterocycle groups described above can be "unsubstituted" or "substituted."

The term "substituted" is intended to describe moieties having substituents replacing a hydrogen on one or more atoms, e.g. C, O or N, of a molecule. Such substituents can independently include, for example, one or more of the following: straight or branched alkyl (preferably $C_1$-$C_5$), cycloalkyl (preferably $C_3$-$C_8$), alkoxy (preferably $C_1$-$C_6$), thioalkyl (preferably $C_1$-$C_6$), alkenyl (preferably $C_2$-$C_6$), alkynyl (preferably $C_2$-$C_6$), heterocyclic, carbocyclic, aryl (e.g., phenyl), aryloxy (e.g., phenoxy), aralkyl (e.g., benzyl), aryloxyalkyl (e.g., phenyloxyalkyl), arylacetamidoyl, alkylaryl, heteroaralkyl, alkylcarbonyl and arylcarbonyl or other such acyl group, heteroarylcarbonyl, or heteroaryl group, $(CR'R'')_{0-3}NR'R''$ (e.g., —$NH_2$), $(CR'R'')_{0-3}CN$ (e.g., —CN), —$NO_2$, halogen (e.g., —F, —Cl, —Br, or —I), $(CR'R'')_{0-3}C(halogen)_3$ (e.g., —$CF_3$), $(CR'R'')_{0-3}CH(halogen)_2$, $(CR'R'')_{0-3}CH_2(halogen)$, $(CR'R'')_{0-3}CONR'R''$, $(CR'R'')_{0-3}(CNH)NR'R''$, $(CR'R'')_{0-3}S(O)_{1-2}NR'R''$, $(CR'R'')_{0-3}CHO$, $(CR'R'')_{0-3}O(CR'R'')_{0-3}H$, $(CR'R'')_{0-3}S(O)_{0-3}R'$ (e.g., —$SO_3H$, —$OSO_3H$), $(CR'R'')_{0-3}O(CR'R'')_{0-3}H$ (e.g., —$CH_2OCH_3$ and —$OCH_3$), $(CR'R'')_{0-3}S(CR'R'')_{0-3}H$ (e.g., —SH and —$SCH_3$), $(CR'R'')_{0-3}OH$ (e.g., —OH), $(CR'R'')_{0-3}COR'$, $(CR'R'')_{0-3}$(substituted or unsubstituted phenyl), $(CR'R'')_{0-3}(C_3$-$C_8$ cycloalkyl), $(CR'R'')_{0-3}CO_2R'$(e.g., —$CO_2H$), or $(CR'R'')_{0-3}OR'$ group, or the side chain of any naturally occurring amino acid; wherein R' and R" are each independently hydrogen, a $C_1$-$C_5$ alkyl, $C_2$-$C_5$ alkenyl, $C_2$-$C_5$ alkynyl, or aryl group.

As is customary and well known in the art, hydrogen atoms are not always explicitly shown on chemical structures, for example, hydrogen atoms bonded to the carbon atoms of aromatic, heteroaromatic, and alicyclic rings are not always explicitly shown.

The description of the disclosure herein should be construed in congruity with the laws and principals of chemical bonding. For example, it may be necessary to remove a hydrogen atom in order accommodate a substituent at any given location. Furthermore, it is to be understood that definitions of the variables (i.e., "R groups"), as well as the bond locations of the generic formula of the invention (i.e., Formula I or Formula II), will be consistent with the laws of chemical bonding known in the art. It is also to be understood that all of the compounds of the invention described above will further include bonds between adjacent atoms and/or hydrogens as required to satisfy the valence of each atom. That is, bonds and/or hydrogen atoms are added to provide the following number of total bonds to each of the following types of atoms: carbon: four bonds; nitrogen: three bonds; oxygen: two bonds; and sulfur: two-six bonds.

The compounds of this invention may include asymmetric carbon atoms. It is to be understood accordingly that the isomers arising from such asymmetry (e.g., all enantiomers, stereoisomers, rotamers, tautomers, diastereomers, or racemates) are included within the scope of this invention. Such isomers can be obtained in substantially pure form by classical separation techniques and by stereochemically controlled synthesis. Furthermore, the structures and other compounds and moieties discussed in this application also include all tautomers thereof. Compounds described herein may be obtained through art recognized synthesis strategies.

It will also be noted that the substituents of some of the compounds of this invention include isomeric cyclic structures. It is to be understood accordingly that constitutional isomers of particular substituents are included within the scope of this invention, unless indicated otherwise. For example, the term "tetrazole" includes tetrazole, 2H-tetrazole, 3H-tetrazole, 4H-tetrazole and 5H-tetrazole.

EXEMPLIFICATION

The invention is further illustrated by the following examples, which should not be construed as further limiting. The practice of the present invention will employ, unless otherwise indicated, conventional techniques of synthetic and physical organic chemistry as well as computational chemistry, which are within the skill of the art.

Example 1: Synthesis of Compound 1

1.1 Synthesis of Hydrozone 1c

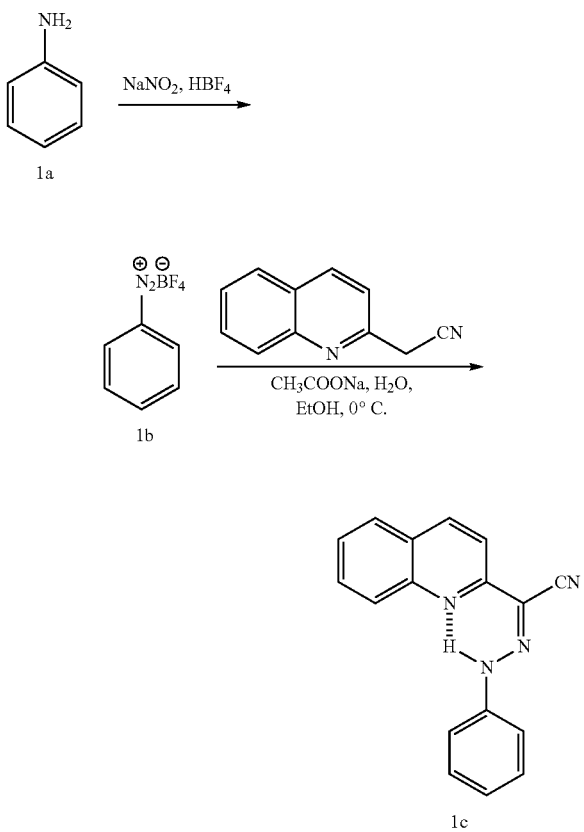

1.7 mL of $HBF_4$ (48%) was added dropwise to a mixture of aniline (0.31 mL, 3.4 mmol) in 1 mL water. After stirring in an ice-bath for 40 min, a precooled solution of $NaNO_2$ (1 equiv, 0.235 g, 3.4 mmol) was then added dropwise over a period of 15 min. The white diazonium salt was collected by filtration after 90 min and added to a suspension of 2-quinolylacetonitrile (0.8 equiv, 0.456 g, 2.7 mmol) and sodium acetate (3.2 equiv, 0.890 g, 10.8 mmol) in a cooled and well stirred 30 mL ethanol/water (2:1) mixture. The resulting reaction mixture was left to stir overnight at RT. The precipitated compound was then collected by filtration and dried over air. The crude product was purified by silica gel column chromatography (hexane/ethyl acetate 15:1) to give hydrazone 1c as a bright yellow powder (0.550 g, 75%). Mp: 159.8-160.4° C.; $^1$H NMR (500 MHz, $CDCl_3$) δ 16.10 (s, 1H), 8.31 (d, J=8.5 Hz, 1H), 8.05 (d, J=8.5 Hz, 1H), 7.86 (m, 2H), 7.81 (t, J=8.5 Hz, 1H), 7.63 (t, J=8.0 Hz, 1H), 7.44 (m, 4H), 7.15 (t, J=9.5 Hz, 1H) ppm; $^{13}$C NMR (126 MHz, $CDCl_3$) δ 152.31, 145.82, 142.47, 138.00, 131.05, 129.94, 129.81, 128.32, 128.10, 127.88, 127.05, 124.70, 119.81, 118.09, 115.50 ppm; GC-MS: calcd for $C_{17}H_{12}N_4$, 272.1; m/z (rel. inten.) 272 (56%, M$^+$), 167 (21%), 140 (34%), 105 (15%), 77 (100%), 51 (15%).

1.2 Synthesis of Compound 1

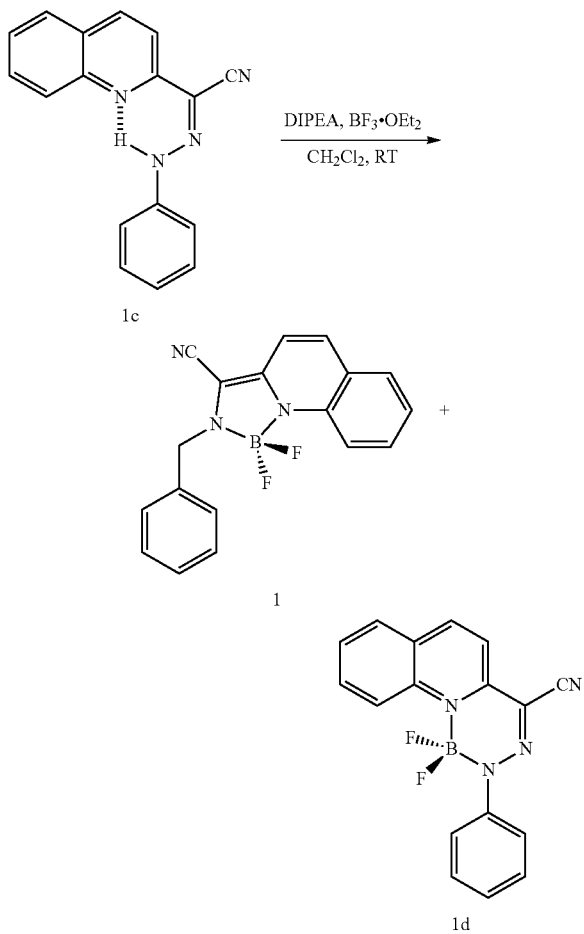

N,N-Diisopropylethylamine (DIPEA, 7 equiv, 0.22 mL, 1.3 mmol) was added to a solution of hydrazone 1c (0.050 g, 0.18 mmol) in dry methylene chloride at room temperature. After 2 hours, boron trifluoride diethyl ether complex (10 equiv, 0.23 mL, 1.8 mmol) was added dropwise. The reaction mixture was stirred at room temperature overnight. The reaction mixture was quenched with water and extracted by methylene chloride. The organic layer was washed two times with 10 mL water, 10 mL saturated sodium bicarbonate solution and dried over magnesium sulfate. After solvent concentration, the crude product was subjected to silica gel column chromatography (methylene chloride/hexane 2:1) to give compound 1 as a dark red solid (40 mg, 68%). The compound starts to decompose at 177.5° C. before reaching its mp; ($^1$H NMR 500 MHz, $CD_2Cl_2$) δ 8.42 (d, J=9.0 Hz, 1H), 8.09 (d, J=7.5 Hz, 1H), 7.91 (m, 2H), 7.63 (t, J=8.0 Hz, 1H), 7.51 (m, 2H), 7.40 (m, 2H), 7.20 (m, 2H) ppm; $^{13}$C NMR (126 MHz, $CD_2Cl_2$) δ 145.39, 144.61, 134.66, 134.29, 129.90, 129.84, 129.15, 128.95, 128.65, 127.21, 126.54, 126.03, 121.27, 119.63, 114.13 ppm; $^{19}$F NMR (282 MHz, $CDCl_3$) δ −150.66 (q, J=28.3 Hz, 2F) ppm; GC-MS: calcd for $C_{17}H_{11}BF_2N_4$, 320.1; m/z (rel. inten.) 320 (15%, $M^+$), 140 (29%), 113 (11%), 91 (25%), 77 (100%), 51 (35%).

The compound (1d) was formed as the minor product during the same reaction of compound 1. After purification by silica gel column chromatography (hexane/ethyl acetate 5:1), 1d was collected as a bright yellow solid with 10% yield. When the reaction was carried out at 60° C., 1 was obtained as the major product (40% yield). mp 229.2-229.6° C.; $^1$H NMR (500 MHz, $CDCl_3$) δ 8.87 (d, J=5.0 Hz, 1H), 8.55 (d, J=4.5 Hz, 1H), 7.93 (m, 5H), 7.75 (t, J=7.5 Hz, 1H), 7.46 (m, 2H), 7.32 (t, J=7.3 Hz, 1H) ppm; $^{13}$C NMR (126 MHz, $CDCl_3$) δ 144.04, 142.65, 133.96, 129.27, 128.87, 127.94, 127.36, 124.05, 123.99, 123.92, 121.09, 121.07, 127.05, 117.78, 116.17 ppm; $^{19}$F NMR (282 MHz, $CDCl_3$) δ −124.17 (q, J=28.3 Hz, 2F) ppm; GC-MS: calcd for $C_{17}H_{11}BF_2N_4$, 320.1; m/z (rel. inten.) 320 (4%, $M^+$), 154 (2%), 128 (5%), 113 (9%), 101 (8%), 91 (17%), 77 (100%).

Compounds of Formula II can be prepared in accordance with the outlined synthesis of Compound I, but starting from aryl-substituted analogues of aniline 1a (e.g., Compound 2 can be prepared starting from p-methoxyaniline; Compound 4 can be prepared starting from p-aminodimethylamine). Subsequently, the substituted aniline can be reduced to a tetrafluoroborate diazonium salt analogous to 1b. Further reaction of 1b-analogues afford aryl-substituted analogues of hydrozone 1c, which can be used to prepare $BF_2$-coordinated compounds of Formula II, as outlined in Example 1.2.

Example 2: Photoisomerism of Compound 1

The photoisomerization of Compound 1 was studied extensively by UV/vis (FIG. 1) spectroscopy. When stored in the dark, Compound 1 adopts its thermodynamically stable trans form that has an absorption maximum ($\lambda_{max}$) at 530 nm ($\epsilon$=8026 $M^{-1}$ $cm^{-1}$). Upon irradiation at 570 nm, the cis form ($\lambda_{max}$=480 nm; $\epsilon$=7792 $M^{-1}$ $cm^{-1}$) becomes dominant, accompanied by a sharp color change of the solution from bright purple to light orange. The process is also accompanied by changes in the intensity of bands at higher energies ($\lambda_{max}$=340 and 264 nm). Irradiation at 450 nm drives the system back to its trans form. The isosbestic points ($\lambda_{max}$=499, 399, 330, and 257 nm) in the UV/vis spectra demonstrate that only two species are exchanging during the isomerization process (FIG. 1b). The trans/cis isomerization can be activated solely by the use of visible light and there is no need for UV light. Furthermore, as shown in FIG. 1c, the system shows very good reversibility as no degradation of Compound 1 was observed during the entire photoisomerization studies that lasted for more than a month.

Example 3: The Calculated (B3LPY/6-311++G**)

Figure 3:
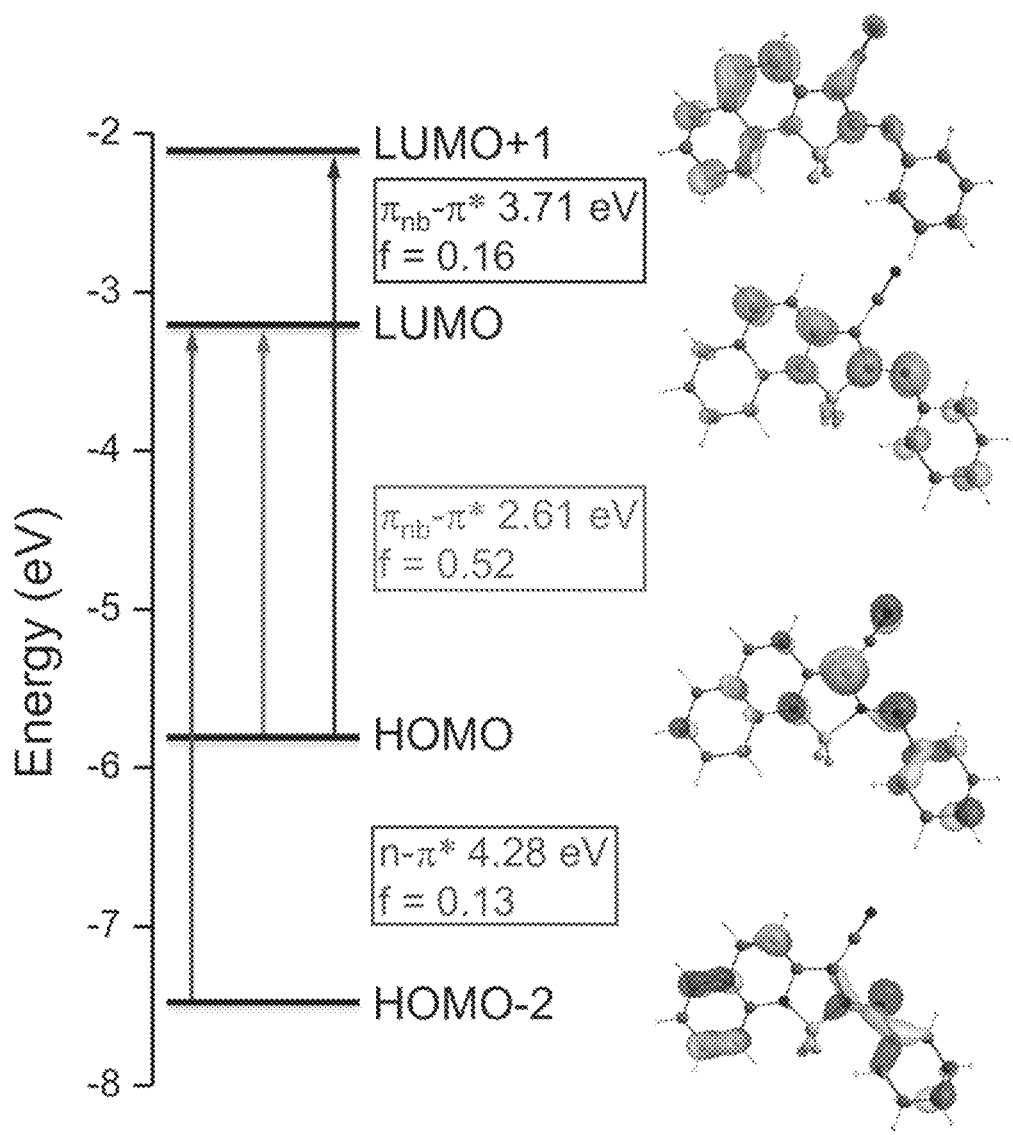
FIG. 3 shows the calculated (B3LYP/6-311++G**) molecular orbital energy levels, transition energies and oscillator strengths of the n→π* and $\pi_{nb}$→π* transitions of the trans isomer of Compound 1.
Figure 4:
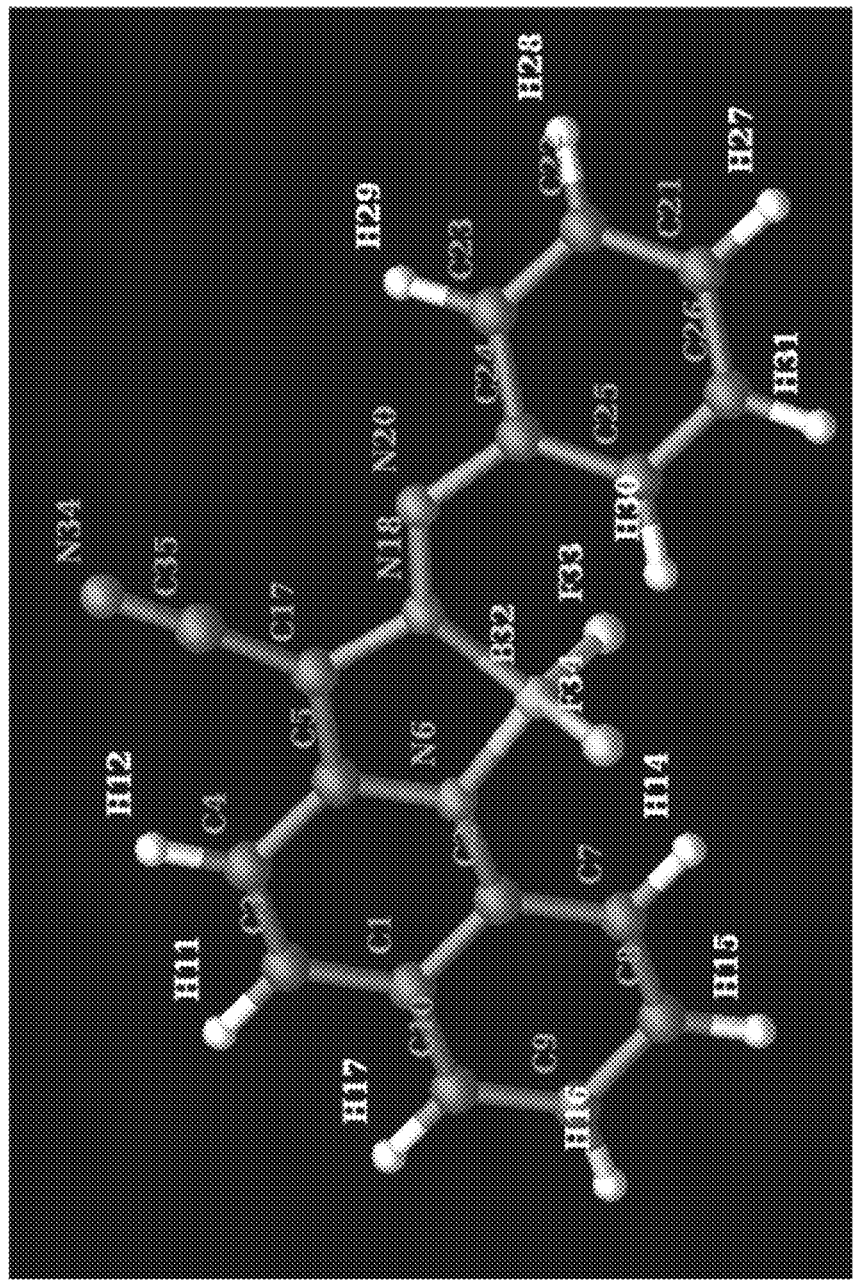
FIG. 4 shows the optimized structure of Compound 1-trans.
Figure 5:
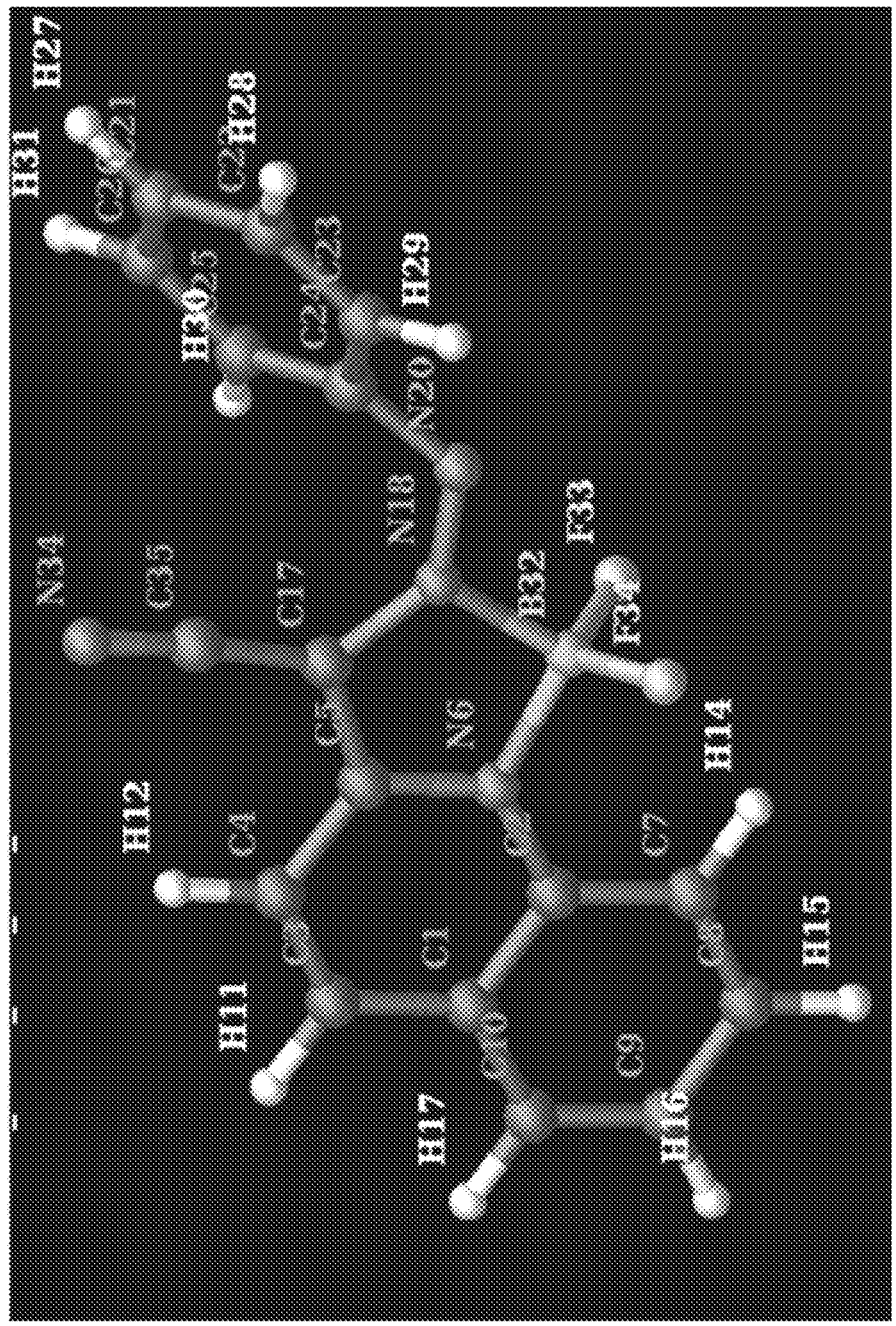
FIG. 5 shows the optimized structure of Compound 1-cis.
Figure 8:
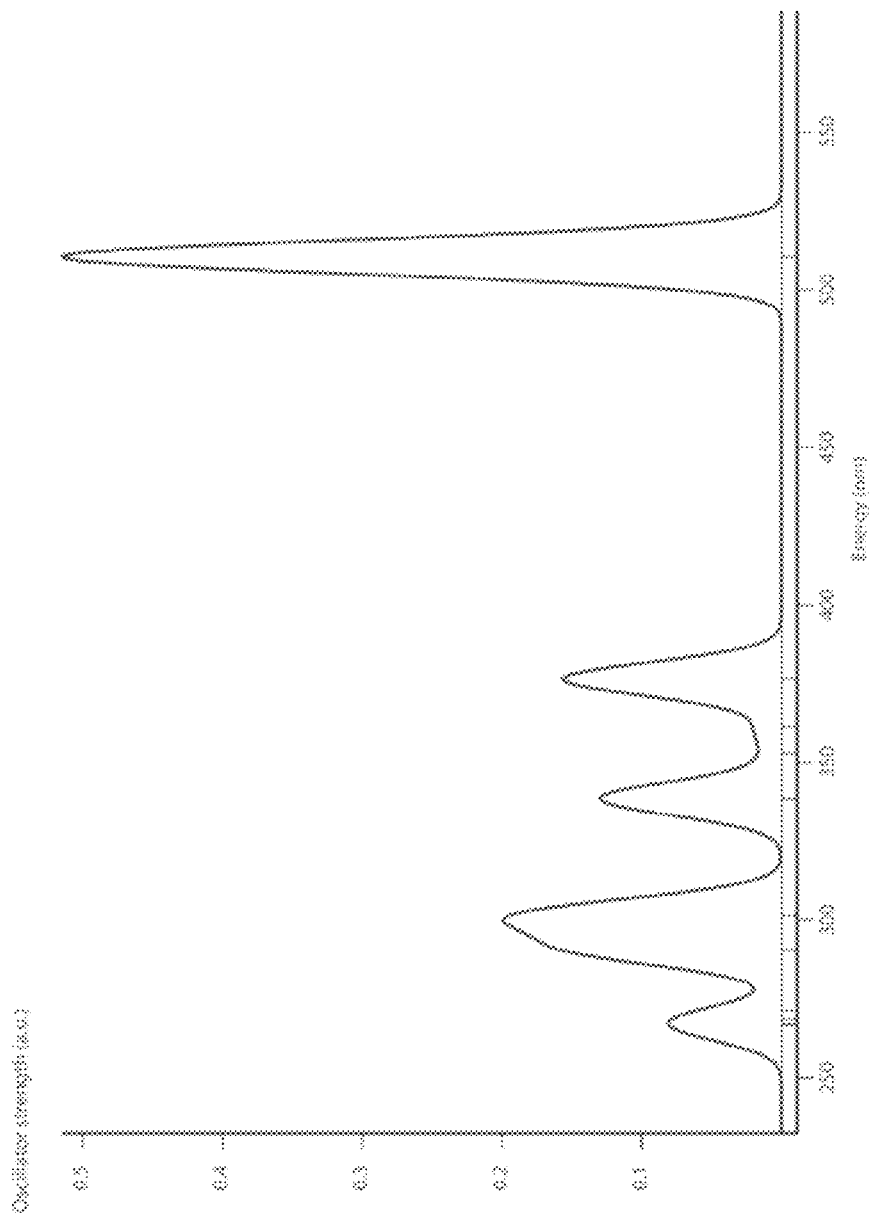
FIG. 8 shows the calculated UV/Vis spectrum of Compound 1-trans.
Figure 9:
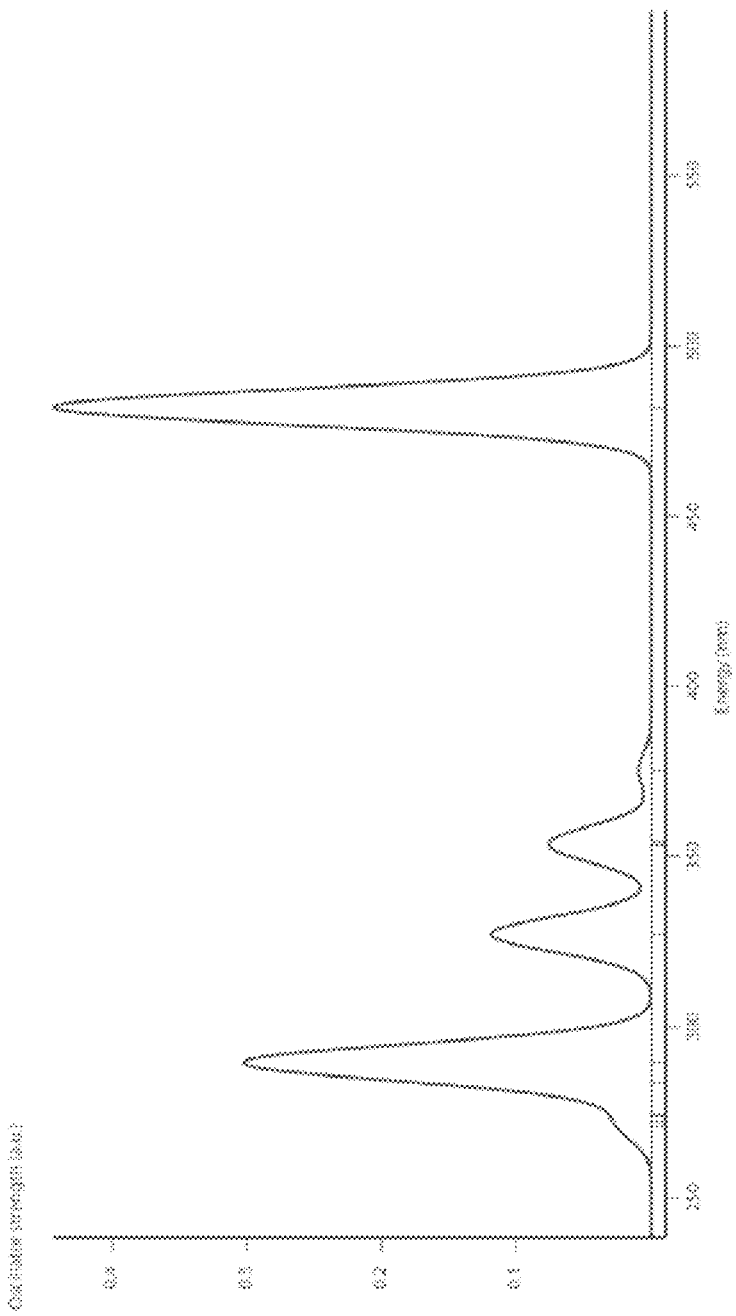
FIG. 9 shows the calculated UV/Vis spectrum of Compound 1-cis.

To understand the effect of Lewis acid coordination on the photophysical properties of azo compounds, computational modeling of the trans and cis isomers of Compound 1 was conducted. Structures were optimized by density functional theory (DFT) using the B3LYP hybrid functional and the 6-311++G** basis set, as implemented in Jaguar; this combination of method and basis set is appropriate for such systems. The optimized structure of trans-Compound 1 matches well with its crystal structure (FIGS. 4 and 5). Calculations of the UV/Vis spectra of the optimized structures were carried out in ADF using time-dependent DFT (TDDFT) using the B3LYP functional and a triple-ζ basis with two added polarization functions (TZ2P). These calculations were also successful in predicting the UV/vis spectra of the cis and trans isomers of Compound 1 (FIGS. 8 and 9), and show that the absorption bands in the visible range (FIG. 3, Table C and FIGS. 14-18S37-S41) stem from π-nonbonding to π*-antibonding transitions (HOMO→LUMO).

Figure 2:
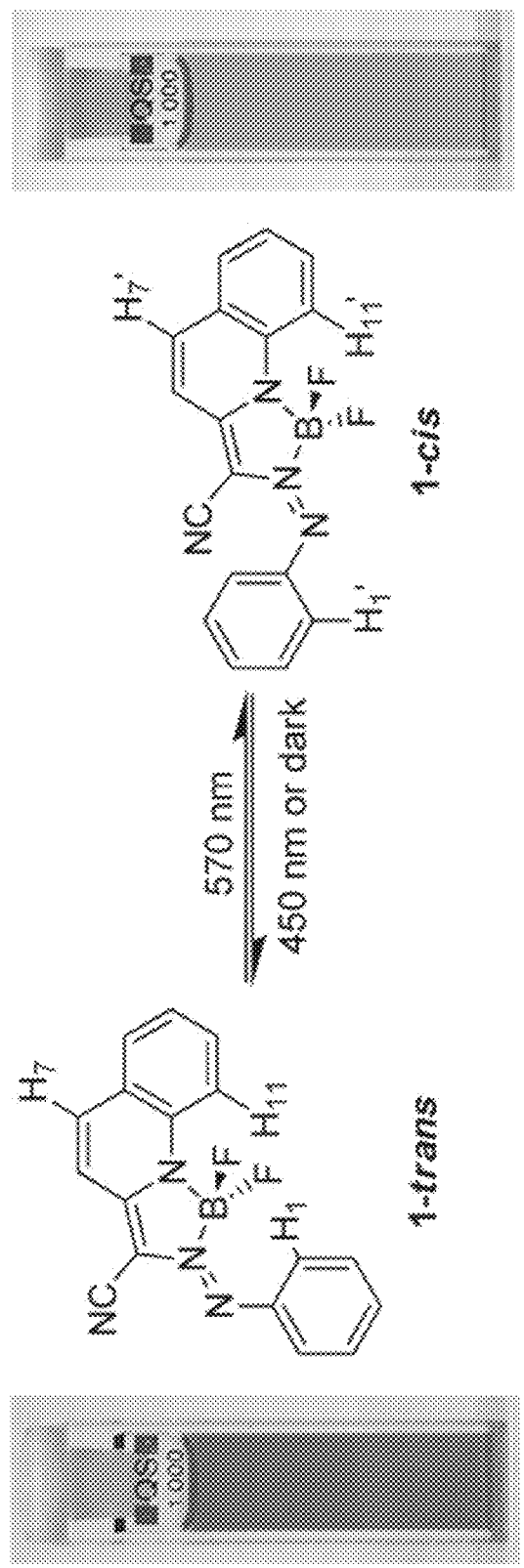
FIG. 2 shows the visible light-induced trans/cis isomerization of Compound 1.

The calculations predict correctly the separation between the cis ($\lambda_{max}$=482 nm) and trans bands ($\lambda_{max}$=510 nm). Another set of $\pi_{nb}$-$\pi^*$ transitions (HOMO to LUMO+1) is also predicted at a higher energy level ($\lambda_{max}$=376 and 353 nm for trans and cis, respectively) where a smaller band is clearly visible in the UV/vis spectrum (FIG. 2a), whereas the n-$\pi^*$ transition is, as predicted, at an even shorter wavelength ($\lambda_{max}$=338 nm for trans).

Figure 6:
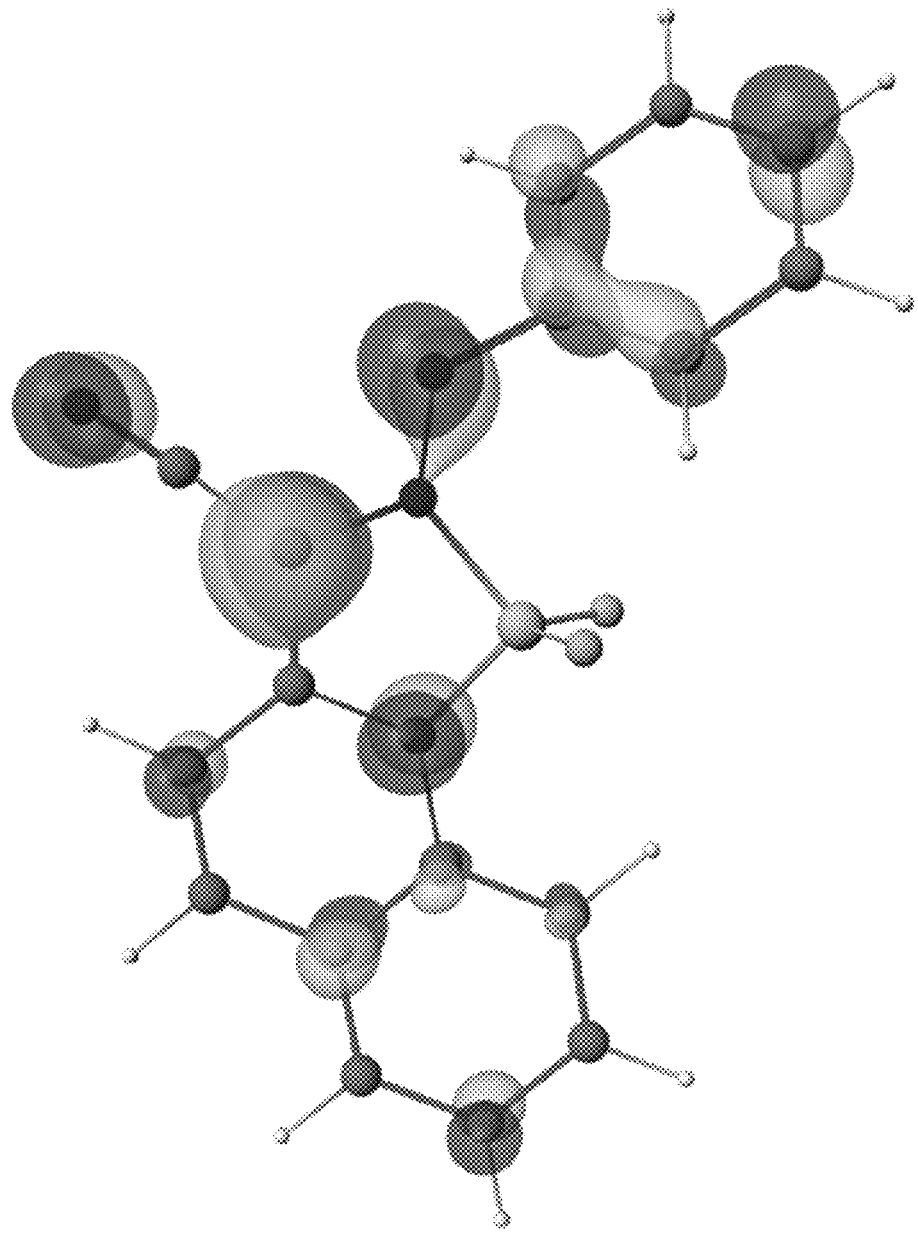
FIG. 6 shows the HOMO of Compound 1-trans (0.05 isosurface).
Figure 7:
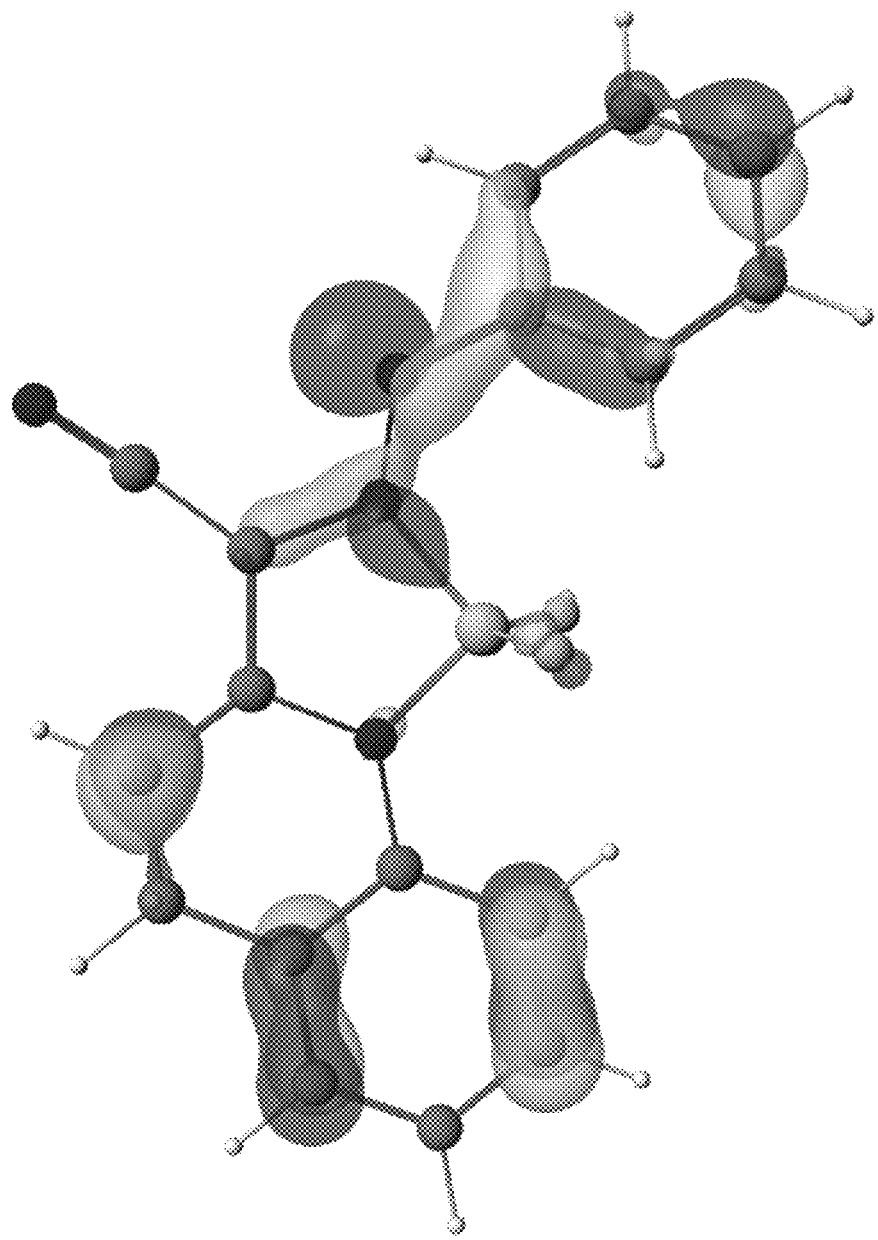
FIG. 7 shows the HOMO-2 of Compound 1-trans (0.05 isosurface).
Figure 10:
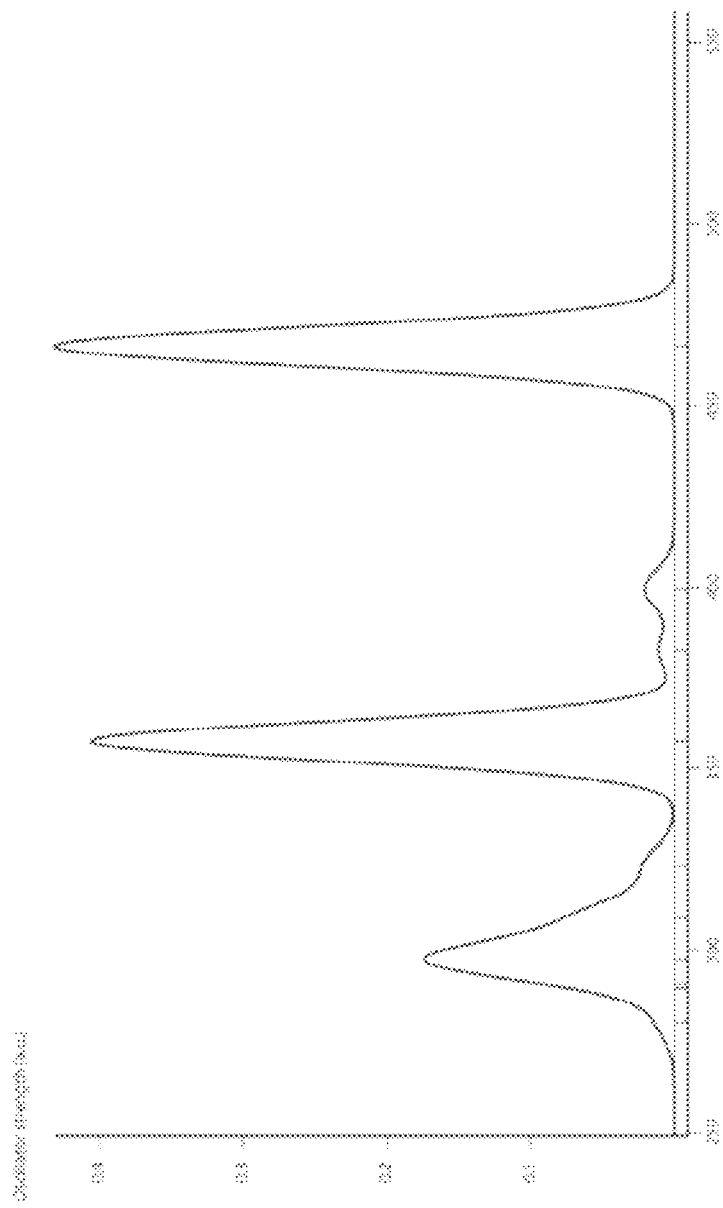
FIG. 10 shows the calculated UV/Vis spectrum of Na-Azo complex (trans).
Figure 11:
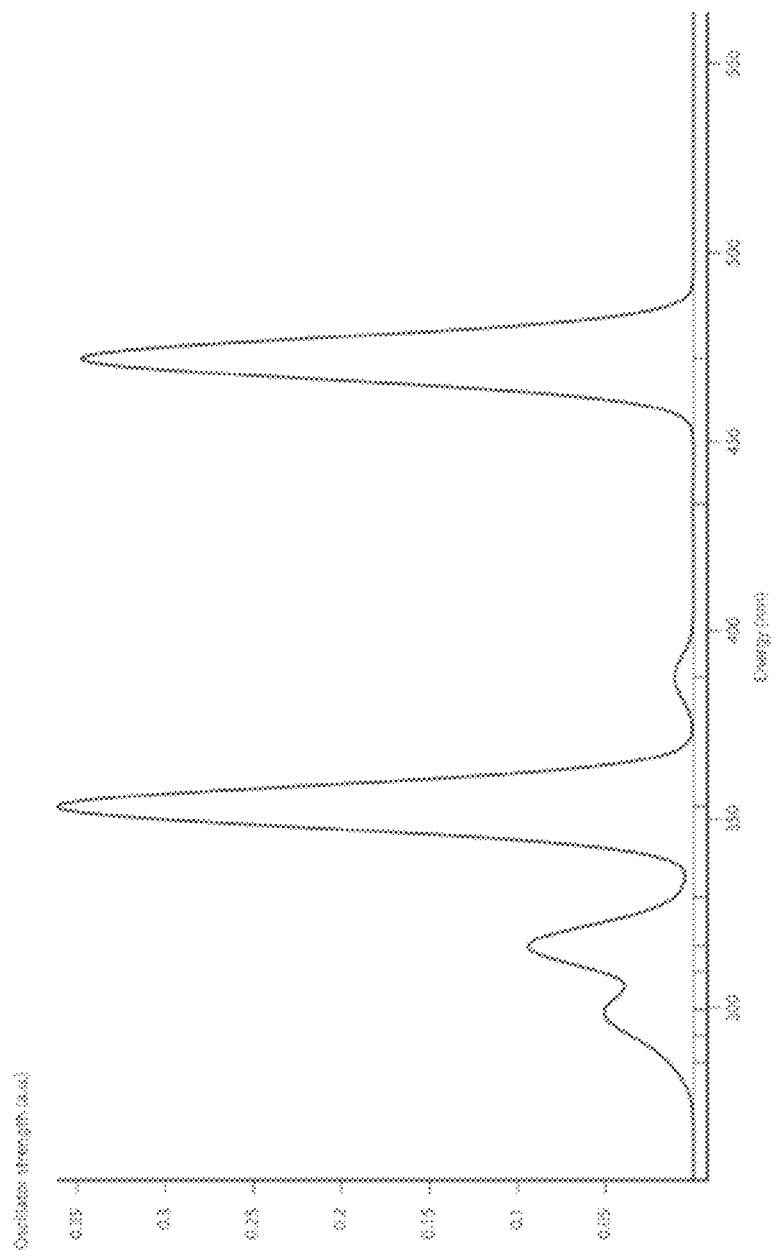
FIG. 11 shows the calculated UV/Vis spectrum of Na-Azo complex (cis).
Figure 12:
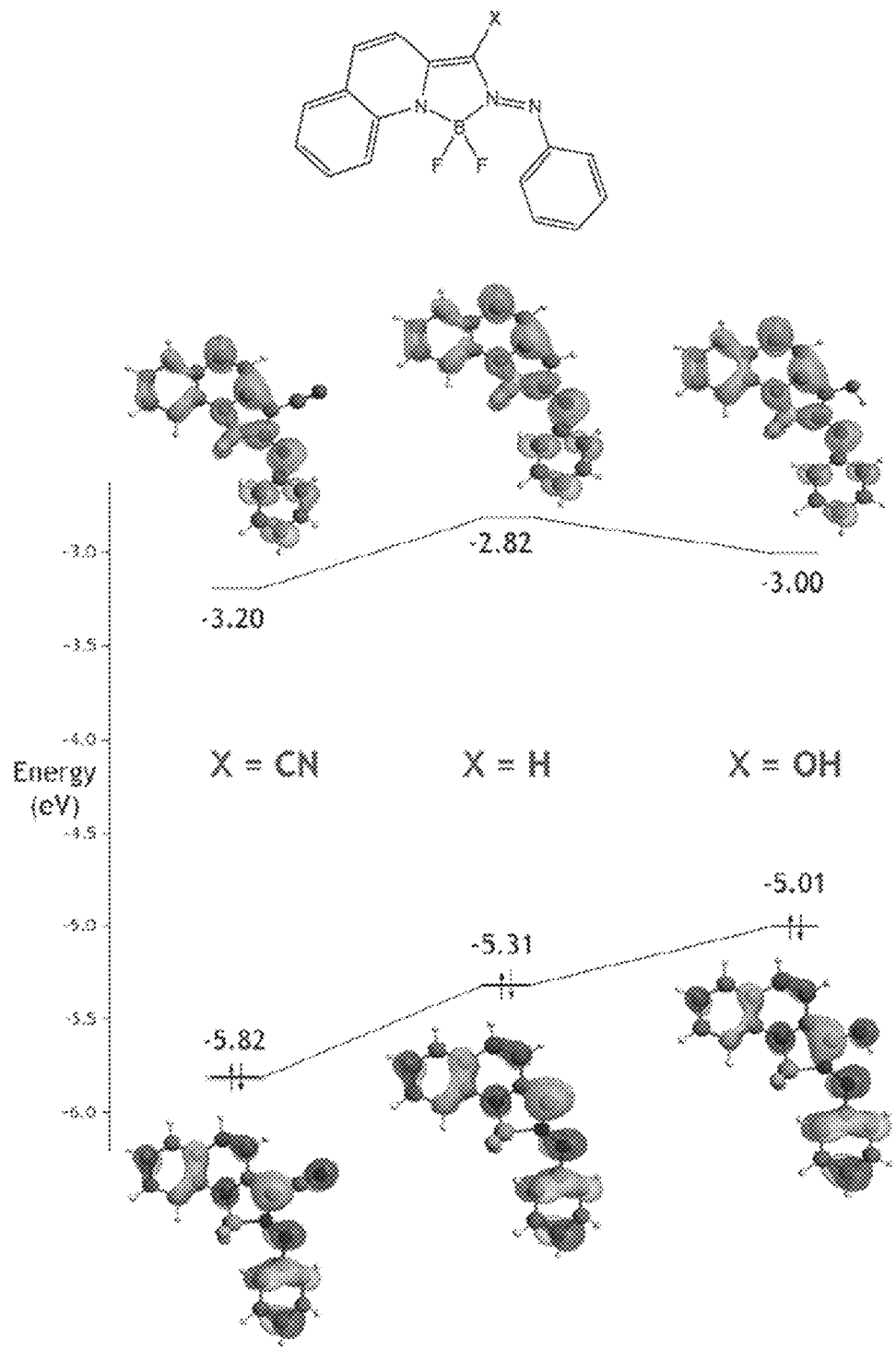
FIG. 12 shows the calculated substituent effects (X) on HOMO-LUMO energies of $BF_2$-Azo compounds. Substitution of H by the π-acceptor substituent CN decreases the HOMO-LUMO energy gap by stabilizing the HOMO more than the LUMO. Substitution of H by a π-donor OH substituent inductively stabilizes both HOMO and LUMO, but the π-donor component strongly destabilizes the HOMO, resulting in a lower overall HOMO-LUMO energy gap.
Figure 13:
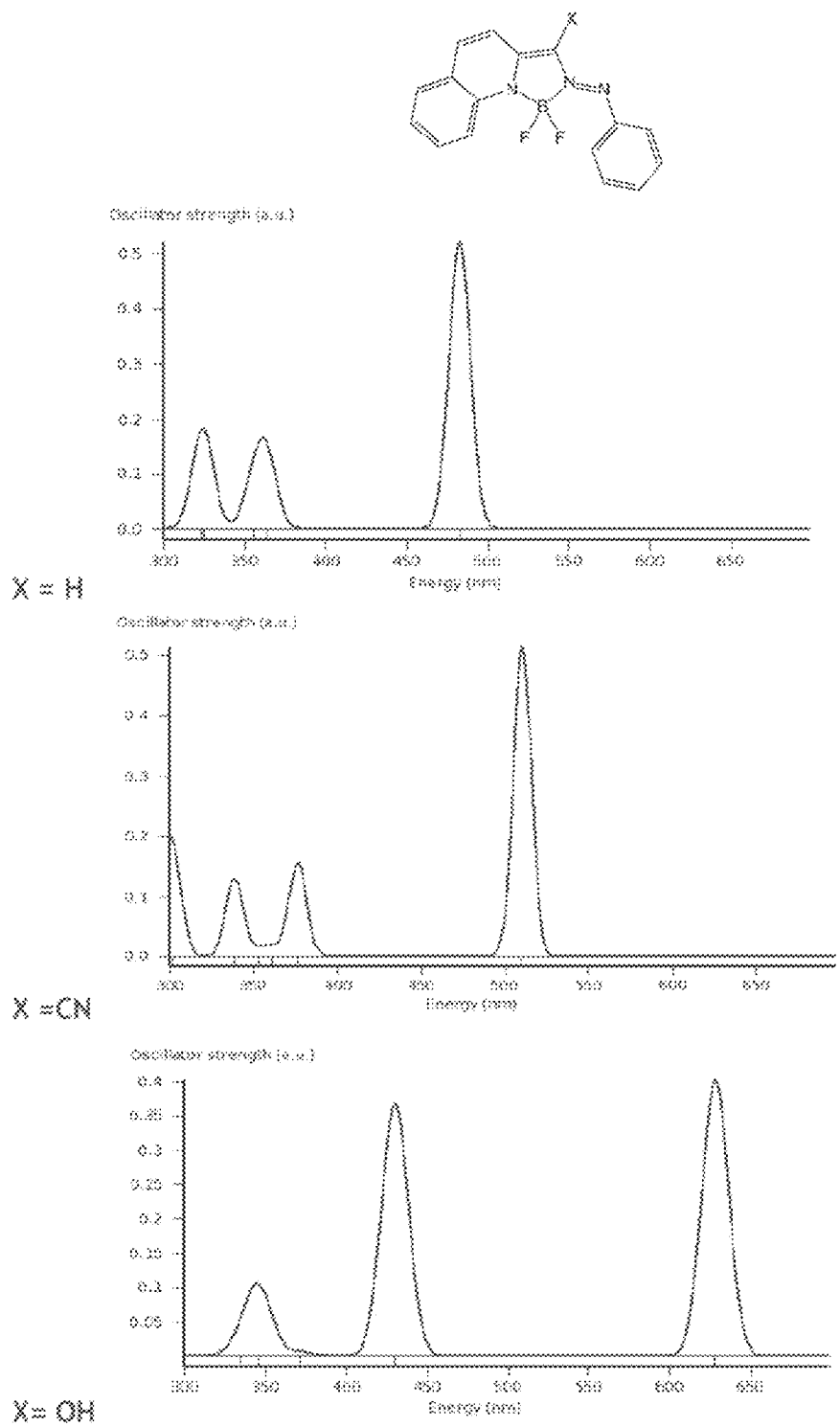
FIG. 13 shows the calculated substituent effects (X) on UV/Vis spectra of $BF_2$-Azo complexes (trans).
Figure 14:
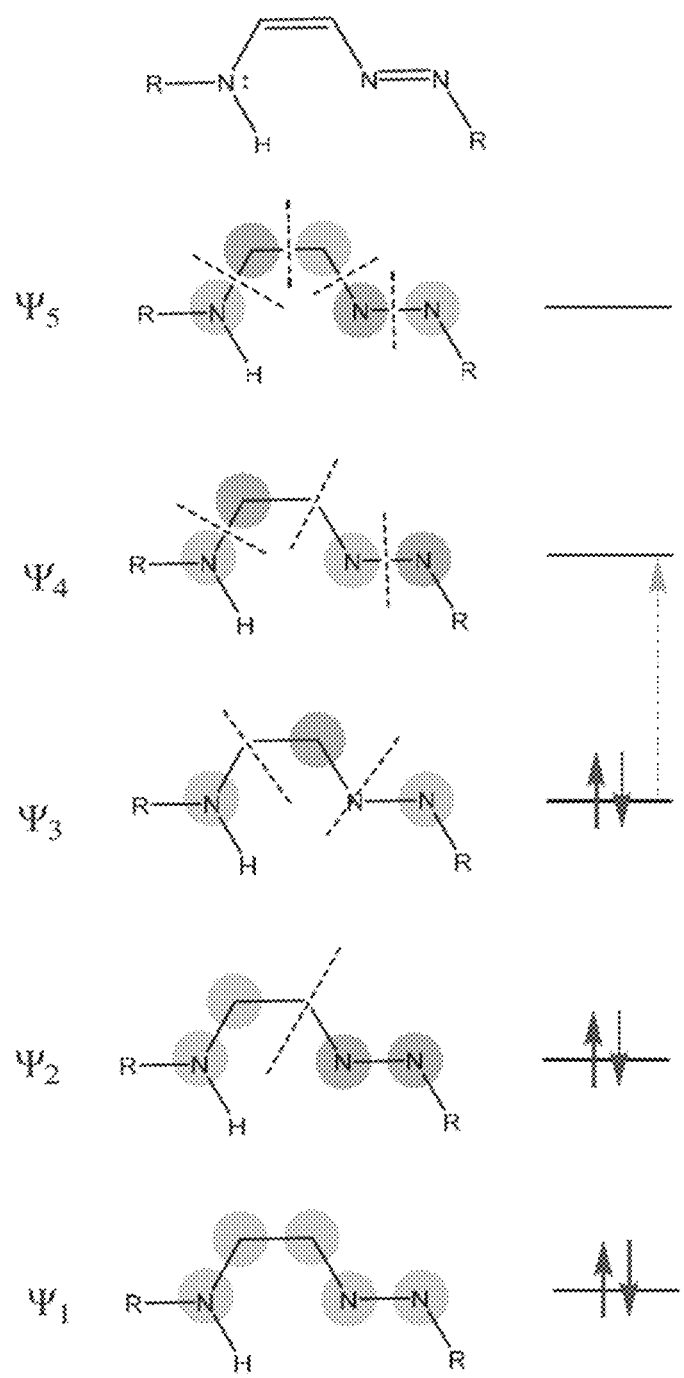
FIG. 14 depicts the idealized MO picture for the π-orbitals of the N—C—C—N—N skeleton of the azo compounds. Energies increase with the number of nodes. The HOMO→LUMO transition is from a MO that is π-nonbonding to one which is π*-antibonding between either the NN or CN subunits, as shown.
Figure 15:
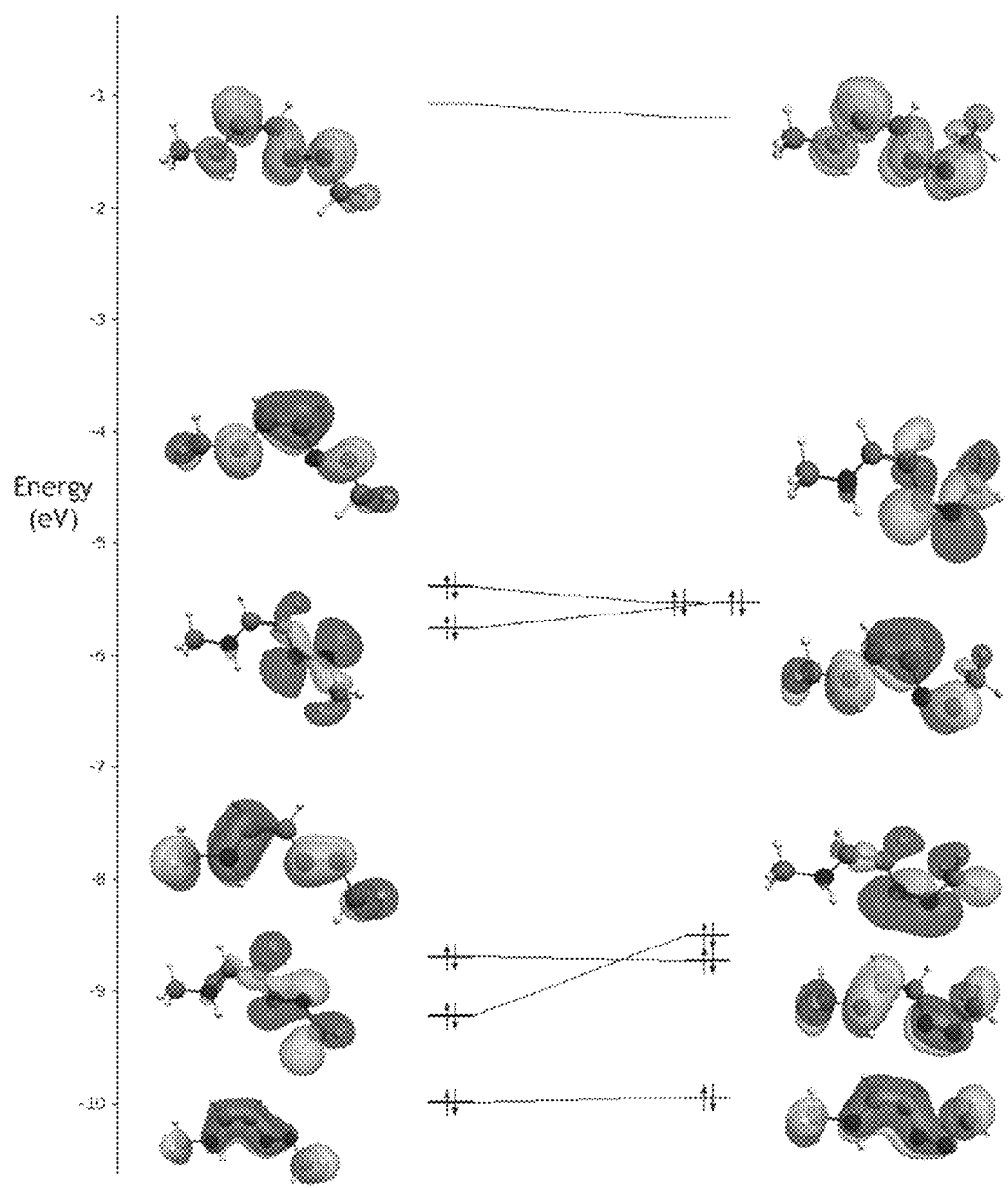
FIG. 15 demonstrates the H-Azo trans vs. cis MO levels: stripped molecules. The π-MOs follow the same nodal pattern as those in FIG. 14. Lone pair MOs rise in energy from trans→cis due to greater electron-electron repulsion in cis configuration.
Figure 16:
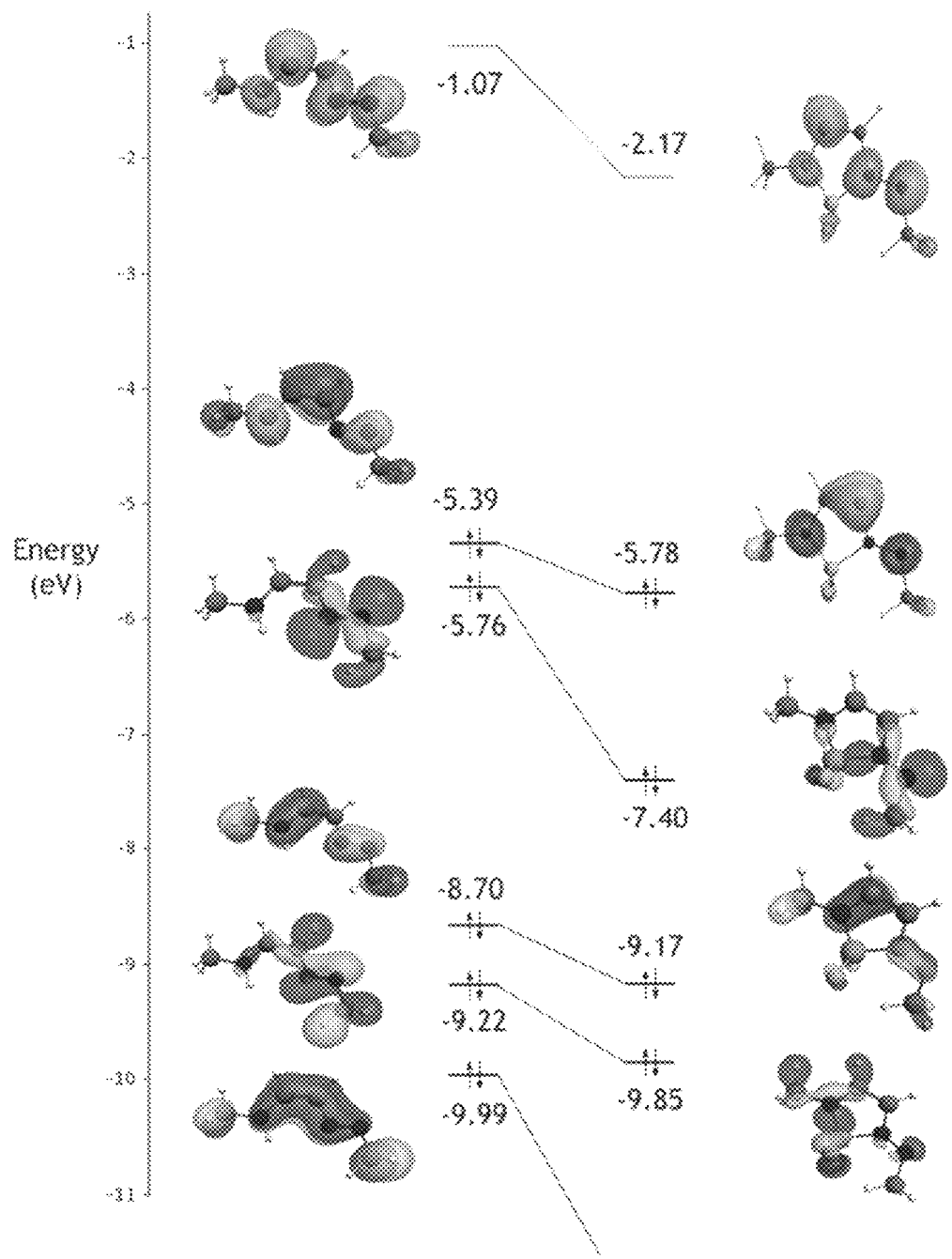
FIG. 16 demonstrates the H-Azo vs. $BF_2$-Azo MO levels: stripped molecules. $BF_2$ coordination lowers all energy levels by electron withdrawal; lone pair levels are lowered even more significantly by coordination and become bonding instead of non-bonding. The HOMO→LUMO transition is from an MO that is π-nonbonding to one which is π*-antibonding between either the NN or CN subunits. Unlike the H— compound, only the NN linkage is subject to trans→cis isomerization (switching) in the $BF_2$ compound; the rest of the system is clamped in position by coordination to the $BF_2$ group.
Figure 17:
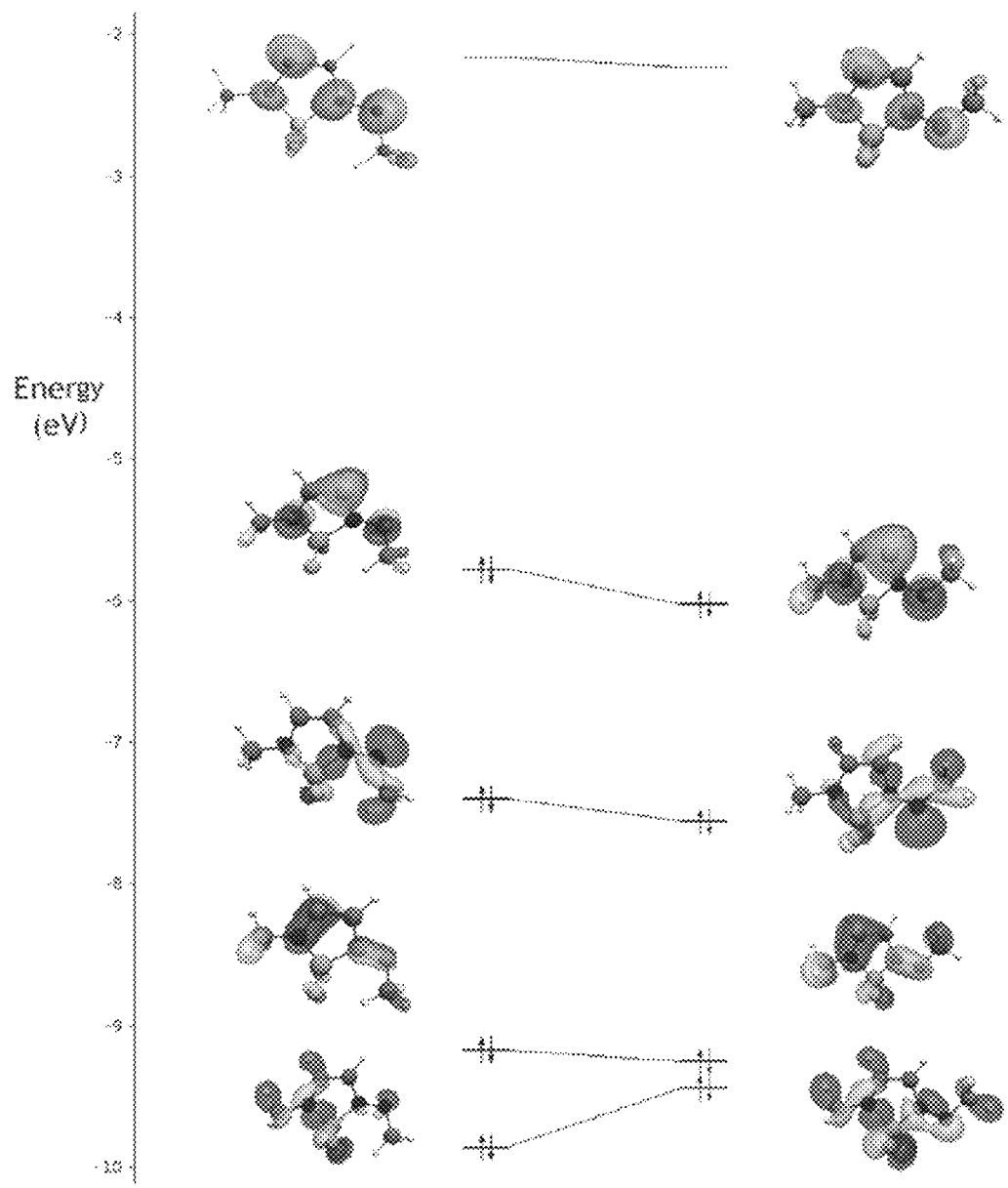
FIG. 17 shows the calculated $BF_2$-Azo trans vs. cis MO levels: stripped molecules. Higher energy HOMO→LUMO transitions in the cis isomer result from the stabilization of the HOMO in the latter, without significant stabilization of the corresponding LUMO.
Figure 18:
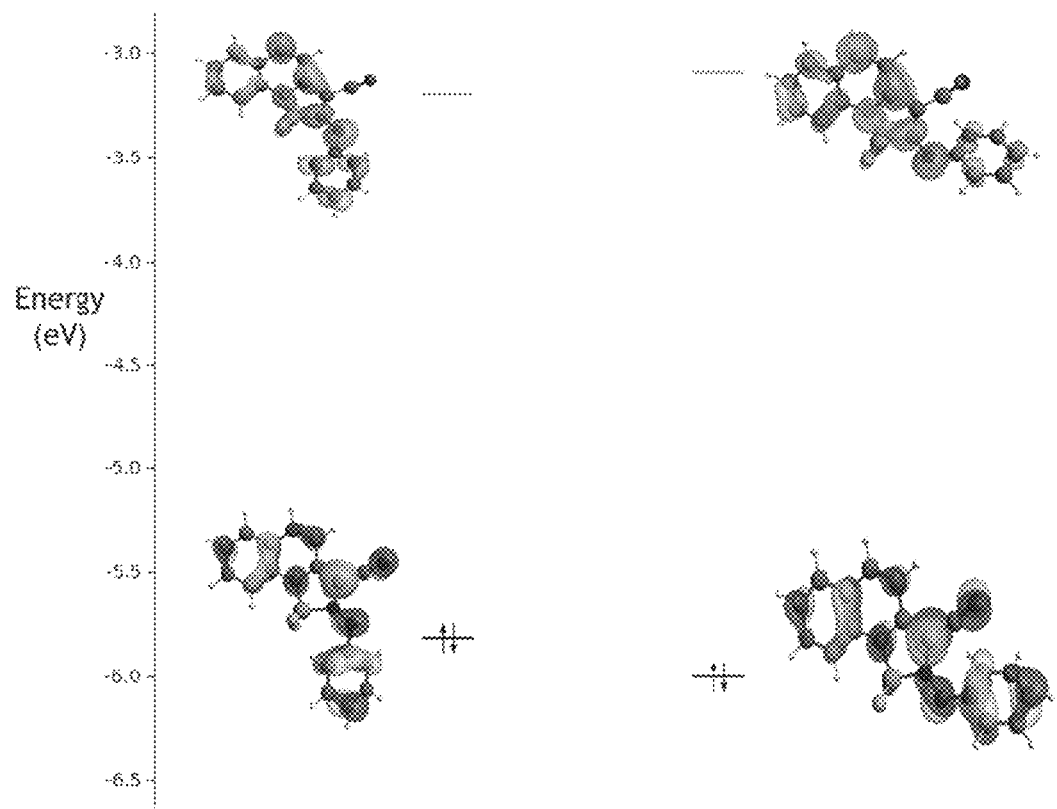
FIG. 18 depicts the $BF_2$-Azo trans vs. cis HOMO→LUMO levels: full molecules. Higher energy HOMO→LUMO transitions in the cis isomer result from the stabilization of the HOMO in the latter, without significant stabilization of the corresponding LUMO.
Figure 37:
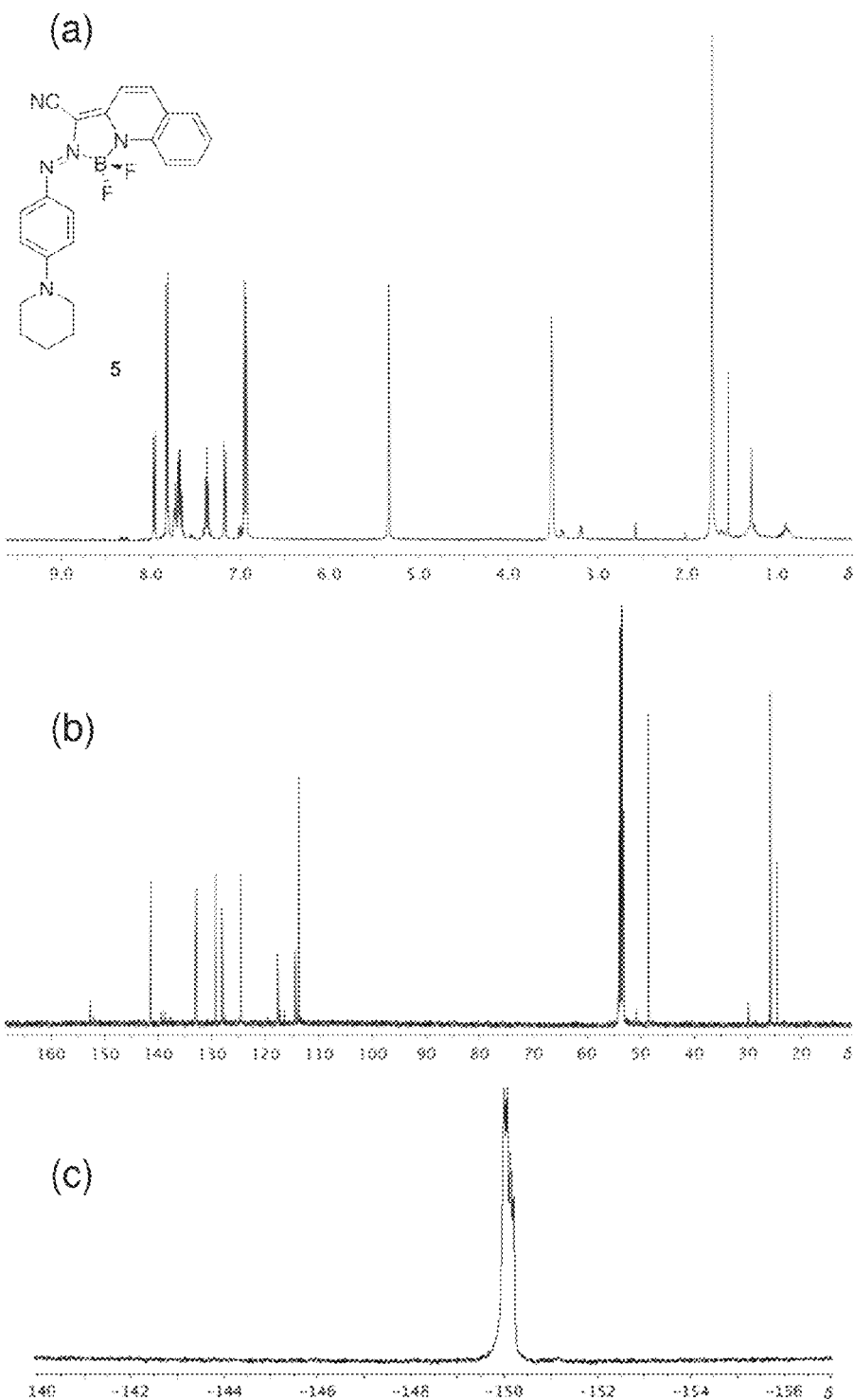
FIG. 37. a) $^1H$ NMR b) $^{13}C$ NMR and c) $^{19}F$ NMR spectra of 5-trans (contains a small percentage of the cis isomer) in $CD_2Cl_2$ at 294 K.

Relative to azobenzenes, binding to $BF_2$ drastically lowers the energy of the n-electrons, while additional conjugation in the N—C—C—N—N skeleton provides a higher energy $\pi_{nb}$ molecular orbital which serves as the HOMO (FIGS. 14-18S37-S41). This in turns leads to the strong absorption band in the visible range that enables the manipulation of Compound 1 using only visible light. The $BF_2$ group is not unique in promoting this effect. As a proof of concept, the $BF_2$ group was replaced with $Na^+$ (in silico), which also resulted in red-shifted UV/vis absorption spectra (FIGS. 10 and 11). Intriguingly, the trans and cis isomers have a $\lambda_{max}$ of 466 and 472 nm, respectively. Moreover, the calculations predict that replacing the CN group with $\pi$-electron donating groups (FIGS. 12 and 13) and/or substituting the phenyl ring with such groups (based on the HOMO in FIGS. 6-7) will lead to a red shift in the absorption band, opening the door for further manipulations of the photophysical properties of the azo compound.

NMR Photoisomerization Studies

Deoxygenated $CD_2Cl_2$ solutions of Compound 1 (8.8 mM) in quartz NMR tubes were used for all the $^1H$ NMR measurements. Irradiation of the samples was conducted with sufficient stirring. The lamp intensity at 450 nm was determined by chemical actinometry using potassium ferrioxalate and ferrozine while the intensity at 570 nm was determined by a Thorlabs optical power meter. The background thermal cis→trans isomerization was measured using $^1H$ NMR spectroscopy and no observable trans isomer was formed during the time period used in the irradiation experiments.

Photoisomerization Quantum Yields

The experimental procedure was adapted from Bandara et al. (J. Org. Chem. 2010, 75, 4817). After measuring the light intensities as mentioned above, the photoisomerization quantum yields were determined by following the change in isomer ratio after a certain period of irradiation time.

Kinetic Studies

A 0.2 mM deoxygenated $CH_2Cl_2$ solution of Compound 1 in a quartz cuvette was irradiated at 570 nm until its photostationary state was reached (no further changes in the UV/Vis spectra were observed). The thermal isomerization process was monitored by measuring the change in absorption intensity at 480 nm as a function of time (at 1 min intervals). The half-life ($t_{1/2}$) of the cis→trans isomerization was calculated to be 12.5 h, which is the average of three measurements conducted at the same conditions.

X-Ray Crystallography

Data were collected using a Bruker CCD (charge coupled device) based diffractometer equipped with an Oxford Cryostream low-temperature apparatus operating at 173 K. Data were measured using omega and phi scans of 1° per frame for 30 s. The total number of images was based on results from the program COSMO where redundancy was expected to be 4.0 and completeness to 0.83 Å to 100%. Cell parameters were retrieved using APEX II software and refined using SAINT on all observed reflections. Data reduction was performed using the SAINT software which corrects for Lp. Scaling and absorption corrections were applied using SADABS multi-scan technique, supplied by George Sheldrick. The structures are solved by the direct method using the SHELXS-97 and refined by least squares method on $F^2$, SHELXL-97, which are incorporated in SHELXTL-PC V 6.10. The structure of Compound 1 was solved in the space group $P2_1/c$ (#14). The aromatic ring was found to be disordered and was modeled at 50% in each position. The structure of Compound 1d was solved in the space group C2/c (#15). All non-hydrogen atoms were refined anisotropically. Hydrogens were calculated by geometrical methods and refined as a riding model. Crystals used for the diffraction studies showed no decomposition during data collection.

DFT Calculations

Computational Methods

All reported DFT calculations were carried out, without any symmetry constraints, using the robust hybrid B3LYP functional and the 6-311G**++ basis set, as implemented in the Jaguar suite of programs. Vibrational frequencies were calculated using analytic second derivatives, and all structures were confirmed as minima by the absence of imaginary frequencies. The allowed transitions in the UV spectra for the B3LYP optimized structures were carried out using TDDFT (B3LYP/TZ2P), as implemented in the ADF suite of programs.

Example 4: Near Infrared Light Activated Azo-$BF_2$ Switches

Light penetration through tissue is primarily regulated by the absorptions of hemoglobin and water,[1] which limits its "therapeutic window" to the 600-1200 nm range. In principle, the more red-shifted the wavelength the deeper the penetration, hence, near infrared (NIR) is far better than red light in this aspect.[2] One way of using this property of light is to couple it with photochromic[3] compounds that are capable of reversibly modulating biological processes. This is the main objective of the fields of photopharmacology[4] and opto(chemical)genetics.[5] Azo compounds[6] are the most commonly used light activated switches[7] in these research areas because of their efficient trans/cis photoisomerization. However, this process generally relies on UV light, which is not biocompatible.[8] Consequently, there has been intense activity in the field in trying to shift the activation wavelength of these photochromic compounds to the visible region,[9] and beyond. The burgeoning activity has led to the development of a number of visible light activated azo compounds, through appropriate derivatization,[10] or the use of metal to ligand charge transfer,[11] among other approaches.[12] This activity has recently paid off with the seminal work by Woolley et al. describing the in vivo activation of an azo compound using red light (635 nm).[10c] Despite these recent advances there is still a need to develop more efficient systems, and push the activation wavelength of the azo compounds beyond the red region, in order to gain access to deeper tissues.[13] In this context Qian et al. have recently showed[14] how NIR activated upconversion nanoparticles[15] can be used in manipulating azo compounds; however, this was accomplished using the NIR light indirectly, as the azo switch was still modulated using the UV light emitting from the excited nanoparticles. Furthermore the incorporation of nanoparticles complicates the system, and leads to low isomerization efficiencies, reducing the practicality of this approach in photopharmacology and opto(chemical) genetics.

The inventors discovered[16] that the coordination of $BF_2$ with an azo group's nitrogen lone-pair leads to a reversal of the positions of n-$\pi^*$ and $\pi$-$\pi^*$ transition energy levels. This property enabled switching of the azo-compounds using visible (i.e., blue and green) light. DFT calculations predicted that increasing the electron-density in the system could further red-shift the absorption bands, and hence activation wavelength of the system. A series of azo-BF$_2$ complexes having electron donating para- and ortho-substituents (Scheme 1) were designed.[17]

Scheme 1. Synthesis of ortho- and para-substituted BF$_2$-coordinated azo complexes.

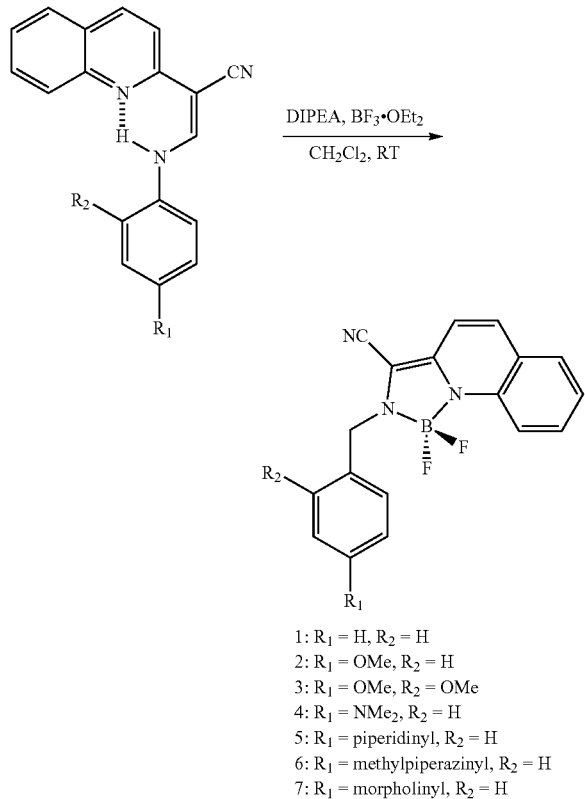

1: R$_1$ = H, R$_2$ = H
2: R$_1$ = OMe, R$_2$ = H
3: R$_1$ = OMe, R$_2$ = OMe
4: R$_1$ = NMe$_2$, R$_2$ = H
5: R$_1$ = piperidinyl, R$_2$ = H
6: R$_1$ = methylpiperazinyl, R$_2$ = H
7: R$_1$ = morpholinyl, R$_2$ = H This example reports how such substituents shift the azo-BF$_2$ absorption bands to the red and even NIR region, thus enabling direct and efficient isomerization of an azo-compound using NIR light. These systems are also stable to glutathione reduction, and have relatively long lived half lives in aqueous solutions.

As predicted by DFT calculations the introduction of a methoxy group para to the azo linkage (Scheme 2) leads to a bathochromic shift in the π-π* band of 2 ($\lambda_{max}$=594 nm, ε=15,998 M$^{-1}$ cm$^{-1}$).

Scheme 2. Visible light-induced trans/cis isomerization of 2.

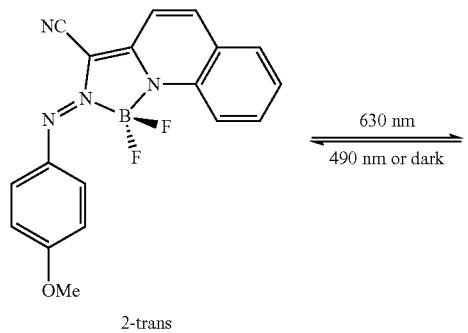

2-trans

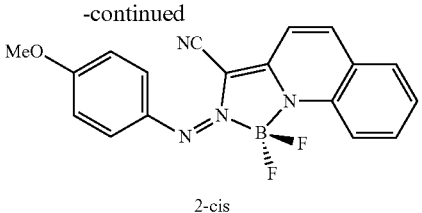

2-cis

Figure 26:
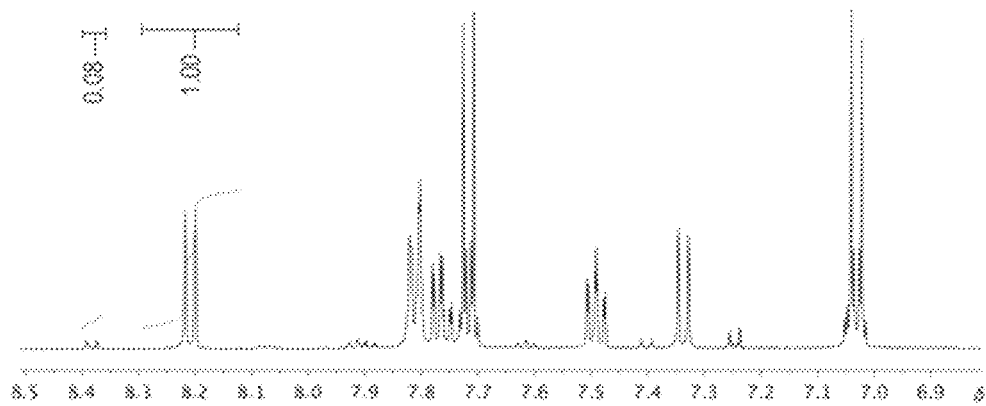
FIG. 26. $^1H$ NMR spectrum of 2 after being stored in the dark. The equilibrated mixture of 2 was determined to have an isomer ratio of 93:7 (trans:cis).
Figure 27:
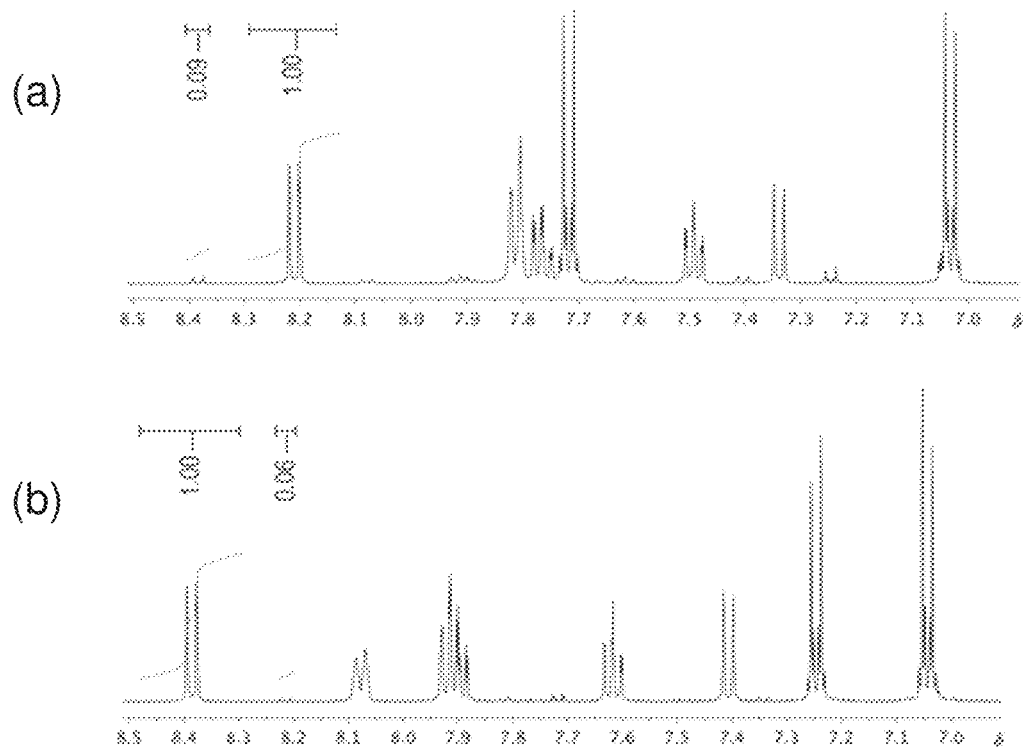
FIG. 27. $^1H$ NMR spectra of the PSS of 2 at a) 490 nm and b) 630 nm in $CD_2Cl_2$ at 294 K. The PSS isomer ratios of 92±1% trans at $\lambda_{irr}$=490 nm, and 96±1% cis at $\lambda_{irr}$=630 nm are the averages of three experiments.

The $\lambda_x$ of the cis photostationary state (PSS; irradiation at 630 nm) of compound 2 is red-shifted by 40 nm (FIG. 19a), while the trans PSS (irradiation at 490 nm) is red-shifted by 55 nm compared with the parent complex 1.[16] The switching process of 2 was accompanied with a strong color change between cobalt blue and poppy red. High photoconversion ratios (PSS490=92% trans, PSS630=96% cis) and a 93% trans isomer ratio under dark were determined for 2 using $^1$H NMR spectroscopic analysis (FIGS. 27 and 26). There are several spectral features of 2 that set it apart from the parent compound; instead of a sharp band, the π-π* band of the trans-dominant state exhibits a well resolved vibrational fine structure, with the highest-intensity peak observed at $\lambda_{max}$=594 nm. The appearance of the sub-bands can be attributed to the intensified vibrational transitions caused by the electron-donating para-substituent.[18] In addition, the isomerization process in 2 is more efficient than 1 based on its quantum yields ($\Phi_{trans \to cis}$=71% and $\Phi_{cis \to trans}$=95%). This efficiency enhancement results from a better separation of the cis and trans states' π-π* bands, which leads to less overlap of their irradiation windows compared to the parent azo complex 1. The cis isomer of 2 has a half-life of 10.4 h at 294 K in deoxygenated methylene chloride (FIG. 48), compared to 25 min in regular solvent (not deoxygenated).[16, 1]

Scheme 3. Visible light-induced trans/cis isomerization of 3.

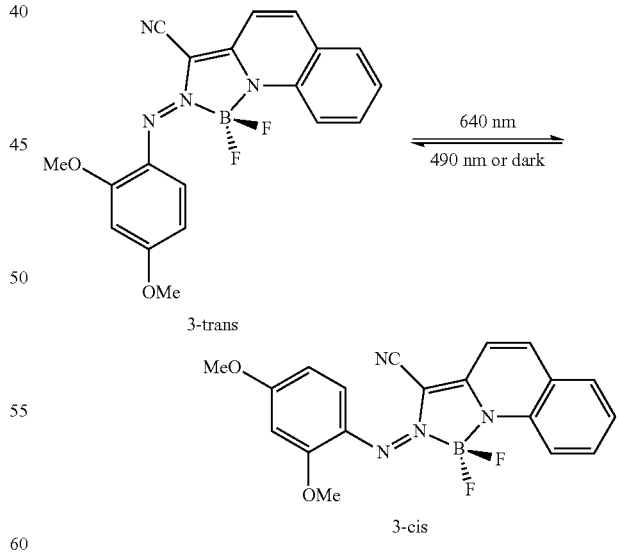

It was recently shown[10b] that ortho-tetrafluoroazobenzene has a slightly blue shifted π-π* absorption when compared to its parent azobenzene, and that the substitution of the ortho positions with methoxy groups[10a] leads to the separation of the n-π* orbital of the cis and trans isomers and a red-shift of the π-π* band in the latter. In order to study the ortho-substitution effect, complex 3 (Scheme 3) was prepared. The extra ortho-methoxy group in 3 causes a 20 nm blue shift of its trans absorption band relative to 2 (FIG. 19b). On the other hand, its cis isomer's π-π* band is red-shifted by 15 nm. The combined effect is the generation of a pronounced overlap between the absorption bands of the two configurations. This overlap resulted in a drastic decrease in the efficiency of the switch, including its PSS ratio (PSS490=56% and PSS640=79%) and photoswitching quantum yields ($\Phi_{cis \rightarrow trans}$=51% and $\Phi_{trans \rightarrow cis}$=42%). The steric hindrance of the ortho-OMe group may destabilize the trans isomer, and prevent the phenyl ring from lying coplanar with the rest of the molecule. The loss of planarity in the trans isomer can be inferred by its blue-shifted absorption band, and its destabilization is evident from the lower trans isomer ratio (58%) under dark.

Figure 49:
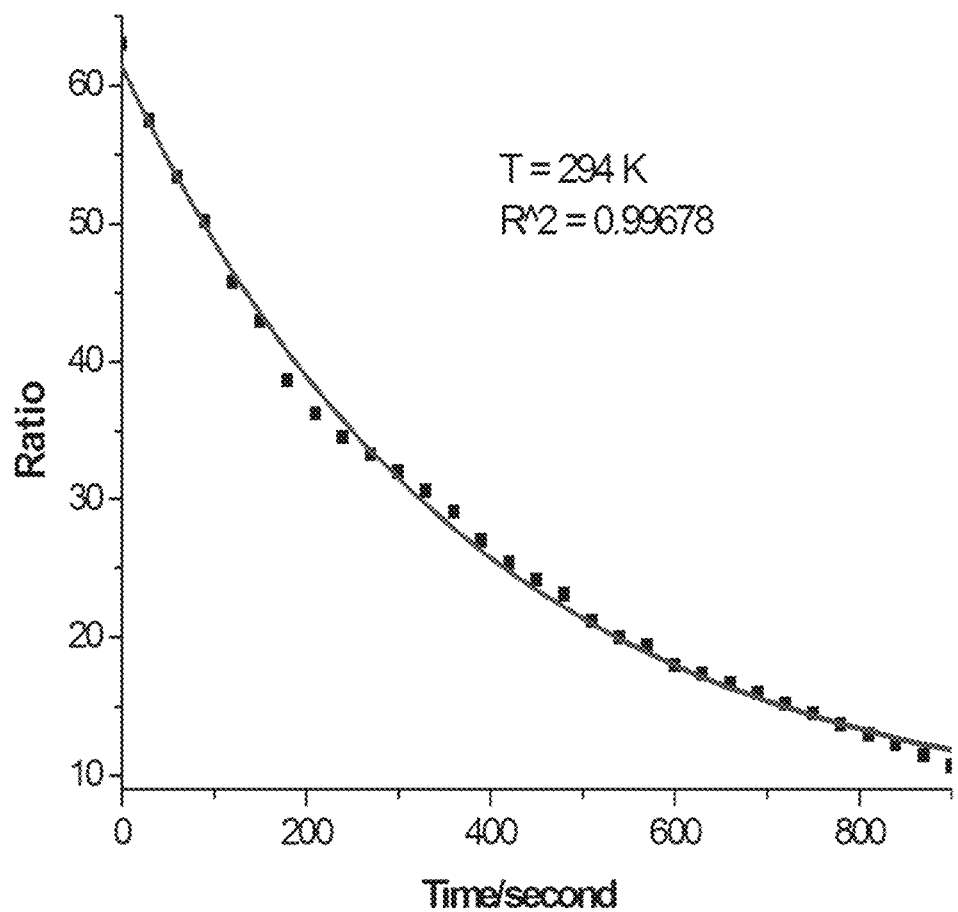
FIG. 49. Plots of cis isomer ratio (%) versus time showing the first-order decay of 4 in $CD_2Cl_2$ at 294 K starting from its PSS710. The black dots represent the experimental results while the red line represents the theoretical first-order fit.

The $BF_2$-Azo complexes (4-7) were synthesized with the intention of further pushing the activation wavelength of the systems to even lower energy levels. The attachment of a para-dimethylamino group shifted the absorption peak of complex 4 to 680 nm ($\epsilon$=36,255 $M^{-1}$ $cm^{-1}$) with a tail extending out to 760 nm (FIG. 20). This property allowed the trans to cis isomerization process to be activated using NIR light. The UV/Vis spectrum of the trans isomer of 4 exhibits better-resolved vibrational fine structure compared to 2. The half-life of the cis isomer of 4 was determined to be 250 seconds (FIG. 49), and no obvious difference in rate was observed by deoxygenating the methylene chloride solution. The effective bond order of N=N bond is strongly influenced by the substituents on the phenyl rings (vide infra). Electron-donating groups would cause an increase in the electron density of the π* (antibonding) orbital and thus a decrease in the effective bond order of the N=N bond, which leads to a lower thermal isomerization barrier.[6,20] Under dark, complex 4 is almost quantitatively (97%) composed of the thermodynamically more stable trans form. Upon irradiation with 710 nm light, isomerization to the cis isomer occurs quickly. Because of the fast cis to trans isomerization rate we were unable to record the PSS at 710 nm. The lowest estimation of the amount of cis isomer at PSS710 is 63% based on $^1$H NMR spectroscopy (FIG. 35).[21]

The isomerization and photochromic properties of the piperidinyl (5), methylpiperizinyl (6), and morpholinyl (7) $BF_2$-azo derivatives were studied (FIG. 21). As can be seen by their UV/Vis spectra, these switches all undergo isomerization upon irradiation with 710 nm light, and maintain a high ratio of trans isomer under dark (98%, 94% and 97% trans ratio, with molar extinction coefficient $\epsilon$=30,458, 29,536 and 28,025 $M^{-1}$ $cm^{-1}$, for 5, 6 and 7, respectively). The small variation in the electronic characteristics of the amino groups greatly impacts their photophysical properties, including their absorption bands and half-lives. The overlay of the absorption bands of compounds 5-7 (FIG. 21d) reveals that the resolution of their vibrational fine structure decreases in the order of 5>6>7, which is in accordance to their para-substituent's electron-donating ability (piperidinyl>methylpiperizinyl>morpholinyl).[22] A similar trend is also observed in their absorption maxima ($\lambda_{max}$=681 nm, 661 nm and 652 nm for 5, 6 and 7, respectively). In addition, the half-life relaxation rate from cis to trans is substantially enhanced in switch 7 ($t_{1/2}$=900 s) as compared to 5 ($t_{1/2}$=150 s) and 6 ($t_{1/2}$=400 s), which is again in accordance to their electron donation capability. Such a dramatic change in the half-life of these switches was also reflected by their PSS710 values. The highest PSS710 ratio for 5 that could be measured was 23% while for 6 and 7 it was 49% and 83%, respectively. The latter value is comparable to that obtained for the parent azo-$BF_2$ complex 1.

Figure 51:
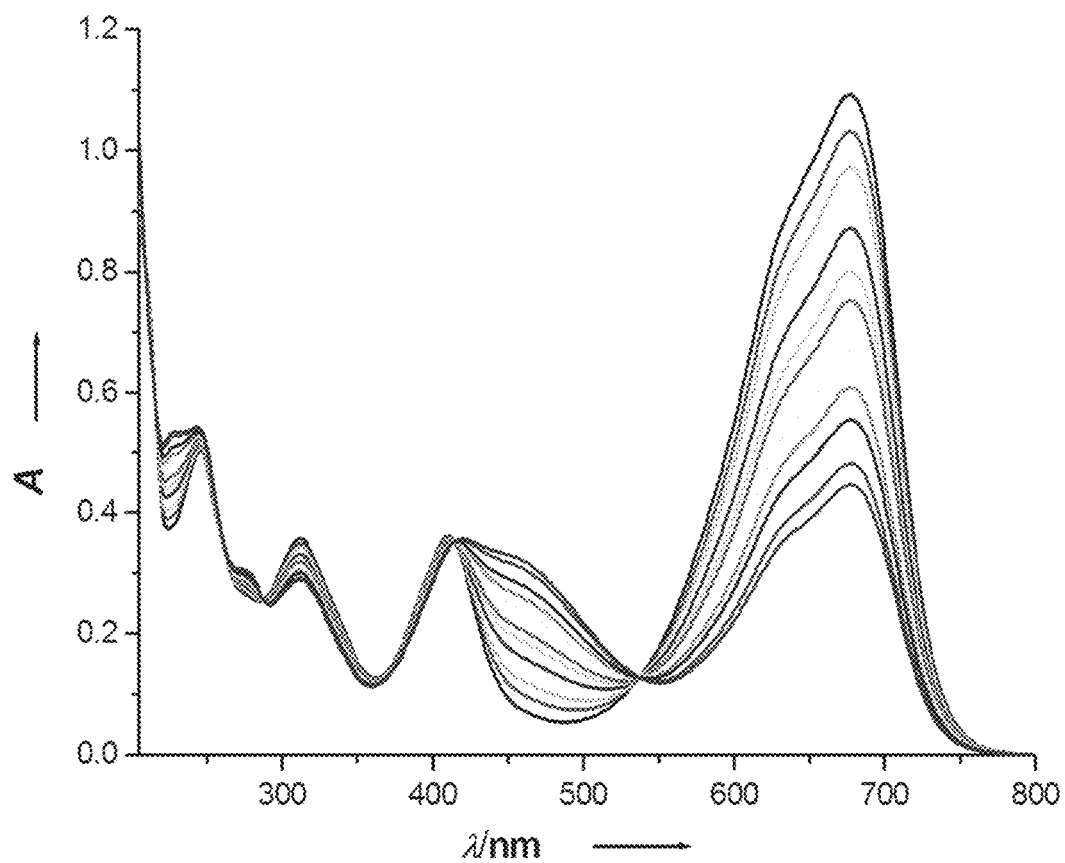
FIG. 51. UV-Vis spectra following an acetonitrile:PBS (1:1) solution of 4 incubated with 10 mM GSH at 25° C. The interval between each scan is ~20 min. A half-life of 2.5 h is observed.
Figure 52:
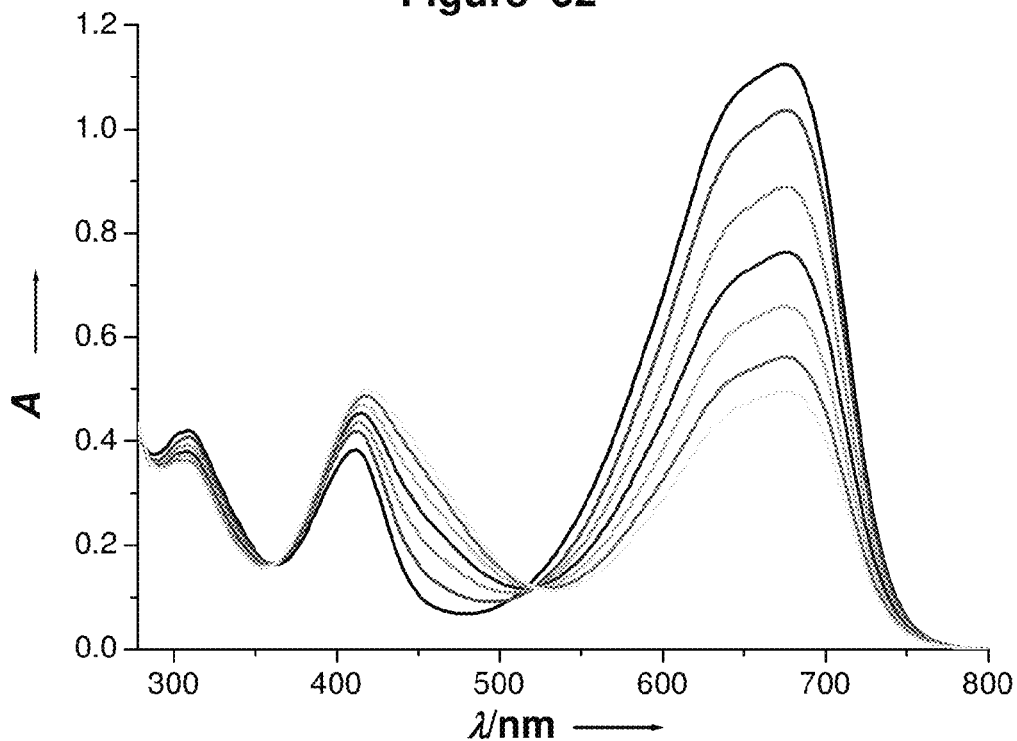
FIG. 52. UV-Vis spectra following an acetonitrile:PBS (1:1) solution of 5 at 25° C. The interval between each scan is ~20 min. A half-life of 2 h is observed.
Figure 53:
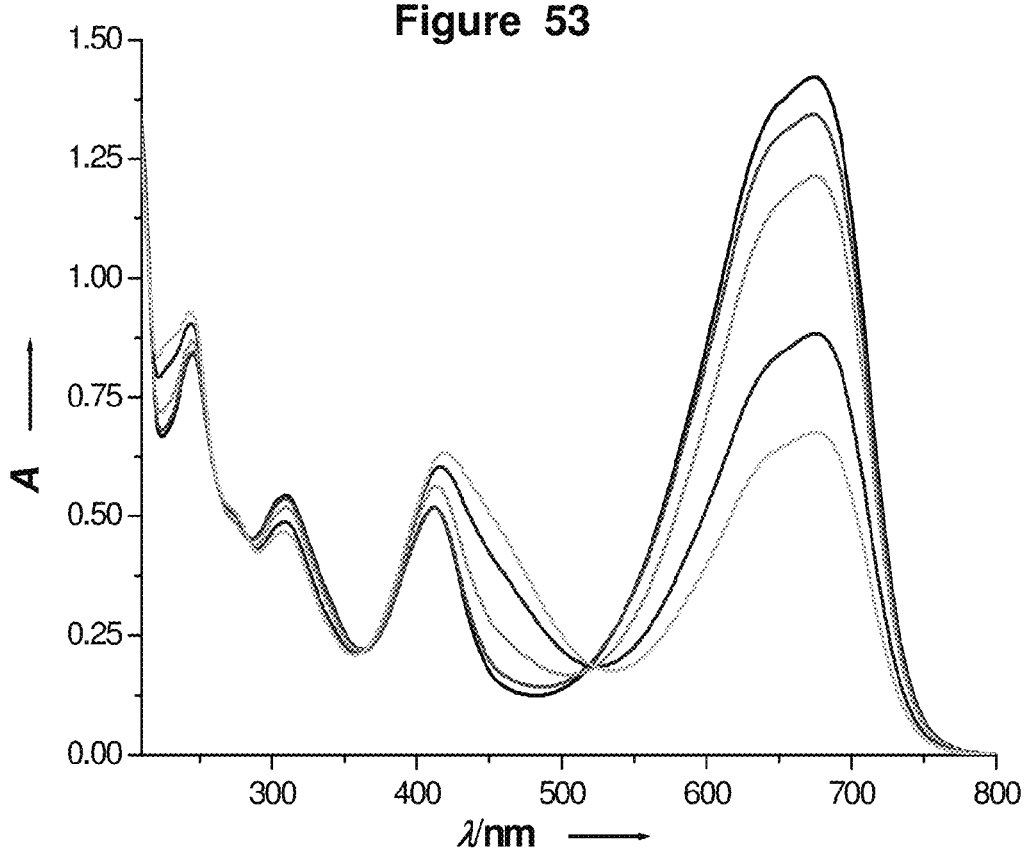
FIG. 53. UV-Vis spectra following an acetonitrile:PBS (1:1) solution of 5 incubated with 10 mM GSH at 25° C. The interval between each scan is ~20 min. A half-life of 2.1 h is observed.
Figure 54:
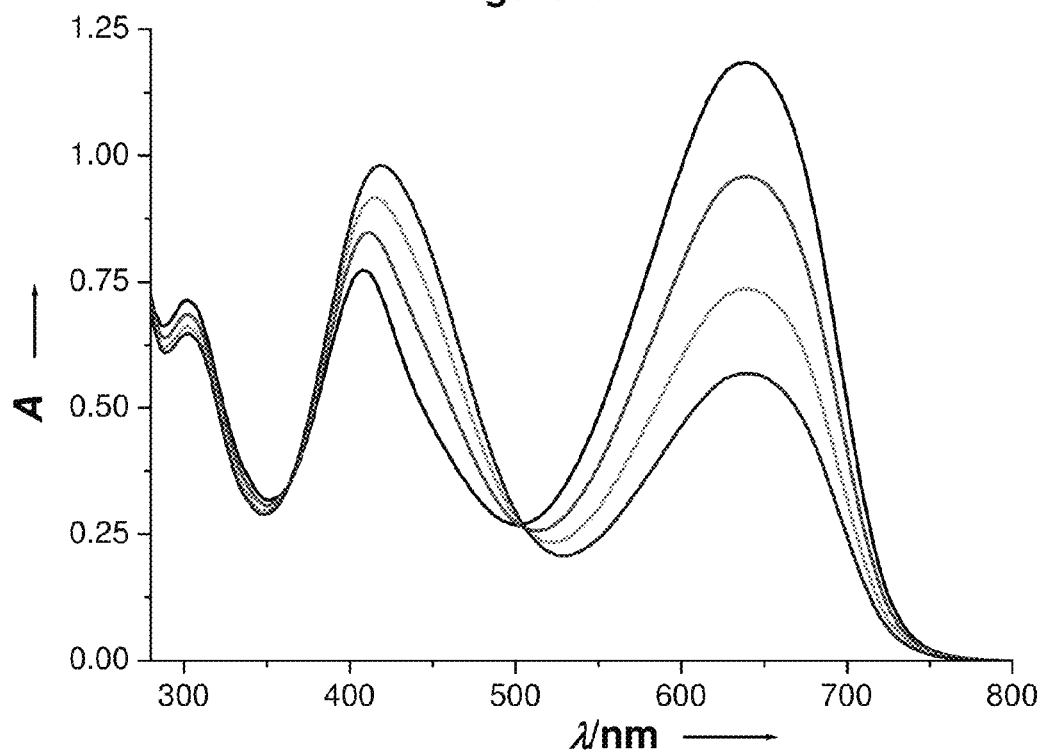
FIG. 54. UV-Vis spectra following an acetonitrile:PBS (1:1) solution of 6 at 25° C. The interval between each scan is ~20 min. A half-life of 1.2 h was observed.
Figure 55:
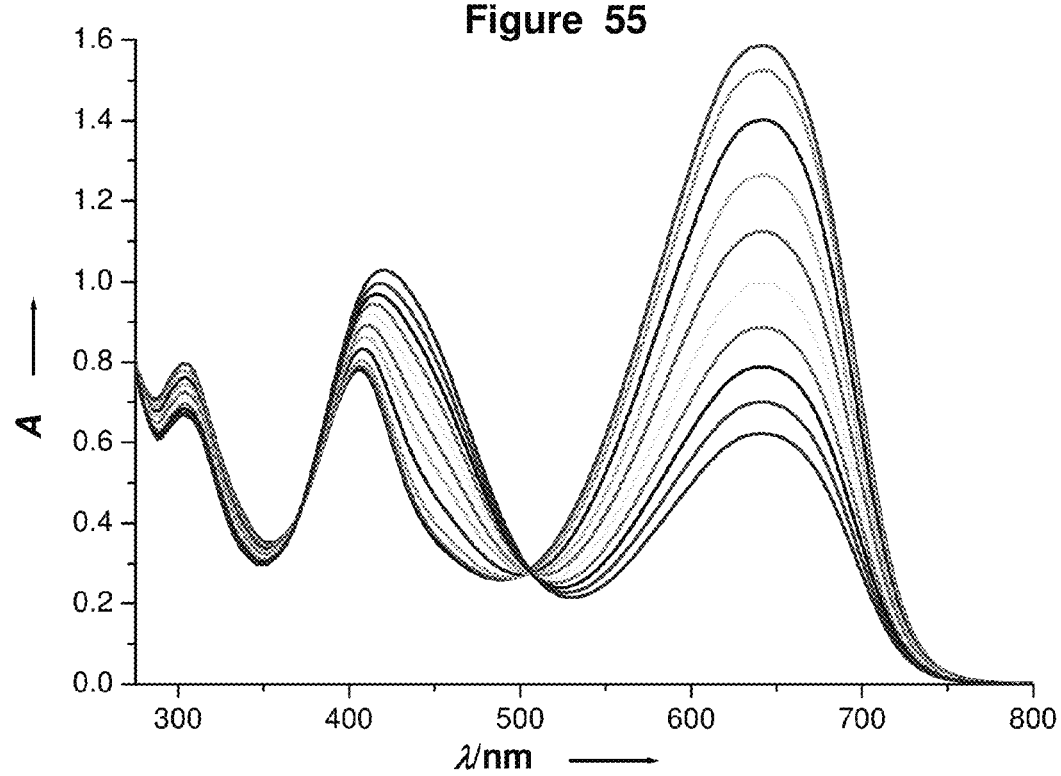
FIG. 55. UV-Vis spectra following an acetonitrile:PBS (1:1) solution of 6 incubated with 10 mM GSH at 25° C. The interval between each scan is ~10 min. A half-life of 1.3 h was observed.
Figure 56:
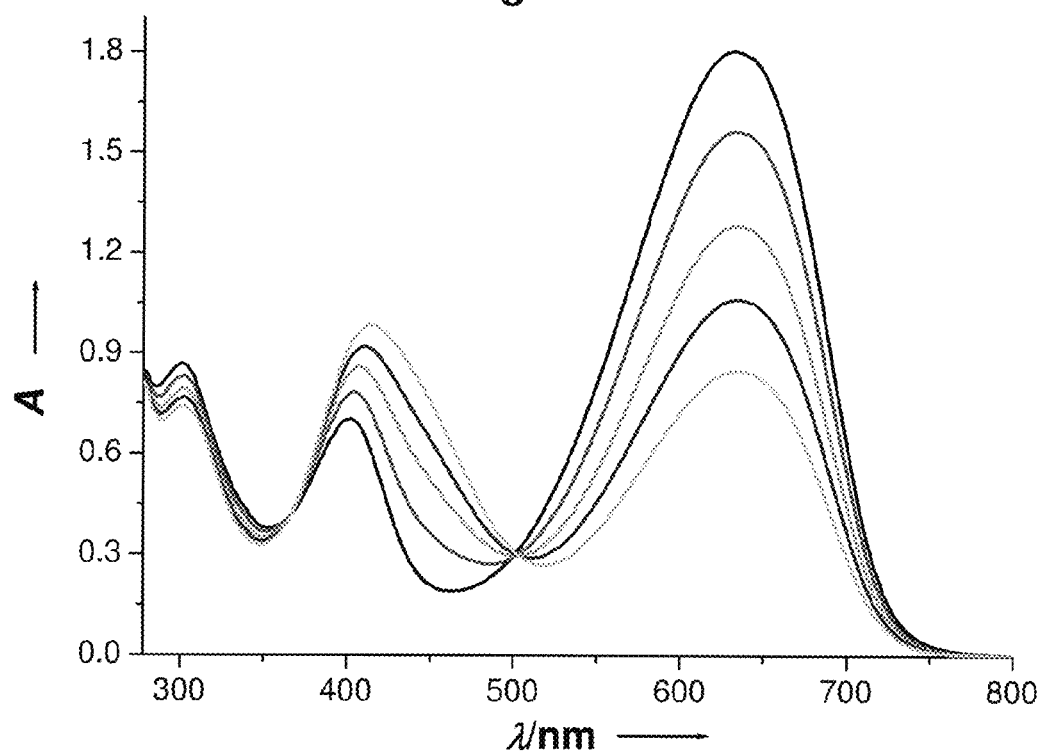
FIG. 56. UV-Vis spectra following an acetonitrile:PBS (1:1) solution of 7 at 25° C. The interval between each scan is ~20 min. A half-life of 0.9 h was observed.
Figure 57:
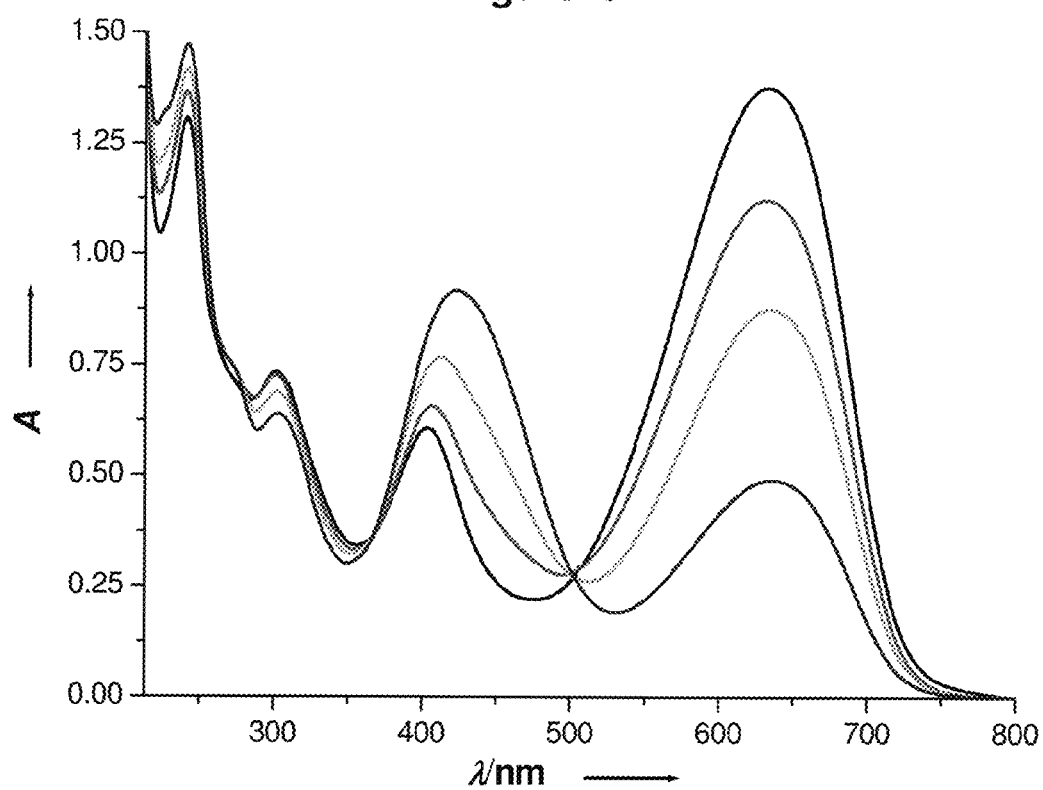
FIG. 57. UV-Vis spectra following an acetonitrile:PBS (1:1) solution of 7 incubated with 10 mM GSH at 25° C. The interval between each scan is ~25 min. A half-life of 1.0 h was observed.

The stability of the switches in an aqueous environment was tested by conducting multiple switching cycles (10 cycles shown in FIG. 22a) of 4 in an acetonitrile:PBS buffer (1:1) mixed solvent system. These experiments were conducted by irradiating the sample using 710 nm light, followed by thermal relaxation under dark. Although switch 4 is stable for short periods of time under these conditions, it gradually undergoes hydrolysis (FIG. 50), reverting back to the starting hydrazone[23] compound (FIG. 22b) with a half-life of 2.3 h. The stability of switch 4 to reduction by glutathione (GSH) was also tested. The switch was incubated in 10 mM reduced glutathione in acetonitrile:PBS buffer (1:1) solution. No obvious difference was observed in its degradation half-life ($t_{1/2}$=2.5 h) compared to that measured in the acetonitrile/PBS buffer (FIG. 51). The multiple isosbestic points observed in both cases ($\lambda$=286 nm, 413 nm and 537 nm) suggest the existence of only two species in solution, which in this case are the azo-$BF_2$ complex and the hydrazone starting material. These results, along with similar stability tests conducted for compounds 5-7 (FIGS. 52-57), demonstrate the robustness of this class of NIR switches in high concentrations of GSH. Moreover, the results indicate that coordination with $BF_2$ might be a viable strategy to preventing glutathione reduction of azo compounds.

By comparing the degradation half-life of the complexes in PBS buffer (4≈5>6>7), it is possible to conclude that the higher electron-donating ability of the para-substituent, the more stable the switch is to hydrolysis. According to the crystallographic analysis (FIG. 23), the stronger the electron-donating capability of the para-substituent the longer the N(1)=N(2) bond (1.294(1) and 1.298(2) Å in 2 and 4, respectively) and shorter the B(1)-N(3) bond and B(1)-N(2) bond lengths become (1.550(2) and 1.624(2) Å in 2, and 1.542(2) and 1.615(2) Å in 4, respectively). The latter trend (i.e., the strengthening of the BN bonds) may make the compounds less susceptible to hydrolysis.

In conclusion, this example shows how the para-substitution of azo-$BF_2$ compounds with electron donating groups leads to photochromic compounds that can be activated with NIR light. Structure property analysis showed that the hydrolysis process in these systems can be modulated and slowed down using strong electron donating para-substituents. Moreover, these switches are not susceptible to reduction by glutathione, most probably because of the coordination with $BF_2$. These results open the way for using these $BF_2$-coordinated azo compounds in photopharmacolgical[4] and opto(chemo)genetical applications.

REFERENCES (1) Kalka, K.; Merk, H.; Mukhtar, H. *J. Am. Acad. Dermatol.* 2000, 42, 389-413.
(2) Smith, K. C., Ed. *The Science of Photobiology*; Plenum Press: New York, 1977.
(3) (a) Irie, M. *Chem. Rev.* 2000, 100, 1683-1684. (b) Durr, H.; Bouas-Laurent, H., Eds. *Photochromism: Molecules and Systems*; Elsevier: Amsterdam, 2003.
(4) Velema, W. A.; Szymanski, W.; Feringa, B. L. *J. Am. Chem. Soc.* 2014, 136, 2178-2191.
(5) Sjulson, L.; Miesenbçck, G. *Chem. Rev.* 2008, 108, 1588-1602. (b) Fehrentz, T.; Schönberger, M.; Trauner, D. *Angew. Chem. Int. Ed.* 2011, 50, 12156-12182. (b) Brieke, C.; Rohrbach, F.; Gottschalk, A.; Mayer, G.; Heckel, A. *Angew. Chem. Int. Ed.* 2012, 51, 8446-8476.

(6) Bandara, H. M. D.; Burdette, S. C. *Chem. Soc. Rev.* 2012, 41, 1809-1825.
(7) (a) Kay, E. R.; Leigh, D. A.; Zerbetto, F. *Angew. Chem. Int. Ed.* 2007, 46, 72-191. (b) Balzani, V.; Credi, A.; Venturi, M. *Molecular Devices and Machines—Concepts and Perspectives for the Nanoworld;* Wiley-VCH: Weinheim, 2008. (b) Stoddart, J. F. *Chem. Soc. Rev.* 2009, 38, 1802-1820. (d) Feringa, B. L.; Browne, W. R., Eds. *Molecular Switches;* Wiley-VCH: Weinheim, 2011.
(8) (a) Brash, D.; Rudolph, J.; Simon, J.; Lin, A.; Mckenna, G.; Baden, H.; Halperin, A.; Ponten, *J. Proc. Natl. Acad. Sci. U.S.A.* 1991, 88, 1012-10128. (b) Tamai, T. K.; Vardhanabhuti, V.; Foulkes, N. S.; Whitmore, D. *Curr. Biol.* 2004, 14, R104-R105. (c) Banerjee, G.; Gupta, N.; Kapoor, A.; Raman, G. *Cancer Lett.* 2005, 223, 275-284.
(9) (a) Sadovski, O.; Beharry, A. A.; Zhang, F.; Woolley, G. A. *Angew. Chem. Int. Ed.* 2009, 48, 1484-1486. (b) Wegner, H. A. *Angew. Chem. Int. Ed.* 2012, 51, 4787-4788.
(10) (a) Beharry, A. A.; Sadovski, O.; Woolley, G. A. *J. Am. Chem. Soc.* 2011, 133, 19684-19687. (b) Bleger, D.; Schwarz, J.; Brouwer, A.; Hecht, S. *J. Am. Chem. Soc.* 2012, 134, 20597-20600. (c) Samanta, S.; Beharry, A. A.; Sadovski, O.; McCormick, T. M.; Babalhavaeji, A.; Tropepe, V.; Woolley, G. A. *J. Am. Chem. Soc.* 2013, 135, 9777-9784. (d) Samanta, S.; McCormick, T. M.; Schmidt, S. K.; Seferos, D. S.; Woolley, G. A. *Chem. Comm.* 2013, 49, 10314-10316.
(11) (a) Kurihara, M.; Hirooka, A.; Kume, S.; Sugimoto, M.; Nishihara, H. *J. Am. Chem. Soc.* 2002, 124, 8800-8801. (b) Venkataramani, S.; Jana, U.; Dammaschk, M.; Sönnichsen, F. D.; Tuczek, F.; Herges. R. *Science* 2011, 331, 445-448.
(12) Siewertsen, R.; Neumann, H.; Buchheim-Stehn, B.; Herges, R.; Nather, C.; Renth, F.; Temps, F. *J. Am. Chem. Soc.* 2009, 131, 15594-15595.
(13) Light at 630 nm penetrates only the first 5 mm of tissue, while light between 700-800 nm has a penetration of 1-2 cm. See ref. 2.
(14) Wang, L.; Dong, H.; Li, Y.; Xue, C.; Sun, L.-D.; Yan, C.-H.; Li, Q. *J. Am. Chem. Soc.* 2014, 136, 4480-4483.
(15) Sun, L.-D.; Wang, Y.-F.; Yan, C.-H. *Acc. Chem. Res.* 2014, 47, 1001-1009.
(16) Yang, Y.; Hughes, R. P.; Aprahamian, I. *J. Am. Chem. Soc.* 2012, 134, 15221-15224.
(17) The para- and/or ortho-substituted derivatives were synthesized following the synthetic protocol used in the making of the parent complex 1. See ref. 16.
(18) Mustroph, H. *Dyes Pigm.* 1991, 15, 129-137.
(19) The nature of the effect of oxygen on the isomerization rate is under investigation.
(20) Blevins, A. A.; Blanchard, G. J. *J. Phys. Chem. B* 2004, 108, 4962-4968.
(21) We are unable to measure the quantum yield of the process because of the competition with the fast thermal isomerization process, and instrumentation limitations.
(22) Mustroph, H. *Dyes Pigm.* 1991, 16, 223-230.
(23) (a) Ray, D.; Foy, J. T.; Hughes, R. P.; Aprahamian, I. *Nature Chem.* 2012, 4, 757-762. (b) Su, X.; Voskian, S.; Hughes, R. P.; Aprahamian, I. *Angew. Chem. Int. Ed.* 2013, 52, 10734-10739. (c) Tatum, L.; Su, X.; Aprahamian, I. *Acc. Chem. Res.* 2014, 47, 2141-2149. (d) Su, X.; Aprahamian, I. *Chem. Soc. Rev.* 2014, 43, 1963-1981.

Supporting Information
General Methods

All reagents and starting materials were purchased from commercial vendors and used without further purification. Column chromatography was performed on silica gel (Silicycle, 230-400 mesh). The melting points were measured on an Electrothermal 9100 instrument in open capillary tubes without thermometer correction. Deuterated solvents were purchased from Cambridge Isotope Laboratories and used as received. $^1$H NMR and $^{13}$C NMR spectra were recorded on a 500 MHz spectrometer, with working frequencies of 499.87 MHz for $^1$H nuclei and 125.7 MHz for $^{13}$C nuclei, respectively. $^{19}$F NMR spectra were recorded on a 300 MHz spectrometer, with working frequency of 282.2 MHz for $^{19}$F nuclei. Chemical shifts are expressed in ppm relative to tetramethylsilane, using the residual solvent peak as a reference standard. GC-MS spectra were measured on a Shimadzu Gas Chromatograph/Mass Spectrometer (GCMS-QP2010Plus). UV-Vis spectra were recorded on a Shimadzu UV-Vis spectrophotometer (UV-1800). Irradiation experiments were conducted with sufficient stirring using a Newport mercury lamp (67005-414) equipped with a Jarrell-Ash light monochromator. The 710 nm Near IR light source was built with appropriate LED light bulbs (LED710-1au AlGaAs Infrared LEDs purchased from Roithner Lasertechnik GmbH). PBS buffer is an aqueous solution prepared with 11.9 mM sodium phosphate (pH 7.3-7.4), 137 mM NaCl and 2.7 mM KCl.

Synthesis

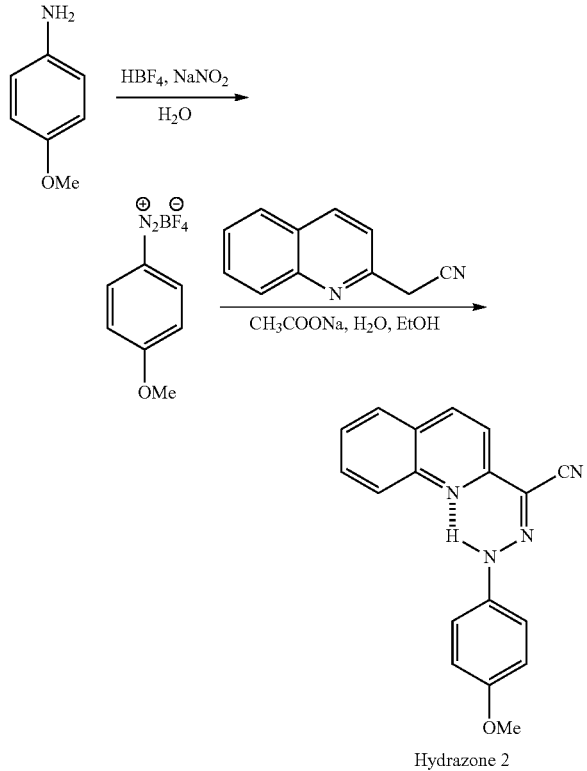

Scheme 4. Synthesis of Hydrazone 2.

Hydrazone 2: The compound was synthesized following the procedure described previously.[S1] 1.7 mL of HBF$_4$ (48%) was added dropwise to a mixture of p-anisidine (0.420 g, 3.4 mmol) in 1 mL water. After stirring in an ice-bath for 30 min, a precooled aqueous solution of NaNO$_2$ (1 equiv, 0.235 g, 3.4 mmol) was added dropwise over a period of 15 min. The pinkish diazonium salt was collected by filtration after 60 min and added to a suspension of 2-quinolylacetonitrile[S2] (0.8 equiv, 0.456 g, 2.7 mmol) and sodium acetate (3.2 equiv, 0.890 g, 10.8 mmol) in a cooled and well stirred 30 mL ethanol/water (2:1) mixture. The resulting reaction mixture was left to stir overnight at RT. The precipitated compound was then collected by filtration and dried over air. The crude product was purified by silica gel column chromatography (hexane/ethyl acetate 9:1) to give Hydrazone 2 as a dark yellow powder (0.572 g, 70%). mp 162.3-162.6° C.; $^1$H NMR (500 MHz, CDCl$_3$) δ16.18 (s, 1H), 8.29 (d, J=10.0 Hz, 1H), 8.02 (d, J=10.0 Hz, 1H), 7.80 (m, 3H), 7.61 (t, J=7.5 Hz, 1H), 7.42 (d, J=5.0 Hz, 2H), 6.97 (d, J=5.0 Hz, 2H) ppm; $^{13}$C NMR (126 MHz, CDCl$_3$) δ157.18, 152.55, 145.76, 137.79, 136.26, 130.92, 128.15, 128.07, 127.62, 126.89, 119.68, 118.43, 116.77, 115.10, 110.34, 55.86 ppm; GC-MS: calcd for C$_{18}$H$_{14}$N$_4$O, 302.1; m/z (rel. inten.) 302 (56%, M+), 195 (23%), 128 (34%), 107 (16%), 31 (12%). FIG. 24 shows a) $^1$H NMR and b) $^{13}$C NMR spectra of Hydrazone 2 (contains a small percentage of the Z isomer) in CDCl$_3$ at 294 K.

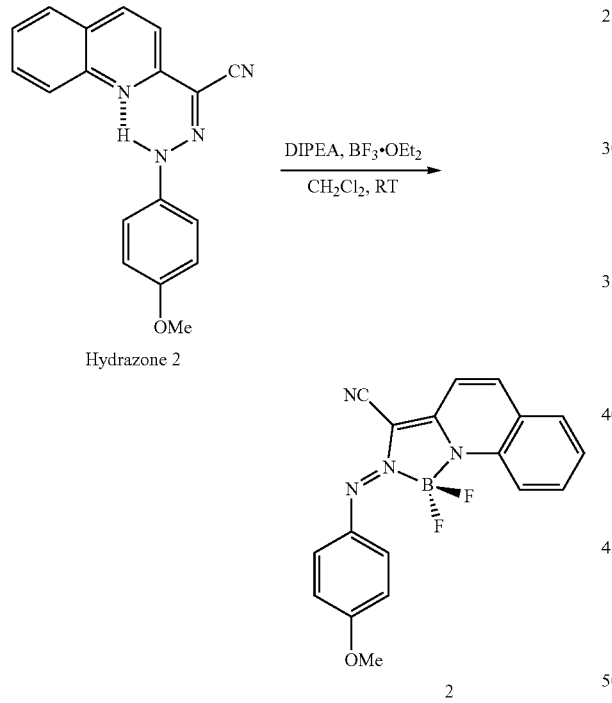

Scheme 5. Synthesis of complex 2.

Hydrazone 2

2

2: The compound was synthesized following the procedure described previously.[S1] Compound 2 was collected as a purple powder (54% yield). mp 179.8-180.4° C.; $^1$H NMR (500 MHz, CD$_2$Cl$_2$) δ8.21 (d, J=10.0 Hz, 1H), 7.81 (d, J=10.0 Hz, 2H), 7.76 (t, J=5.0 Hz, 1H), 7.72 (d, J=10.0 Hz, 2H), 7.49 (t, J=7.5 Hz, 1H), 7.34 (d, J=10.0 Hz, 1H), 7.03 (d, J=5.0 Hz, 2H), 3.91 (s, 3H) ppm; $^{13}$C NMR (126 MHz, CD$_2$Cl$_2$) δ161.30, 152.71, 144.76, 143.49, 139.17, 133.72, 129.60, 125.71, 125.04, 123.28, 118.34, 114.59, 114.20, 113.78, 112.91, 55.88 ppm; $^{19}$F NMR (282 MHz, CD$_2$Cl$_2$) δ−145.95 (q, J=19.7 Hz, 2F) ppm; GC-MS: calcd for C$_{18}$H$_{13}$BF$_2$N$_4$O, 350.1; m/z (rel. inten.) 350 (23%, M+), 144 (10%), 140 (28%), 107 (100%), 91 (22%), 51 (32%). FIG. 25 shows a) $^1$H NMR b) $^{13}$C NMR and c) $^{19}$F NMR spectra of 2-trans (contains a small percentage of the cis isomer) in CD$_2$Cl$_2$ at 294 K. FIG. 26 shows a $^1$H NMR spectrum of 2 after being stored in the dark. The equilibrated mixture of 2 was determined to have an isomer ratio of 93:7 (trans:cis). FIG. 27 shows a $^1$H NMR spectra of the PSS of 2 at a) 490 nm and b) 630 nm in CD$_2$Cl$_2$ at 294 K. The PSS isomer ratios of 92±1% trans at l$_{irr}$=490 nm, and 96±1% cis at l$_{irr}$=630 nm are the averages of three experiments.

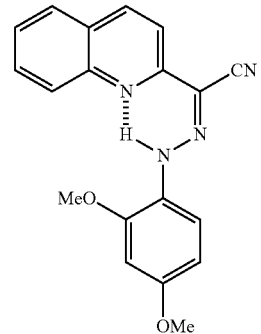

Hydrazone 3

Hydrazone 3: The compound was synthesized following the procedure used for Hydrazone 2. Hydrazone 3 was collected as a dark yellow powder (68% yield). mp 164.2-164.7° C.; $^1$H NMR (500 MHz, CDCl$_3$) δ16.08 (s, 1H), 8.18 (d, J=10.0 Hz, 1H), 7.96 (d, J=5.0 Hz, 1H), 7.75 (m, 3H), 7.65 (d, J=10.0 Hz, 1H), 7.55 (t, J=5.0 Hz, 1H), 6.55 (m, 2H) 4.06 (s, 3H), 3.83 (s, 3H) ppm; $^{13}$C NMR (126 MHz, CDCl$_3$) δ157.66, 152.16, 148.93, 145.86, 137.29, 130.68, 128.18, 127.90, 127.34, 126.71, 126.08, 119.39, 118.78, 115.24, 110.68, 105.46, 99.17, 56.31, 55.88 ppm; GC-MS: calcd for C$_{19}$H$_{16}$N$_4$O$_2$ 332.1; m/z (rel. inten.) 332 (66%, M+), 137 (21%), 128 (15%), 77 (100%), 51 (13%). FIG. 28 shows a) $^1$H NMR and b) $^{13}$C NMR spectra of Hydrazone 3 (contains a small percentage of the Z isomer) in CDCl$_3$ at 294 K.

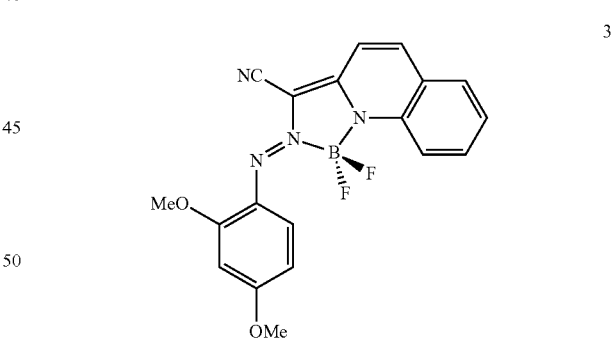

3

Figure 29:
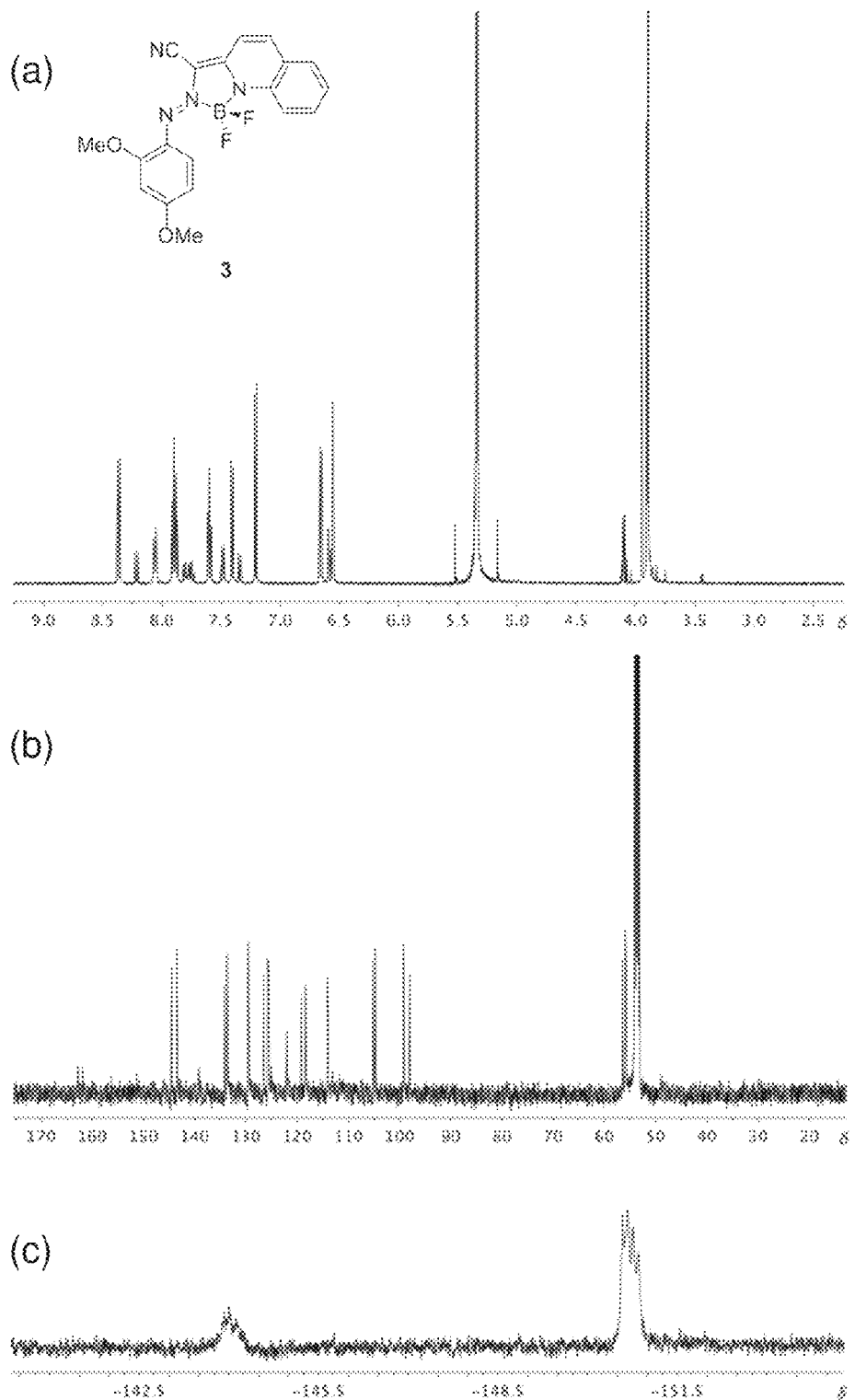
FIG. 29. a) $^1H$ NMR b) $^{13}C$ NMR and c) $^{19}F$ NMR spectra of 3-cis (contains a small percentage of the trans isomer) in $CD_2Cl_2$ at 294 K.

3: The compound was synthesized following the procedure described previously.[S1] Compound 3 was collected as a purple powder (48% yield). mp 169.3-169.8° C.; $^1$H NMR (500 MHz, CD$_2$Cl$_2$) δ8.36 (d, J=10.0 Hz, 1H), 8.06 (d, J=10.0 Hz, 1H), 7.88 (m, 2H), 7.60 (t, J=7.5 Hz, 1H), 7.41 (d, J=10.0 Hz, 1H), 7.21 (d, J=10.0 Hz, 1H), 6.66 (d, J=10.0 Hz, 1H), 6.56 (dd, J=5.0 Hz, 1H), 3.95 (s, 3H), 3.90 (s, 3H) ppm; $^{13}$C NMR (126 MHz, CD$_2$Cl$_2$) δ162.75, 161.85, 144.56, 143.48, 134.16, 133.67, 129.53, 125.73, 121.97, 119.26, 118.38, 114.17, 114.08, 105.14, 104.72, 99.24, 98.03, 56.46, 55.87 ppm; $^{19}$F NMR (282 MHz, CD$_2$Cl$_2$) δ−150.71 (q, J=25.4 Hz, 2F) ppm; GC-MS: calcd for C$_{19}$H$_{15}$BF$_2$N$_4$O$_2$, 380.1; m/z (rel. inten.) 380 (24%, M+), 207 (70%), 137 (26%), 128 (30%), 73 (100%). FIG. 29 shows a) $^1$H NMR b) $^{13}$C NMR and c) $^{19}$F NMR spectra of 3-cis (contains a small percentage of the trans isomer) in CD$_2$Cl$_2$ at 294 K. FIG. 30 shows a $^1$H NMR spectrum of 3 after being stored in the dark. The equilibrated mixture of 3 was determined to have an isomer ratio of 58:42 (trans:cis). FIG. 31 shows a $^1$H NMR spectra of the PSS of 3 at a) 490 nm and b) 640 nm in CD$_2$Cl$_2$ at 294 K. The PSS isomer ratios of 56±1% trans at $l_{irr}$=490 nm, and 79±1% cis at $l_{irr}$=640 nm are the averages of three experiments.

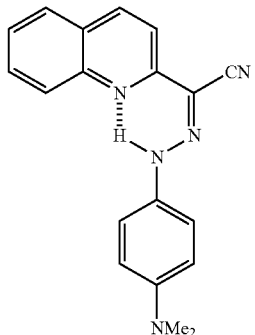

Hydrazone 4

Figure 32:
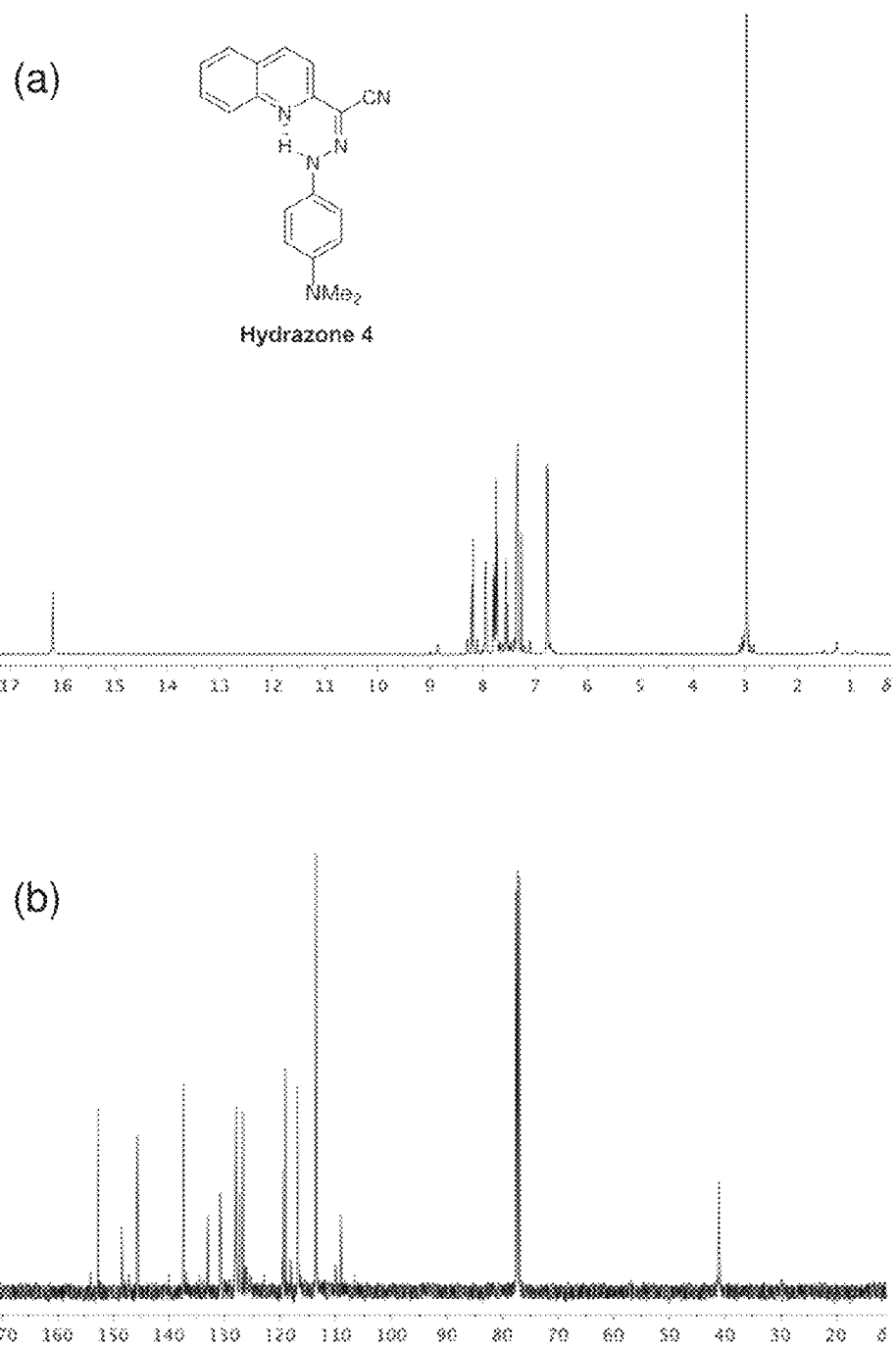
FIG. 32. a) $^1H$ NMR and b) $^{13}C$ NMR spectra of Hydrazone 4 (contains a small percentage of the Z isomer) in $CDCl_3$ at 294 K.

Hydrazone 4: The compound was synthesized following the procedure used for Hydrazone 2. Hydrazone 4 was collected as a brown powder (64% yield). mp 170.3-170.7° C.; $^1$H NMR (500 MHz, CDCl$_3$) δ16.18 (s, 1H), 8.19 (d, J=10.0 Hz, 1H), 7.94 (d, J=10.0 Hz, 1H), 7.75 (m, 3H), 7.55 (t, J=10.0 Hz, 1H), 7.34 (d, J=10.0 Hz, 2H), 6.76 (d, J=5.0 Hz, 2H), 2.98 (s, 3H) ppm; $^{13}$C NMR (126 MHz, CDCl$_3$) δ152.73, 148.49, 145.71, 137.41, 137.38, 132.99, 130.70, 127.93, 127.18, 126.65, 119.47, 118.94, 116.83, 113.52, 109.04, 41.09 ppm; GC-MS: calcd for C$_{19}$H$_{17}$N$_5$, 315.2; m/z (rel. inten.) 315 (60%, M$^+$), 301 (14%), 134 (100%), 119 (46%), 93 (27%), 65 (17%). FIG. 32 shows a) $^1$H NMR and b) $^{13}$C NMR spectra of Hydrazone 4 (contains a small percentage of the Z isomer) in CDCl$_3$ at 294 K.

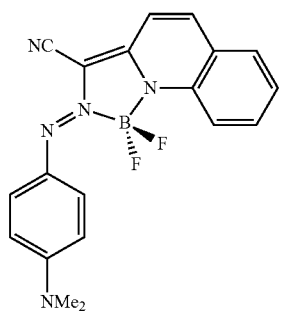

4

Figure 34:
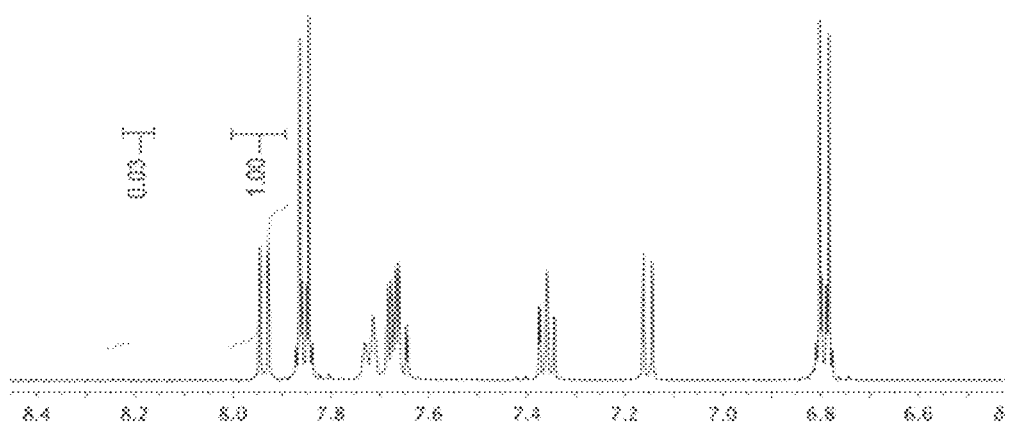
FIG. 34. $^1H$ NMR spectrum of 4 after being stored in the dark. The equilibrated mixture of 4 was determined to have an isomer ratio of 97:3 (trans:cis).
Figure 35:
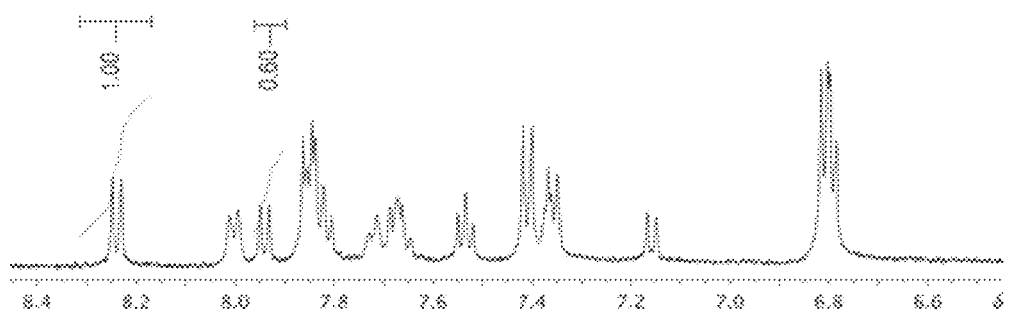
FIG. 35. $^1H$ NMR spectrum recording the lowest estimation of PSS of 4 at 710 nm in $CD_2Cl_2$ at 294 K. The PSS isomer ratio of 63±1% cis at $\lambda_{irr}$=710 nm is the average of three experiments.

4: The compound was synthesized following the procedure described previously.$^{S1}$ Compound 4 was collected as a green powder (65% yield). mp 193.4-193.8° C.; $^1$H NMR (500 MHz, CD$_2$Cl$_2$) δ7.94 (d, J=10.0 Hz, 1H), 7.86 (d, J=10.0 Hz, 2H), 7.72 (d, J=10.0 Hz, 1H), 7.66 (m, 2H), 7.36 (t, J=10.0 Hz, 1H), 7.15 (d, J=10.0 Hz, 1H), 6.80 (d, J=10.0 Hz, 2H), 3.17 (s, 6H) ppm; $^{13}$C NMR (126 MHz, CD$_2$Cl$_2$) δ152.49, 141.25, 139.42, 132.86, 129.29, 128.25, 128.20, 128.15, 124.48, 124.36, 117.66, 117.64, 114.48, 114.01, 112.11, 40.30 ppm; $^{19}$F NMR (282 MHz, CD$_2$Cl$_2$) δ−150.45 (q, J=32.0 Hz, 2F) ppm; GC-MS: calcd for C$_{19}$H$_{16}$BF$_2$N$_5$, 363.1; m/z (rel. inten.) 363 (20%, M$^+$), 281 (4%), 207 (11%), 134 (100%), 120 (49%), 65 (17%). FIG. 33 shows a) $^1$H NMR b) $^{13}$C NMR and c) $^{19}$F NMR spectra of 4-trans in CD$_2$Cl$_2$ at 294 K. FIG. 34 shows a $^1$H NMR spectrum of 4 after being stored in the dark. The equilibrated mixture of 4 was determined to have an isomer ratio of 97:3 (trans:cis). FIG. 35 shows a $^1$H NMR spectrum recording the lowest estimation of PSS of 4 at 710 nm in CD$_2$Cl$_2$ at 294 K. The PSS isomer ratio of 63±1% cis at $l_{irr}$=710 nm is the average of three experiments.

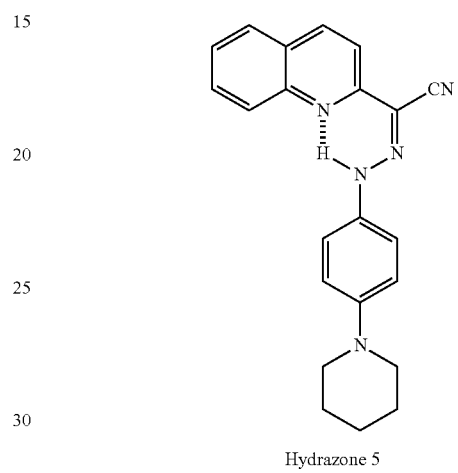

Hydrazone 5

Hydrazone 5: The compound was synthesized following the procedure used for Hydrazone 2. Hydrazone 5 was collected as a brown powder (51% yield). mp 168.5-168.9° C.; $^1$H NMR (500 MHz, CDCl$_3$) δ16.16 (s, 1H), 8.23 (d, J=10.0 Hz, 1H), 7.98 (d, J=10.0 Hz, 1H), 7.78 (m, 3H), 7.58 (t, J=7.5 Hz, 1H), 7.36 (d, J=5.0 Hz, 2H), 6.99 (d, J=10.0 Hz, 2H), 3.17 (t, J=5.0 Hz, 4H), 1.74 (m, 4H), 1.61 (m, 2H) ppm; $^{13}$C NMR (126 MHz, CDCl$_3$) δ152.64, 149.95, 145.75, 137.56, 134.91, 130.80, 128.06, 128.00, 127.41, 126.76, 119.59, 118.69, 117.63, 116.52, 109.69, 51.15, 24.45, 22.93 ppm; GC-MS: calcd for C$_{22}$H$_{21}$N$_5$, 355.2; m/z (rel. inten.) 355 (51%, M$^+$), 160 (20%), 140 (28%), 84 (17%), 77 (100%), 51 (16%). FIG. 36 shows a) $^1$H NMR and b) $^{13}$C NMR spectra of Hydrazone 5 (contains a small percentage of the Z isomer) in CDCl$_3$ at 294 K.

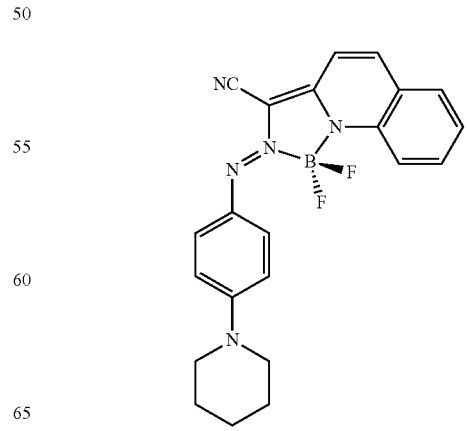

5

Figure 38:
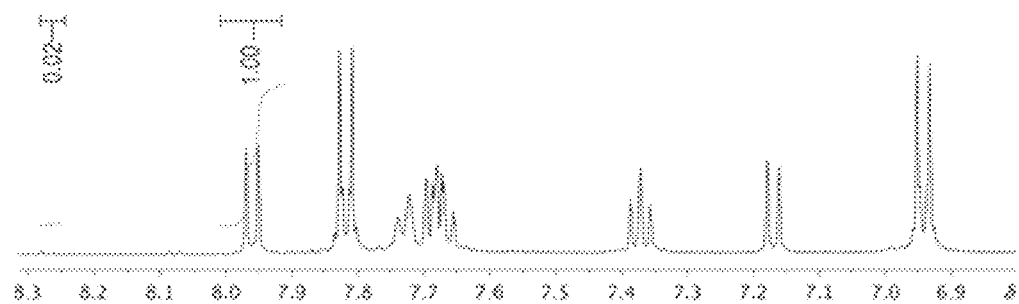
FIG. 38. $^1H$ NMR spectrum of 5 after being stored in the dark. The equilibrated mixture of 5 was determined to have an isomer ratio of 98:2 (trans:cis).
Figure 39:
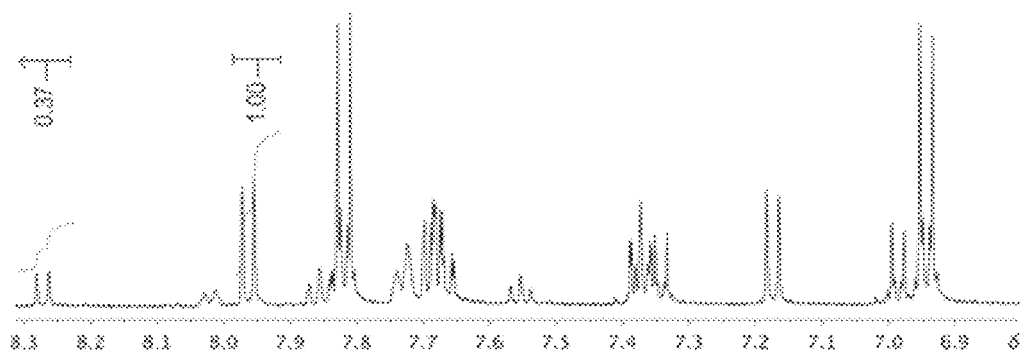
FIG. 39. $^1H$ NMR spectrum recording the lowest estimation of PSS of 5 at 710 nm in $CD_2Cl_2$ at 294 K. The PSS isomer ratio of 28±1% cis at $\lambda_{irr}$=710 nm is the average of three experiments.

5: The compound was synthesized following the procedure described previously.[S1] Compound 5 was collected as a green powder (56% yield). mp 187.5-188.0° C.; $^1$H NMR (500 MHz, CD$_2$Cl$_2$) δ7.96 (d, J=10.0 Hz, 1H), 7.82 (d, J=7.5 Hz, 2H), 7.73 (d, J=10.0 Hz, 1H), 7.67 (m, 2H), 7.37 (t, J=10.0 Hz, 1H), 7.17 (d, J=10.0 Hz, 1H), 6.95 (d, J=10.0 Hz, 2H), 3.51 (t, J=5.0 Hz, 4H), 1.72 (s, 6H) ppm; $^{13}$C NMR (126 MHz, CD$_2$Cl$_2$) δ152.69, 141.44, 138.81, 132.94, 129.32, 128.12, 128.04, 124.60, 124.43. 117.72, 117.31, 116.41, 114.47, 113.93, 113.74, 48.59, 25.78, 24.54 ppm; $^{19}$F NMR (282 MHz, CD$_2$Cl$_2$) δ−150.11 (q, J=18.8 Hz, 2F) ppm; GC-MS: calcd for C$_{22}$H$_{20}$BF$_2$N$_5$, 403.2; m/z (rel. inten.) 403 (14%, M$^+$), 355 (10%), 281 (35%), 253 (12%), 207 (87%), 135 (31%), 73 (100%). FIG. 37 shows a) $^1$H NMR b) $^{13}$C NMR and c) $^{19}$F NMR spectra of 5-trans (contains a small percentage of the cis isomer) in CD$_2$Cl$_2$ at 294 K. FIG. 38 shows a $^1$H NMR spectrum of 5 after being stored in the dark. The equilibrated mixture of 5 was determined to have an isomer ratio of 98:2 (trans:cis). FIG. 39 shows a $^1$H NMR spectrum recording the lowest estimation of PSS of 5 at 710 nm in CD$_2$Cl$_2$ at 294 K. The PSS isomer ratio of 28±1% cis at l$_{irr}$=710 nm is the average of three experiments.

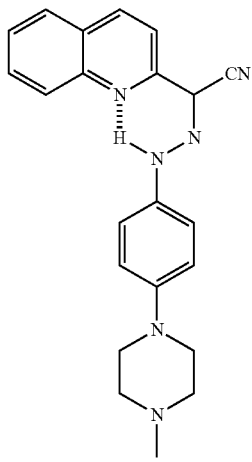

Hydrazone 6

Figure 44:
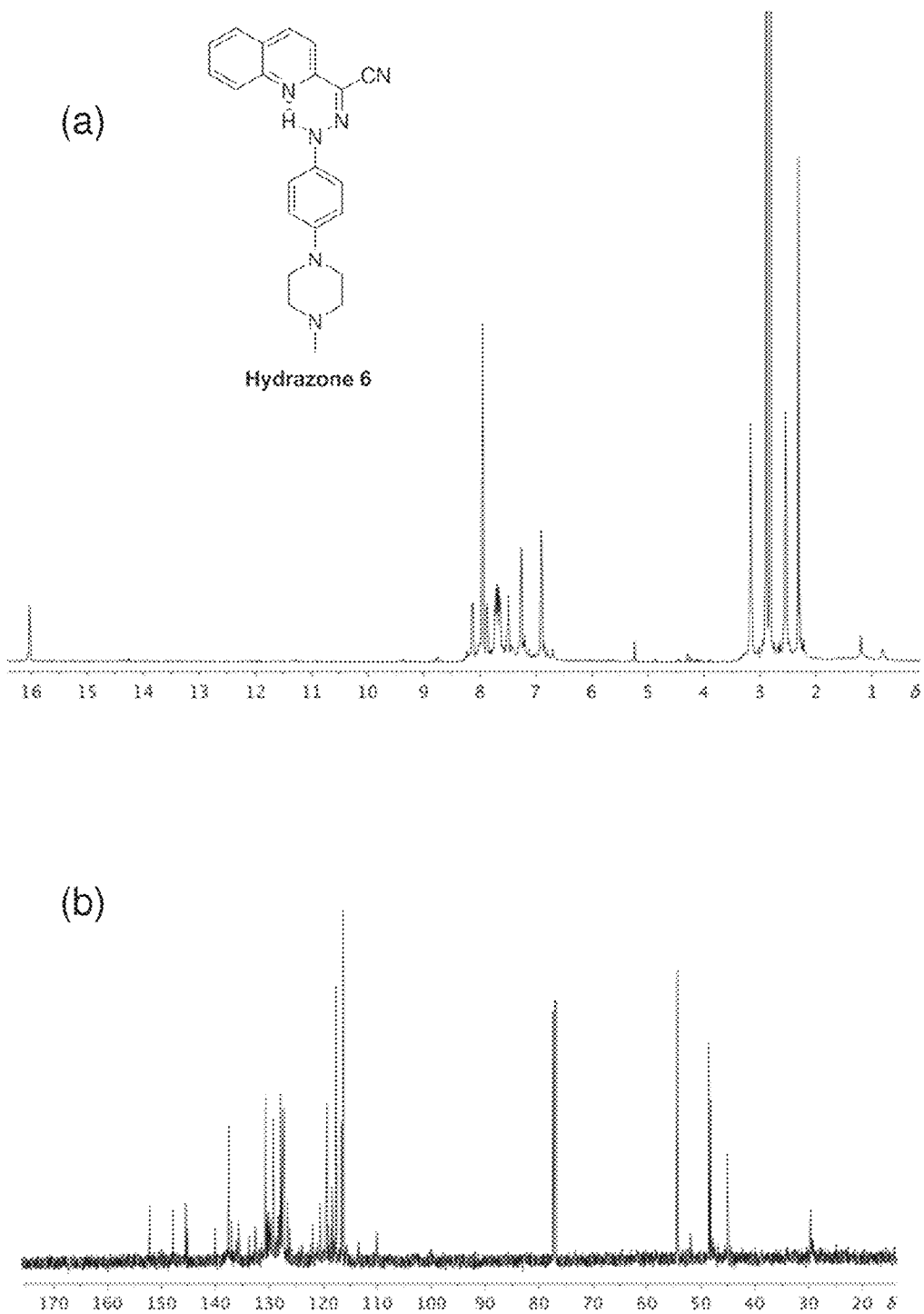
FIG. 44. a) $^1H$ NMR and b) $^{13}C$ NMR spectra of Hydrazone 6 (contains a small percentage of the Z isomer) in $CDCl_3$ at 294 K.

Hydrazone 6: The compound was synthesized following the procedure used for Hydrazone 2. Hydrazone 6 was collected as a brown powder (55% yield). mp 163.5-164.0° C.; $^1$H NMR (500 MHz, CDCl$_3$) δ16.03 (s, 1H), 8.13 (d, J=10.0 Hz, 1H), 7.87 (d, J=10.0 Hz, 1H), 7.66 (m, 3H), 7.49 (t, J=5.0 Hz, 1H), 7.26 (d, J=10.0 Hz, 2H), 6.90 (d, J=5.0 Hz, 2H), 3.17 (t, J=5.0 Hz, 4H), 2.55 (t, J=5.0 Hz, 4H), 2.32 (s, 3H) ppm; $^{13}$C NMR (126 MHz, CDCl$_3$) δ152.21, 147.86, 145.45, 140.06, 137.49, 136.94, 135.74, 130.71, 129.75, 127.64, 127.38, 119.34, 117.60, 116.57, 116.32, 54.39, 48.51, 45.08 ppm; GC-MS: calcd for C$_{22}$H$_{22}$N$_6$, 370.2; m/z (rel. inten.) 370 (63%, M$^+$), 175 (22%), 140 (36%), 105 (14%), 77 (100%). FIG. 44 shows a) $^1$H NMR and b) $^{13}$C NMR spectra of Hydrazone 6 (contains a small percentage of the Z isomer) in CDCl$_3$ at 294 K.

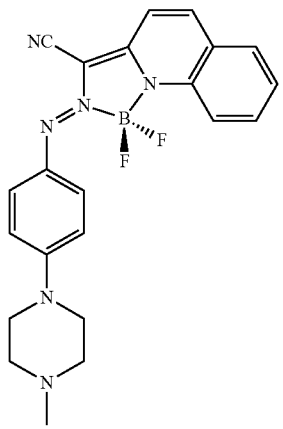

6

Figure 45:
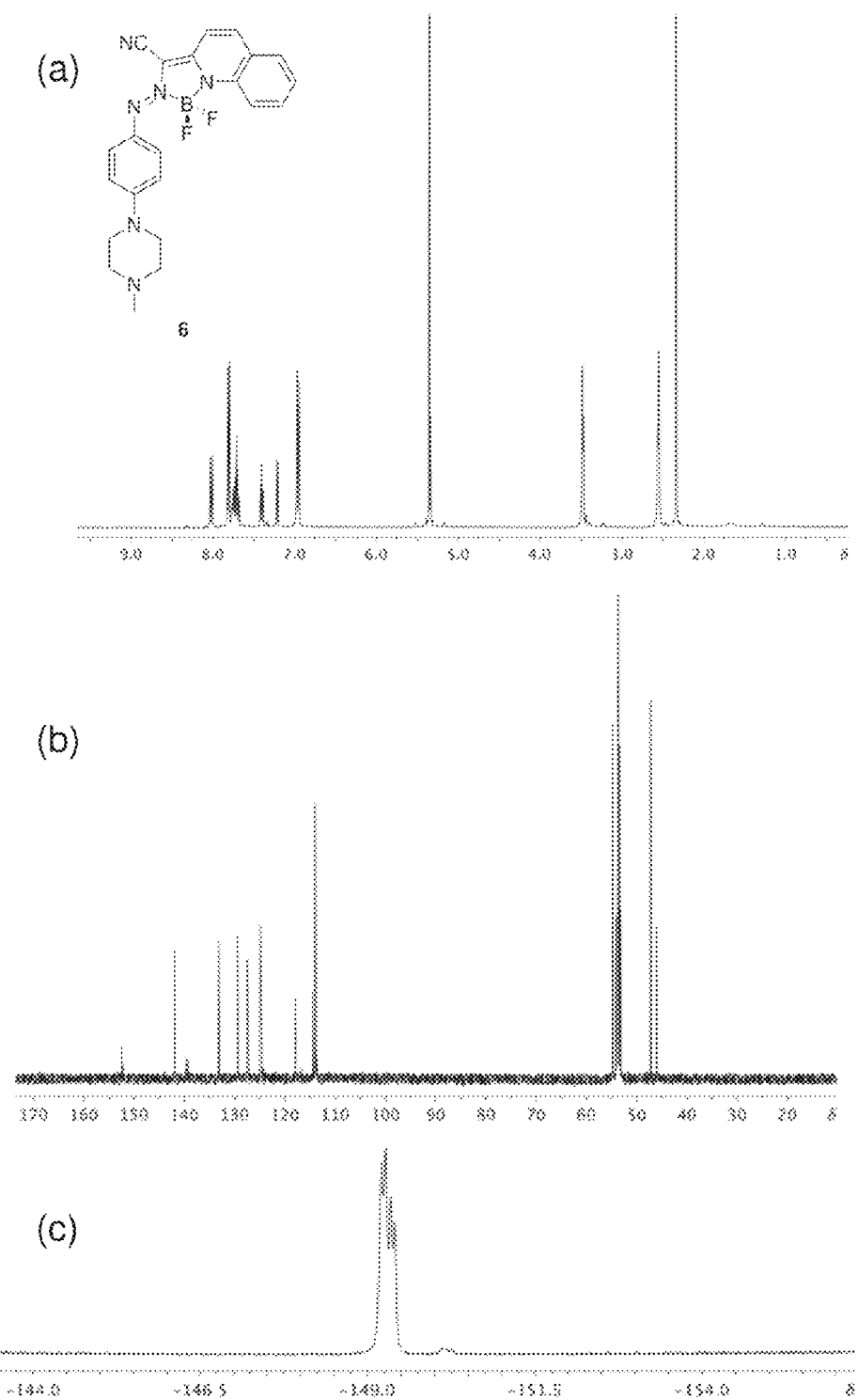
FIG. 45. a) $^1H$ NMR b) $^{13}C$ NMR and c) $^{19}F$ NMR spectra of 6-trans (contains a small percentage of the cis isomer) in $CD_2Cl_2$ at 294 K.
Figure 46:
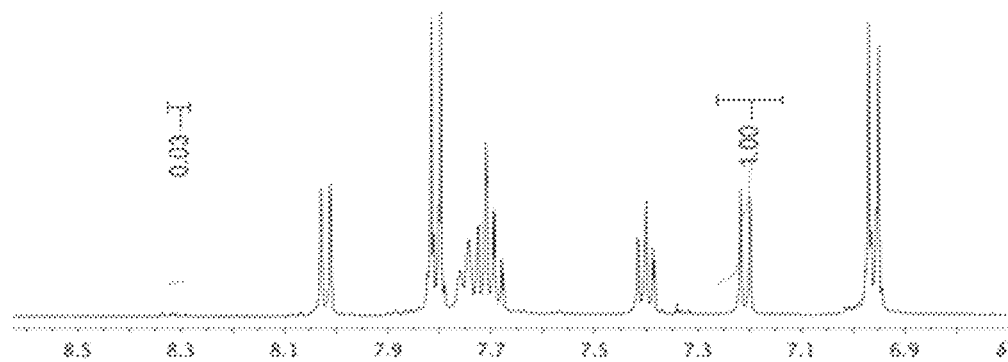
FIG. 46. $^1H$ NMR spectrum of 6 after being stored in the dark. The equilibrated mixture of 7 was determined to have an isomer ratio of 97:3 (trans:cis).
Figure 47:
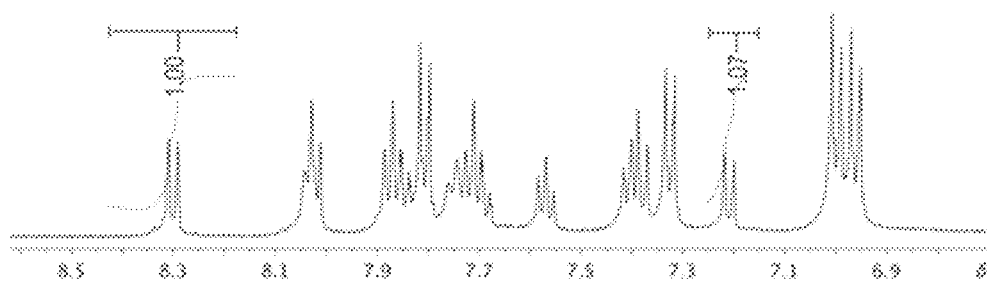
FIG. 47. $^1H$ NMR spectrum recording the lowest estimation of PSS of 6 at 710 nm in $CD_2Cl_2$ at 294 K. The PSS isomer ratio of 49±1% cis at $\lambda_{irr}$=710 nm is the average of three experiments.

6: The compound was synthesized following the procedure described previously.[S1] Compound 6 was collected as a green powder (42% yield). mp 181.7-182.1° C.; $^1$H NMR (500 MHz, CD$_2$Cl$_2$) δ8.02 (d, J=10.0 Hz, 1H), 7.81 (d, J=5.0 Hz, 2H), 7.70 (m, 3H), 7.40 (t, J=10.0 Hz, 1H), 7.21 (d, J=10.0 Hz, 1H), 6.97 (d, J=7.5 Hz, 2H), 3.48 (t, J=5.0 Hz, 4H), 2.55 (t, J=5.0 Hz, 4H), 2.33 (s, 3H) ppm; $^{13}$C NMR (126 MHz, CD$_2$Cl$_2$) δ152.46, 152.23, 141.96, 139.70, 139.35, 133.13, 129.39, 127.49, 127.39, 124.89, 124.58, 117.87, 114.40, 113.97, 113.70, 54.85, 47.22, 46.04 ppm; $^{19}$F NMR (282 MHz, CD$_2$Cl$_2$) δ−149.31 (q, J=18.8 Hz, 2F) ppm; GC-MS: calcd for C$_{22}$H$_{21}$BF$_2$N$_6$, 418.2; m/z (rel. inten.) 418 (20%, M$^+$), 355 (12%), 281 (30%), 253 (13%), 207 (84%), 77 (100%). FIG. 45 shows a) $^1$H NMR b) $^{13}$C NMR and c) $^{19}$F NMR spectra of 6-trans (contains a small percentage of the cis isomer) in CD$_2$Cl$_2$ at 294 K. FIG. 46 shows a $^1$H NMR spectrum of 6 after being stored in the dark. The equilibrated mixture of 7 was determined to have an isomer ratio of 97:3 (trans:cis). FIG. 47 shows a $^1$H NMR spectrum recording the lowest estimation of PSS of 6 at 710 nm in CD$_2$Cl$_2$ at 294 K. The PSS isomer ratio of 49±1% cis at l$_{irr}$=710 nm is the average of three experiments.

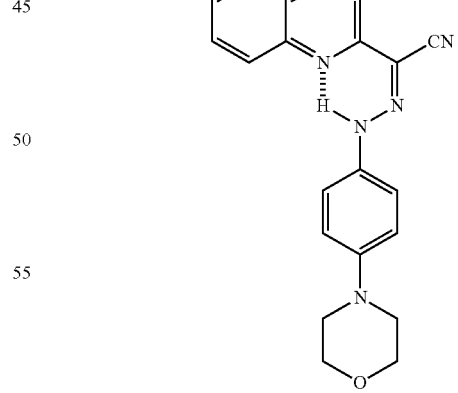

Hydrazone 7

Hydrazone 7: The compound was synthesized following the procedure used for Hydrazone 2. Hydrazone 7 was collected as a brown oil (56% yield). $^1$H NMR (500 MHz, CDCl$_3$) δ16.08 (s, 1H), 8.20 (d, J=10.0 Hz, 1H), 7.94 (d, J=10.0 Hz, 1H), 7.75 (m, 3H), 7.56 (t, J=7.5 Hz, 1H), 7.34

(d, J=10.0 Hz, 2H), 6.95 (d, J=10.0 Hz, 2H), 3.88 (t, J=5.0 Hz, 4H), 3.17 (t, J=5.0 Hz, 4H) ppm; $^{13}$C NMR (126 MHz, CDCl$_3$) δ152.47, 148.83, 145.67, 137.60, 135.63, 130.86, 128.06, 128.00, 127.52, 126.76, 119.54, 118.52, 116.91, 116.54, 110.04, 69.09, 49.84 ppm; GC-MS: calcd for C$_{21}$H$_{19}$N$_4$O, 357.2; m/z (rel. inten.) 357 (64%, M$^+$), 162 (18%), 140 (31%), 105 (18%), 77 (100%). FIG. 40 shows a) $^1$H NMR and b) $^{13}$C NMR spectra of Hydrazone 7 (contains a small percentage of the Z isomer) in CDCl$_3$ at 294 K.

recording the lowest estimation of PSS of 7 at 710 nm in CD$_2$Cl$_2$ at 294 K. The PSS isomer ratio of 82±1% cis at l$_{irr}$=710 nm is the average of three experiments.

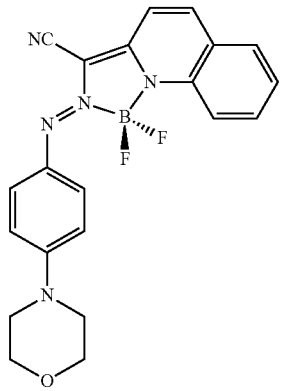

7

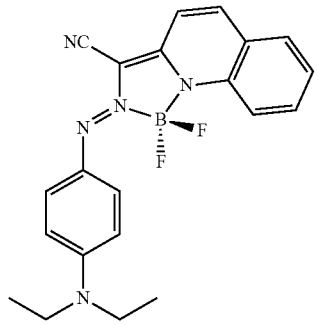

8

8: The compound was synthesized following the procedure described previously.[S1] $^1$H NMR (500 MHz CD$_2$Cl$_2$) δ: 7.81, 7.76, 7.62, 7.55, 7.47, 7.24, 7.03, 6.68, 4.33, 3.56, 1.75, 1.47

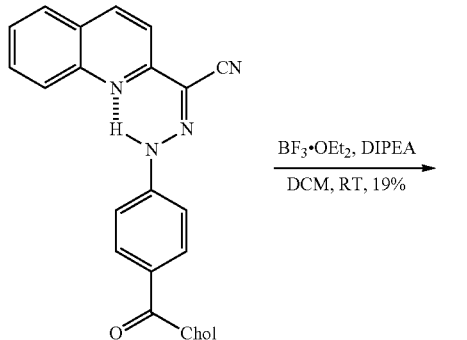

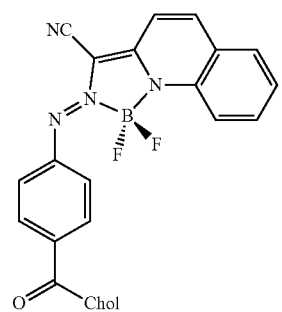

9

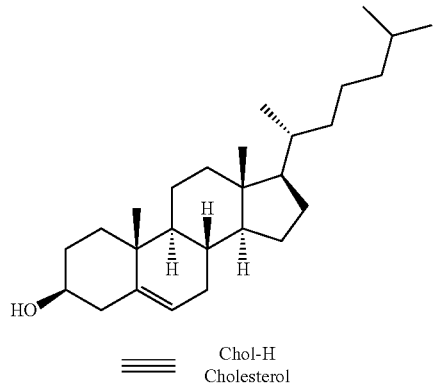

Chol-H
Cholesterol

Figure 41:
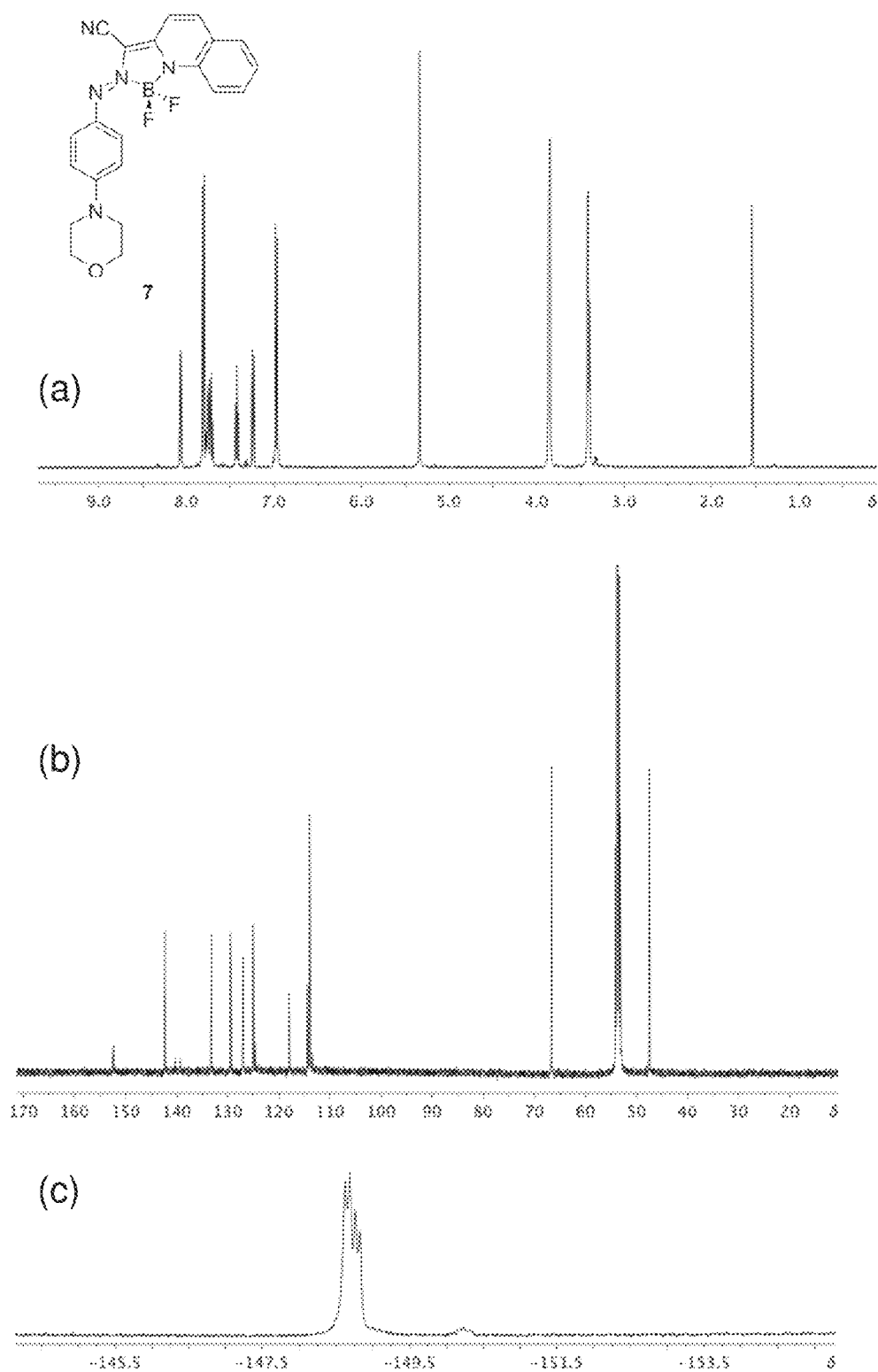
FIG. 41. a) $^1H$ NMR b) $^{13}C$ NMR and c) $^{19}F$ NMR spectra of 7-trans (contains a small percentage of the cis isomer) in $CD_2Cl_2$ at 294 K.
Figure 42:
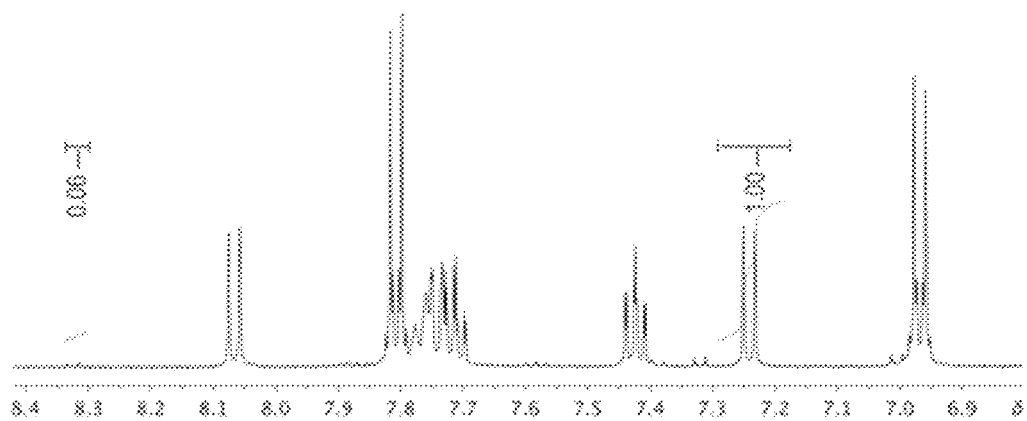
FIG. 42. $^1H$ NMR spectrum of 7 after being stored in the dark. The equilibrated mixture of 7 was determined to have an isomer ratio of 94:6 (trans:cis).
Figure 43:
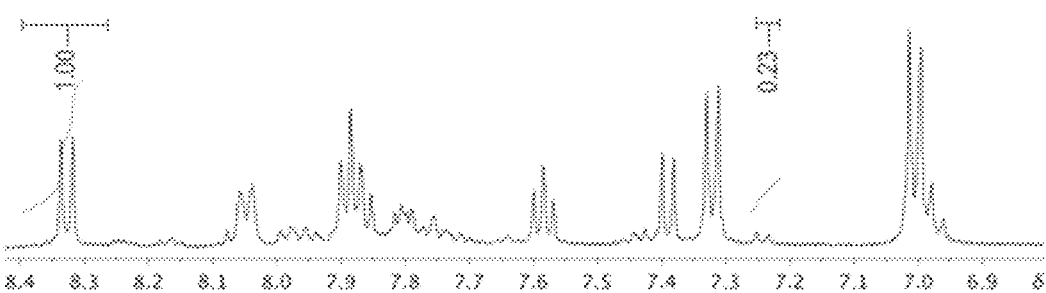
FIG. 43. $^1H$ NMR spectrum recording the lowest estimation of PSS of 7 at 710 nm in $CD_2Cl_2$ at 294 K. The PSS isomer ratio of 82±1% cis at $\lambda_{irr}$=710 nm is the average of three experiments.

7: The compound was synthesized following the procedure described previously.[S1] Compound 7 was collected as a green powder (45% yield). mp 174.8-175.3° C.; $^1$H NMR (500 MHz, CD$_2$Cl$_2$) δ8.06 (d, J=5.0 Hz, 1H), 7.81 (d, J=7.5 Hz, 2H), 7.73 (m, 3H), 7.42 (t, J=7.5 Hz, 1H), 7.24 (d, J=10.0 Hz, 1H), 6.97 (d, J=10.0 Hz, 2H), 3.86 (t, J=5.0 Hz, 4H), 3.41 (t, J=5.0 Hz, 4H) ppm; $^{13}$C NMR (126 MHz, CD$_2$Cl$_2$) δ152.44, 142.31, 140.35, 139.30, 133.32, 129.52, 129.39, 127.09, 126.92. 125.09, 124.69, 117.97, 114.36, 114.07, 113.52, 66.65, 47.51 ppm; $^{19}$F NMR (282 MHz, CD$_2$Cl$_2$) δ−148.73 (q, J=18.8 Hz, 2F) ppm; GC-MS: calcd for C$_{21}$H$_{18}$BF$_2$N$_5$O, 405.2; m/z (rel. inten.) 405 (26%, M$^+$), 355 (10%), 281 (32%), 253 (11%), 207 (83%), 135 (37%), 73 (100%). FIG. 41 shows a) $^1$H NMR b) $^{13}$C NMR and c) $^{19}$F NMR spectra of 7-trans (contains a small percentage of the cis isomer) in CD$_2$Cl$_2$ at 294 K. FIG. 42 shows a $^1$H NMR spectrum of 7 after being stored in the dark. The equilibrated mixture of 7 was determined to have an isomer ratio of 94:6 (trans:cis). FIG. 43 shows a $^1$H NMR spectrum 9: Compound 9 includes a ester linked cholesterol substituent in the para position. The compound starts to decompose at 195.5° C. before reaching its mp; $^1$H NMR (500 MHz, CD$_2$Cl$_2$) δ=8.41 (d, J=8.9 Hz, 1H), 8.13 (dd, J=6.8, 1.9 Hz, 2H), 7.91 (d, J=7.9 Hz, 1H), 7.84 (m, 2H), 7.59 (t, J=8 Hz, 1H), 7.53 (d, J=8.6 Hz, 2H), 7.49 (d, J=8.9 Hz, 1H), 5.37 (s, 1H), 4.86 (m, 1H), 2.50 (m, 1h), and 2.11-0.062 (cholesterol skeleton). $^{13}$C NMR (126 MHz, CD$_2$Cl$_2$) δ=165.22, 152.68, 144.96, 140.02, 139.11, 134.41, 131.12, 130.25, 130.22, 129.77, 128.95, 126.77, 125.73, 122.88, 122.40, 118.87, 114.22, 75.00, 71.89, 65.69, 56.97, 56.39, 54.08, 53.86, 53.65, 53.43, 53.21, 50.35, 42.52, 40.01, 39.71, 38.40, 37.26, 36.87, 36.40, 36.04, 32.17, 32.11, 30.78, 28.42, 28.24, 28.07, 27.96, 24.47, 24.02, 22.77, 22.52, 21.27, 19.40, 19.37, 19.10, 18.72, 13.71, 11.84 ppm; $^{19}$F NMR (282 MHz, CD$_2$Cl$_2$) δ=−150.66 (m, 2F); GC-MS: calcd. for C$_{45}$H$_{55}$BF$_2$N$_4$O$_2$ 732.33; m/z (rel. inten.) 732.2 (7.5%, M$^+$).

Kinetics Studies

A 0.1 mM deoxygenated $CH_2Cl_2$ solution of compound 2 in a quartz cuvette was irradiated at 630 nm until its photostationary state was reached (no further changes in the UV-Vis spectra were observed). The thermal isomerization process was monitored by measuring the change in absorption intensity at 594 nm as a function of time (at 1 min intervals). The half-life ($t_{1/2}$) of the cis→trans isomerization for 2 was calculated to be 10.4 h, which is the average of three measurements conducted under the same conditions. When the rate was measured in an unaltered solution, the half-life of 2 went down to 25 min. The half-life of 3 was measured as well in deoxygenated $CH_2Cl_2$, and was determined to be 13.4 h.

Unaltered $CD_2Cl_2$ solution of compound 4 in a quartz NMR tube was irradiated at 710 nm until its photostationary state was reached. The thermal isomerization process was monitored by measuring the change in the integrations of diagnostic peaks of both cis and trans isomers as a function of time (at 30 seconds intervals). The half-life ($t_{1/2}$) of the cis→trans isomerization was calculated to be 250 s, which is the average of three measurements conducted under the same conditions. No obvious change was observed in deoxygenated samples of 4. Similar kinetics experiments were carried out for compounds 5-7, and their half-lives are summarized in Table B.

TABLE B

The cis→trans thermal relaxation rates for 4-7 in $CD_2Cl_2$ at 294 K.

| Compound | 4 | 5 | 6 | 7 |
|---|---|---|---|---|
| Half-life | 250 s | 150 s | 400 s | 900 s |

X-Ray Crystallography

Data were collected using a Bruker CCD (charge coupled device) based diffractometer equipped with an Oxford Cryostream low-temperature apparatus operating at 173 K. Data were measured using omega and phi scans of 1° per frame for 30 s. The total number of images was based on results from the program COSMO[S3] where redundancy was expected to be 4.0 and completeness to 0.83 Å to 100%. Cell parameters were retrieved using APEX II software[S4] and refined using SAINT on all observed reflections. Data reduction was performed using the SAINT software[S5] which corrects for Lp. Scaling and absorption corrections were applied using SADABS[S6] multi-scan technique, supplied by George Sheldrick. The structures are solved by the direct method using the SHELXS-97 and refined by least squares method on $F^2$, SHELXL-97, which are incorporated in SHELXTL-PC V 6.10.[S7] The structure of 2 and 4 were solved in the space group $P2_1/c$. All non-hydrogen atoms are refined anisotropically. Hydrogens were calculated by geometrical methods and refined as a riding model. Crystals used for the diffraction studies showed no decomposition during data collection.

Preparation of the Crystal Sample of 2:

Compound 2 (20 mg) was dissolved in 3 mL methylene chloride. The solution was stored in the dark and allowed to evaporate over 2 days. Dark yellow plate crystals were collected.

Preparation of the Crystal Sample of 4:

Compound 4 (20 mg) was dissolved in 3 mL methylene chloride. The solution was stored in the dark and allowed to evaporate over 2 days. Red block crystals were collected.

TABLE C

Crystal Data and Parameters for 2 and 4.

| | 2 | 4 |
|---|---|---|
| Empirical formula | $C_{18}H_{13}BF_2N_4O$ | $C_{19}H_{16}BF_2N_5$ |
| Formula weight | 350.13 | 363.18 |
| Temperature | 172.99 K | 173.15 K |
| Wavelength | 1.54178 Å | 0.71073 Å |
| Crystal system | Monoclinic | Monoclinic |
| Space group | $P\,2_1/c$ | $P\,2_1/c$ |
| Unit cell dimensions | a = 16.9594(2) Å | a = 17.6056(13) Å |
| | α = 90° | α = 90° |
| | b = 12.7408(2) Å | b = 13.5354(10) Å |
| | β = 94.1250(1)° | β = 100.3040(10)° |
| | c = 7.2440(1) Å | c = 7.3372(5) Å |
| | γ = 90°. | γ = 90°. |
| Volume | 1561.20(4) Å$^3$ | 1720.2(2) Å$^3$ |
| Z | 4 | 4 |
| Density (calculated) | 1.490 Mg/m$^3$ | 1.402 Mg/m$^3$ |
| Absorption coefficient | 0.938 mm$^{-1}$ | 0.101 mm$^{-1}$ |
| F(000) | 720 | 752 |
| Crystal size | 0.279 × 0.171 × 0.05 mm$^3$ | 0.391 × 0.198 × 0.132 mm$^3$ |
| Theta range for data collection | 8.688 to 136.638° | 3.82 to 50.74° |
| Index ranges | −20 <= h <= 19, −15 <= k <= 15, −8 <= l <= 8 | −21 <= h <= 21, −16 <= k <= 16, −8 <= l <=8 |
| Reflections collected | 11595 | 27436 |
| Independent reflections | 2863 [R(int) = 0.0249] | 3145 [R(int) = 0.0433] |
| Goodness-of-fit on $F^2$ | 1.037 | 1.050 |
| Final R indices [I > 2σ(I)] | $R_1$ =0.0315, $\omega R_2$ = 0.0877 | $R_1$ = 0.0365, $\omega R_2$ = 0.0874 |
| R indices (all data) | $R_1$ =0.0372, $\omega R_2$ = 0.0923 | $R_1$ = 0.0538, $\omega R_2$ = 0.0954 |

REFERENCES (S1) Yang, Y.; Hughes, R. P.; Aprahamian, I. *J. Am. Chem. Soc.* 2012, 134, 15221-15224.

(S2) (a) Lipshutz, B. H.; Kim, S.; Mollard, P.; Blomgren, P. A.; Stevens, K. L. *Tetrahedron* 1998, 54, 6999-7012. (b) Domasevitch, K. V.; Gerasimchuk, N. N.; Mokhir, A. *Inorg. Chem.* 2000, 39, 1227-1237.

(S3) COSMO V1.61, *Software for the CCD Detector Systems for Determining Data Collection Parameters.* Bruker Analytical X-ray Systems, Madison, Wis. (2009).

(S4) APEX2 V2010.11-3. Software *for the CCD Detector System*; Bruker Analytical X-ray Systems, Madison, Wis. (2010).

(S4) SAINT V 7.68A Software *for the Integration of CCD Detector System* Bruker Analytical X-ray Systems, Madison, Wis. (2010).

(S5) Blessing, R. H. *Acta Cryst. A* 1995, 51, 33-38.

(S6) Sheldrick, G. M. *Acta Cryst. A* 2008, 64, 112-122.

INCORPORATION BY REFERENCE

All publications, patents, and patent applications mentioned in this specification are herein incorporated by reference to the same extent as if each individual publication, patent, or patent application was specifically and individually indicated to be incorporated by reference.

What is claimed is:

1. A compound of the Formula II:

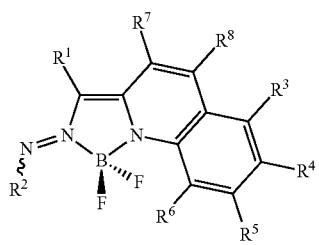

(II)

or a salt thereof, wherein $R^2$ is oriented cis or trans to the tricycle;

$R^1$ is H, CN, $CO_2H$, $CO_2(C_{1-6}$-alkyl), $C_{1-6}$-alkyl, $C_{6-19}$-aryl, OH, $O(C_{1-6}$-alkyl), $OC(O)(C_{1-6}$-alkyl), $NH_2$, $NH(C_{1-6}$-alkyl), $N(C_{1-6}$-alkyl)$_2$, or $NHC(O)(C_{1-6}$-alkyl);

$R^2$ is $C_{6-19}$-aryl or $C_{3-14}$-heteroaryl; and $R^3$, $R^4$, $R^5$, $R^6$, $R^7$, and $R^8$ are each, independently, H, $C_{1-6}$-alkyl, $C_{6-19}$-aryl, OH, $O(C_{1-6}$-alkyl), $OC(O)(C_{1-6}$-alkyl), $NH_2$, $NH(C_{1-6}$-alkyl), $N(C_{1-6}$-alkyl)$_2$, or $NHC(O)(C_{1-6}$-alkyl) or a group corresponding to a small molecule pharmaceutical; or $R^3$ and $R^4$, $R^4$ and $R^5$, $R^5$ and $R^6$ or $R^7$ and $R^8$, when taken together, optionally form a fused aryl, fused heteroaryl, fused $C_{3-6}$-cycloalkyl, or fused heterocycle, wherein the fused aryl, fused heteroaryl, fused cycloalkyl, or fused heterocycle is optionally substituted one or more times with $C_{1-6}$-alkyl, $C_{6-19}$-aryl, OH, $O(C_{1-6}$-alkyl), $OC(O)(C_{1-6}$-alkyl), $NH_2$, $NH(C_{1-6}$-alkyl), $N(C_{1-6}$-alkyl)$_2$, or $NHC(O)(C_{1-6}$-alkyl).

2. The compound of claim 1, wherein $R^2$ is unsubstituted $C_{6-9}$-aryl or unsubstituted $C_{3-14}$-heteroaryl.

3. The compound of claim 1, wherein $R^3$, $R^4$, $R^5$, $R^6$, $R^7$, and $R^8$ are each H.

4. The compound of claim 1, wherein $R^1$ is CN.

5. The compound of claim 1, wherein $R^2$ is phenyl, wherein the phenyl is substituted with $N(C_{1-6}$-alkyl)$_2$, $O(C_{1-6}$-alkyl), piperazinyl, (N-methyl)piperazinyl, piperidinyl, morpholinyl or a group corresponding to a cholesterol molecule.

6. The compound of claim 1, wherein $R^2$ is phenyl, wherein the phenyl is substituted at the para position with $N(CH_3)_2$, $OCH_3$, piperazinyl, (N-methyl)piperazinyl, piperidinyl, morpholinyl or a group corresponding to a cholesterol molecule.

7. The compound of claim 1, wherein $R^2$ is oriented cis to the tricycle.

8. The compound of claim 1, wherein $R^2$ is oriented trans to the tricycle.

9. The compound of claim 1, wherein $R^2$ is unsubstituted phenyl.

10. A photochromic molecular switch comprising at least one compound of the Formula II:

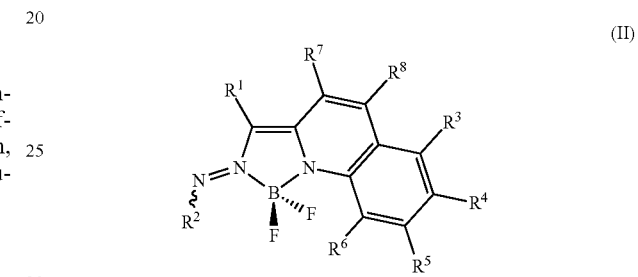

(II)

or a salt thereof, wherein $R^2$ is oriented cis or trans to the tricycle;

$R^1$ is H, CN, $CO_2H$, $CO_2(C_{1-6}$-alkyl), $C_{1-6}$-alkyl, $C_{6-19}$-aryl, OH, $O(C_{1-6}$-alkyl), $OC(O)(C_{1-6}$-alkyl), $NH_2$, $NH(C_{1-6}$-alkyl), $N(C_{1-6}$-alkyl)$_2$, or $NHC(O)(C_{1-6}$-alkyl);

$R^2$ is $C_{6-19}$-aryl or $C_{3-14}$-heteroaryl; and $R^3$, $R^4$, $R^5$, $R^6$, $R^7$, and $R^8$ are each, independently, H, $C_{1-6}$-alkyl, $C_{6-19}$-aryl, OH, $O(C_{1-6}$-alkyl), $OC(O)(C_{1-6}$-alkyl), $NH_2$, $NH(C_{1-6}$-alkyl), $N(C_{1-6}$-alkyl)$_2$, or $NHC(O)(C_{1-6}$-alkyl); or $R^3$ and $R^4$, $R^4$ and $R^5$, $R^5$ and $R^6$ or $R^7$ and $R^8$, when taken together, optionally form a fused aryl, fused heteroaryl, fused $C_{3-6}$-cycloalkyl, or fused heterocycle, wherein the fused aryl, fused heteroaryl, fused cycloalkyl, or fused heterocycle can be optionally substituted one or more times with $C_{1-6}$-alkyl, $C_{6-19}$-aryl, OH, $O(C_{1-6}$-alkyl), $OC(O)(C_{1-6}$-alkyl), $NH_2$, $NH(C_{1-6}$-alkyl), $N(C_{1-6}$-alkyl)$_2$, or $NHC(O)(C_{1-6}$-alkyl).

11. The photochromic molecular switch of claim 10, wherein $R^2$ is unsubstituted $C_{6-19}$-aryl or unsubstituted $C_{3-14}$-heteroaryl.

12. The photochromic molecular switch of claim 10, wherein $R^3$, $R^4$, $R^5$, $R^6$, $R^7$, and $R^8$ are each H.

13. The photochromic molecular switch of claim 10, wherein $R^1$ is CN.

14. The photochromic molecular switch of claim 10, wherein $R^2$ is phenyl, wherein the phenyl is substituted with $N(C_{1-6}$-alkyl)$_2$, $O(C_{1-6}$-alkyl), piperazinyl, (N-methyl)piperazinyl, piperidinyl, morpholinyl or a group corresponding to a cholesterol molecule.

15. The photochromic molecular switch of claim 10, wherein $R^2$ is phenyl, wherein the phenyl is optionally substituted at the para position with $N(CH_3)_2$, $OCH_3$, piperazinyl, (N-methyl)piperazinyl, piperidinyl, morpholinyl or a group corresponding to a cholesterol molecule.

16. The photochromic molecular switch of claim 10, wherein $R^2$ is oriented cis to the tricycle.

17. The photochromic molecular switch of claim 10, wherein $R^2$ is oriented trans to the tricycle.

18. The photochromic molecular switch of claim 10, wherein $R^2$ is unsubstituted phenyl.

19. A method of switching a molecular switch, wherein the molecular switch comprises a compound of claim 1 or a salt thereof in the trans or cis configuration, wherein the method comprises applying electromagnetic radiation to the molecular switch at a first wavelength effective to cause the trans→cis isomerization of the compound or salt thereof in the trans configuration or applying electromagnetic radiation to the molecular switch at a second wavelength effective to cause the cis→trans isomerization of the compound or salt thereof in the cis configuration or a combination thereof.

20. The method of claim 19, wherein the electromagnetic radiation is generated by an infrared light source and/or a visible light source.

21. The method of claim 19, wherein the electromagnetic radiation is generated by a visible light source.

22. The method of claim 20, wherein the first wavelength ($\lambda$) is between 400 nanometers and 1000 nanometers.

23. The method of claim 20, wherein the second wavelength ($\lambda$) is between 400 nanometers and 1000 nanometers.

24. The method of claim 20, wherein the first wavelength ($\lambda$) is between 450 nanometers and 850 nanometers.

25. The method of claim 20, wherein the second wavelength ($\lambda$) is between 450 nanometers and 850 nanometers.

26. The molecular switch of claim 10, wherein the salt of the compound is a pharmaceutically acceptable salt.

27. The compound of claim 1, wherein the $C_{6-19}$-aryl or $C_{3-14}$-heteroaryl is independently substituted one or more times at the para and/or ortho positions with $C_{1-6}$-alkyl, $C_{6-19}$-aryl, $C_{3-14}$-heteroalkyl, OH, ($C_{1-6}$ alkyl), OC(O)($C_{1-6}$ alkyl), $NH_2$, $NH(C_{1-6}$-alkyl), $N(C_{1-6}$-alkyl)$_2$, or NHC(O)($C_{1-6}$ alkyl).

28. The photochromic molecular switch of claim 10, wherein the $C_{6-19}$-aryl or $C_{3-14}$-heteroaryl is independently substituted one or more times at the para and/or ortho positions with $C_{1-6}$-alkyl, $C_{6-19}$-aryl, $C_{3-14}$-heteroalkyl, OH, O($C_{1-6}$ alkyl), OC(O)($C_{1-6}$ alkyl), $NH_2$, $NH(C_{1-6}$-alkyl), $N(C_{1-6}$-alkyl)$_2$, or NHC(O)($C_{1-6}$ alkyl).

29. A photopharmaceutical compound of the Formula II:

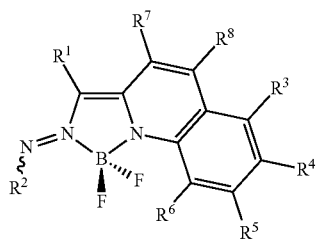

(II)

or a salt thereof, wherein $R^2$ is oriented cis or trans to the tricycle;

$R^1$ is H, CN, $CO_2H$, $CO_2(C_{1-6}$-alkyl), $C_{1-6}$-alkyl, $C_{6-19}$-aryl, OH, O($C_{1-6}$-alkyl), OC(O)($C_{1-6}$-alkyl), $NH_2$, $NH(C_{1-6}$-alkyl), $N(C_{1-6}$-alkyl)$_2$, or NHC(O)($C_{1-6}$-alkyl);

$R^2$ is $C_{6-19}$-aryl or $C_{3-14}$-heteroaryl; and $R^3$, $R^4$, $R^5$, $R^6$, $R^7$, and $R^8$ are each, independently, H, $C_{1-6}$-alkyl, $C_{6-19}$-aryl, OH, O($C_{1-6}$-alkyl), OC(O)($C_{1-6}$-alkyl), $NH_2$, $NH(C_{1-6}$-alkyl), $N(C_{1-6}$-alkyl)$_2$, NHC(O)($C_{1-6}$-alkyl) or a group corresponding to a small molecule pharmaceutical; or $R^3$ and $R^4$, $R^4$ and $R^5$, $R^5$ and $R^6$ or $R^7$ and $R^8$, when taken together, optionally form a fused aryl, fused heteroaryl, fused $C_{3-6}$-cycloalkyl, or fused heterocycle, wherein the fused aryl, fused heteroaryl, fused cycloalkyl, or fused heterocycle is optionally substituted one or more times with $C_{1-6}$-alkyl, $C_{6-19}$-aryl, OH, O($C_{1-6}$-alkyl), OC(O)($C_{1-6}$-alkyl), $NH_2$, $NH(C_{1-6}$-alkyl), $N(C_{1-6}$-alkyl)$_2$, or NHC(O)($C_{1-6}$-alkyl), wherein at least one of $R^3$, $R^4$, $R^5$, $R^6$, $R^7$, and $R^8$ is a group corresponding to a small molecule pharmaceutical, or the salt is a pharmaceutically acceptable salt.

30. A method of treating a patient in need of therapy, comprising:
administering a therapeutically effective amount of the photopharmaceutical compound of claim 29 in the trans or cis configuration to a patient in need thereof; and
applying electromagnetic radiation to a tissue comprising the photopharmaceutical compound at a first wavelength effective to cause the trans→cis isomerization of the photopharmaceutical compound in the trans configuration or applying electromagnetic radiation to the photopharmaceutical compound at a second wavelength effective to cause the cis→trans isomerization of the photopharmaceutical compound in the cis configuration or a combination thereof, wherein one isomer has a higher binding affinity for a target of the tissue than the other isomer.

31. The method of claim 30, wherein the electromagnetic radiation is generated by an infrared light source and/or a visible light source.

32. The photopharmaceutical compound of claim 29, wherein $R^2$ is unsubstituted $C_{6-19}$-aryl or unsubstituted $C_{3-14}$-heteroaryl.

33. The photopharmaceutical compound of claim 29, wherein $R^3$, $R^4$, $R^5$, $R^6$, $R^7$, and $R^8$ are each H.

34. The photopharmaceutical compound of claim 29, wherein $R^1$ is CN.

35. The photopharmaceutical compound of claim 29, wherein $R^2$ is phenyl, wherein the phenyl is substituted with $N(C_{1-6}$-alkyl)$_2$, O($C_{1-6}$-alkyl), piperazinyl, (N-methyl)piperazinyl, piperidinyl, morpholinyl or a group corresponding to a cholesterol molecule.

36. The photopharmaceutical compound of claim 29, wherein $R^2$ is phenyl, wherein the phenyl is optionally substituted at the para position with $N(CH_3)_2$, $OCH_3$, piperazinyl, (N-methyl)piperazinyl, piperidinyl, morpholinyl or a group corresponding to a cholesterol molecule.

37. The photopharmaceutical compound of claim 29, wherein $R^2$ is oriented cis to the tricycle.

38. The photopharmaceutical compound of claim 29, wherein $R^2$ is oriented trans to the tricycle.

39. A method of switching a molecular switch, wherein the molecular switch comprises a compound or salt thereof of claim 29 in the trans or cis configuration, wherein the method comprises applying electromagnetic radiation to the molecular switch at a first wavelength effective to cause the trans→cis isomerization of the compound or salt thereof in the trans configuration or applying electromagnetic radiation to the molecular switch at a second wavelength effective to cause the cis→trans isomerization of the compound or salt thereof in the cis configuration or a combination thereof.

* * * * *